US012686859B2

(12) United States Patent
Do et al.

(10) Patent No.: US 12,686,859 B2
(45) Date of Patent: *Jul. 21, 2026

(54) METHOD FOR SELECTION OF HIGH M6P RECOMBINANT PROTEINS

(71) Applicant: Amicus Therapeutics, Inc., Philadelphia, PA (US)

(72) Inventors: Hung V. Do, New Hope, PA (US); Russell Gotschall, Doylestown, PA (US)

(73) Assignee: Amicus Therapeutics, Inc., Philadelphia, PA (US)

( * ) Notice: Subject to any disclaimer, the term of this patent is extended or adjusted under 35 U.S.C. 154(b) by 122 days.

This patent is subject to a terminal disclaimer.

(21) Appl. No.: 17/931,351

(22) Filed: Sep. 12, 2022

(65) Prior Publication Data

US 2023/0079225 A1 Mar. 16, 2023

Related U.S. Application Data

(63) Continuation of application No. 16/252,519, filed on Jan. 18, 2019, now Pat. No. 11,441,138, which is a continuation of application No. 15/473,994, filed on Mar. 30, 2017, now Pat. No. 10,227,577.

(60) Provisional application No. 62/457,584, filed on Feb. 10, 2017, provisional application No. 62/315,400, filed on Mar. 30, 2016.

(51) Int. Cl.
*C12N 9/26* (2006.01)
*A61K 38/00* (2006.01)

(52) U.S. Cl.
CPC ...... *C12N 9/2408* (2013.01); *C12Y 302/0102* (2013.01); *A61K 38/00* (2013.01)

(58) Field of Classification Search
CPC .. C12N 9/2408; C12Y 302/0102; C07K 1/18; C07K 1/22; C07K 1/34; A61K 38/00
See application file for complete search history.

(56) References Cited

U.S. PATENT DOCUMENTS

| | | | |
|---|---|---|---|
| 4,837,237 | A | 6/1989 | Rohrschneider |
| 4,985,445 | A | 1/1991 | Tsuruoka et al. |
| 5,011,829 | A | 4/1991 | Hirsch et al. |
| 5,103,008 | A | 4/1992 | Scudder et al. |
| 5,236,838 | A | 8/1993 | Rasmussen et al. |
| 5,399,567 | A | 3/1995 | Platt et al. |
| 5,472,969 | A | 12/1995 | Platt et al. |
| 5,580,757 | A | 12/1996 | Desnick et al. |
| 5,786,369 | A | 7/1998 | Platt et al. |
| 5,801,185 | A | 9/1998 | Platt et al. |
| 5,879,680 | A | 3/1999 | Ginns et al. |
| 6,083,725 | A | 7/2000 | Selden et al. |
| 6,118,045 | A | 9/2000 | Reuser et al. |
| 6,210,666 | B1 | 4/2001 | Miyamura |
| 6,225,325 | B1 | 5/2001 | Jacob |
| 6,274,597 | B1 | 8/2001 | Fan |
| 6,395,884 | B1 | 5/2002 | Selden et al. |
| 6,451,600 | B1 | 9/2002 | Rasmussen et al. |
| 6,458,574 | B1 | 10/2002 | Selden et al. |
| 6,461,609 | B1 | 10/2002 | Calhoun et al. |
| 6,465,488 | B1 | 10/2002 | Butters et al. |
| 6,534,300 | B1 | 3/2003 | Canfield |
| 6,537,785 | B1 | 3/2003 | Canfield |
| 6,545,021 | B1 | 4/2003 | Mueller et al. |
| 6,583,158 | B1 | 6/2003 | Fan et al. |
| 6,589,964 | B2 | 7/2003 | Fan et al. |
| 6,599,919 | B2 | 7/2003 | Fan et al. |
| 6,696,059 | B2 | 2/2004 | Jacob et al. |
| 6,916,829 | B2 | 7/2005 | Fan et al. |
| 7,141,582 | B2 | 11/2006 | Fan et al. |
| 7,351,410 | B2 | 4/2008 | Van Bree et al. |
| 7,371,366 | B2 | 5/2008 | Canfield |
| 7,396,811 | B2 | 7/2008 | Lebowitz et al. |
| 7,560,424 | B2 | 7/2009 | Lebowitz et al. |
| 7,655,226 | B2 | 2/2010 | Van Bree et al. |
| 7,658,916 | B2 | 2/2010 | Zhu et al. |
| 7,723,296 | B2 | 5/2010 | Zhu |
| 7,785,856 | B2 | 8/2010 | Lebowitz et al. |
| 7,858,576 | B2 | 12/2010 | Lebowitz et al. |
| 7,910,545 | B2 | 3/2011 | Meeker et al. |
| 7,981,864 | B2 | 7/2011 | Lebowitz |
| 8,759,501 | B2 | 6/2014 | Zhu et al. |

(Continued)

FOREIGN PATENT DOCUMENTS

| | | |
|---|---|---|
| CN | 104379162 A | 2/2015 |
| CN | 104379162 B | 3/2017 |

(Continued)

OTHER PUBLICATIONS

Lysosomal Acid -Glucosidase Consists of Four Different Peptides Processed from a Single Chain Precursor *. JBC (2005), 280(5):6780-6791. (Year: 2005).*

Khanna, R. , et al., "Co-Administration of the Pharmacological Chaperone AT2221 with a Proprietary Recombinant Human Acid a-Glucosidase Leads to Greater Plasma Exposure and Substrate Reduction Compared to Alglucosidase Alfa", Amicus Therapeutics: Poster from the 12th Annual Lysosomal Disease Network WORLDSymposium Meeting, Feb. 29-Mar. 4, 2016, San Diego, California; 1 page.

(Continued)

*Primary Examiner* — Iqbal H Chowdhury
(74) *Attorney, Agent, or Firm* — SERVILLA WHITNEY LLC

(57) ABSTRACT

Methods for the production, capturing and purification of recombinant human lysosomal proteins are described. Such recombinant human lysosomal proteins can have high content of mannose-6-phosphate residues. Also described are pharmaceutical compositions comprising such recombinant human lysosomal proteins, as well as methods of treatment and uses of such recombinant human lysosomal proteins.

20 Claims, 42 Drawing Sheets

Specification includes a Sequence Listing.

(56) References Cited

U.S. PATENT DOCUMENTS

| | | | | |
|---|---|---|---|---|
| 8,785,168 | B2 | 7/2014 | Lebowitz et al. | |
| 8,900,552 | B2 | 12/2014 | Chen | |
| 8,940,766 | B2 | 1/2015 | Boyd et al. | |
| 9,056,101 | B2 | 6/2015 | Lockhart | |
| 9,181,184 | B2 | 11/2015 | Mugrage et al. | |
| 9,186,420 | B2 | 11/2015 | Koeberl | |
| 9,249,399 | B2 | 2/2016 | Vervecken et al. | |
| 9,303,249 | B2 | 4/2016 | Valenzano et al. | |
| 9,404,100 | B2 | 8/2016 | Valenzano et al. | |
| 9,598,682 | B2 | 3/2017 | Callewaert et al. | |
| 10,046,033 | B2 | 8/2018 | Valenzano et al. | |
| 10,208,299 | B2 | 2/2019 | Gotschall et al. | |
| 10,227,577 | B2 | 3/2019 | Do et al. | |
| 10,464,962 | B2 | 11/2019 | Avila et al. | |
| 10,512,676 | B2 | 12/2019 | Char et al. | |
| 10,512,677 | B2 | 12/2019 | Valenzano et al. | |
| 10,857,212 | B2 | 12/2020 | Do et al. | |
| 10,961,522 | B2 | 3/2021 | Gotschall et al. | |
| 11,278,601 | B2 | 3/2022 | Do et al. | |
| 11,441,138 | B2 * | 9/2022 | Do | A61P 3/08 |
| 2002/0049233 | A1 | 4/2002 | Kararli et al. | |
| 2002/0073438 | A1 | 6/2002 | Reuser et al. | |
| 2002/0095135 | A1 | 7/2002 | Meeker et al. | |
| 2002/0137125 | A1 | 9/2002 | Zhu | |
| 2002/0157123 | A1 | 10/2002 | Reuser et al. | |
| 2004/0180419 | A1 | 9/2004 | Fan | |
| 2004/0204379 | A1 | 10/2004 | Cheng et al. | |
| 2005/0058634 | A1 | 3/2005 | Zhu | |
| 2005/0244400 | A1 | 11/2005 | LeBowitz et al. | |
| 2006/0121018 | A1 | 6/2006 | Lebowitz | |
| 2006/0264467 | A1 | 11/2006 | Mugrage et al. | |
| 2007/0178081 | A1 | 8/2007 | Fan | |
| 2009/0117091 | A1 | 5/2009 | Lebowitz et al. | |
| 2009/0191178 | A1 | 7/2009 | Zankel et al. | |
| 2009/0203575 | A1 | 8/2009 | Lebowitz et al. | |
| 2010/0119502 | A1 | 5/2010 | Do et al. | |
| 2010/0173385 | A1 * | 7/2010 | Zhu | A61K 38/1709 435/200 |
| 2010/0260740 | A1 | 10/2010 | Boyd et al. | |
| 2010/0266571 | A1 | 10/2010 | Lockhart et al. | |
| 2011/0136151 | A1 | 6/2011 | Wustman et al. | |
| 2011/0189710 | A1 | 8/2011 | Wustman et al. | |
| 2011/0223147 | A1 | 9/2011 | Lebowitz | |
| 2011/0268721 | A1 | 11/2011 | Do et al. | |
| 2011/0300120 | A1 | 12/2011 | Avila et al. | |
| 2012/0064545 | A1 | 3/2012 | Khanna et al. | |
| 2012/0148556 | A1 | 6/2012 | Lebowitz et al. | |
| 2013/0158239 | A1 | 6/2013 | Callewaert et al. | |
| 2014/0186326 | A1 | 7/2014 | Canfield et al. | |
| 2014/0193390 | A1 | 7/2014 | Valenzano et al. | |
| 2014/0249054 | A1 | 9/2014 | Gelb et al. | |
| 2015/0044194 | A1 | 2/2015 | Valenzano et al. | |
| 2015/0086530 | A1 | 3/2015 | Greene et al. | |
| 2015/0147309 | A1 | 5/2015 | Parenti et al. | |
| 2015/0258081 | A1 | 9/2015 | Lukas et al. | |
| 2015/0352042 | A1 | 12/2015 | Char et al. | |
| 2016/0051528 | A1 | 2/2016 | Mugrage et al. | |
| 2016/0184410 | A1 | 6/2016 | Chen | |
| 2016/0243203 | A1 | 8/2016 | Van Bree et al. | |
| 2017/0056483 | A1 | 3/2017 | Valenzano et al. | |
| 2017/0298335 | A1 | 10/2017 | Gotschall et al. | |
| 2017/0335301 | A1 | 11/2017 | Do et al. | |
| 2018/0221357 | A1 | 8/2018 | Mugrage et al. | |
| 2018/0360928 | A1 | 12/2018 | Valenzano et al. | |
| 2019/0382742 | A1 | 12/2019 | Do et al. | |

FOREIGN PATENT DOCUMENTS

| | | | |
|---|---|---|---|
| CN | 107075468 | A | 8/2017 |
| EP | 1137762 | B1 | 10/2008 |
| EP | 2020438 | A1 | 2/2009 |
| EP | 1820862 | A2 | 8/2017 |
| FR | 2861991 | A1 | 5/2005 |
| JP | 2005523882 | A | 8/2005 |
| JP | 2007523648 | A | 8/2007 |
| JP | 2008525457 | A | 7/2008 |
| JP | 2008545657 | A | 12/2008 |
| JP | 2010525084 | A | 7/2010 |
| JP | 2011512876 | A | 4/2011 |
| NO | 2012145644 | A1 | 10/2012 |
| WO | 00034451 | A1 | 6/2000 |
| WO | 01019955 | A2 | 3/2001 |
| WO | 0197829 | A2 | 12/2001 |
| WO | 03032907 | A2 | 4/2003 |
| WO | 2004069190 | A2 | 8/2004 |
| WO | 2005077093 | A2 | 8/2005 |
| WO | 2006071613 | A2 | 7/2006 |
| WO | 2006125141 | A2 | 11/2006 |
| WO | 2008112525 | A2 | 9/2008 |
| WO | 2008134628 | A2 | 11/2008 |
| WO | 2009066069 | A1 | 5/2009 |
| WO | 2009102895 | A2 | 8/2009 |
| WO | 2009114679 | A2 | 9/2009 |
| WO | 2010015816 | A2 | 2/2010 |
| WO | 2010075010 | A2 | 7/2010 |
| WO | 2010148253 | A2 | 12/2010 |
| WO | 2011039634 | A2 | 4/2011 |
| WO | 2011109600 | A1 | 9/2011 |
| WO | 2012042386 | A2 | 4/2012 |
| WO | 2013013017 | A2 | 1/2013 |
| WO | 2013091897 | | 6/2013 |
| WO | 2013136189 | A2 | 9/2013 |
| WO | 2013166249 | A1 | 11/2013 |
| WO | 2015097088 | | 7/2015 |
| WO | 2016054231 | A1 | 4/2016 |
| WO | 2017049161 | A1 | 3/2017 |
| WO | 2017117407 | A1 | 7/2017 |
| WO | 2017173059 | A1 | 10/2017 |
| WO | 2017173060 | A1 | 10/2017 |
| WO | 2018213340 | A1 | 11/2018 |
| WO | 2020163480 | A1 | 8/2020 |
| WO | 2022174037 | A1 | 8/2022 |

OTHER PUBLICATIONS

Lembcke, B. , et al., "Lysosomal storage of glycogen as a sequel of alpha-glucosidase inhibition by the absorbed deoxynojirimycin derivative emiglitate (BAYo1248). A drug-induced pattern of hepatic glycogen storage mimicking Pompe's disease (glycogenesis type II)", Res Exp Med, 191 (6): 389-404. (1991).

Lun, Y. , et al., "A Novel Recombinant Human Acid Alpha-Glucosidase, ATB200, Leads to Greater Substrate Reduction and Improvement in Pompe Disease-Relevant Markers Compared to Alglucosidase Alfa in Gaa KO Mice", Amicus Technologies: Poster from the 13th Annual Lysosomal Disease Network WORLDSymposium, San Diego, CA, Feb. 13-17, 2017; 1 page.

Lun, Y. , et al., "Histological examination of the effect of a highly phosphorylated proprietary recombinant human acid alpha-glucosidase on glycogen reduction in disease-relevant muscles of Pompe mice", Amicus Technologies: Poster from the Lysosomal Disease Network 11th WORLDSymposium, Feb. 9-13, 2015, Orlando, Florida; 1 page.

Lun, Y. , et al., "Stabilized Next-Generation Recombinant Human Acid Alpha-Glucosidase ATB200 Clears Accumulated Glycogen and Reverses Cellular Dysfunction to Increase Muscle Strength in A Mouse Model of Pompe Disease", Amicus Therapeutics: Poster from the 2017 Muscular Dystrophy Association Scientific Conference, Mar. 19-11, 2017, Arlington, Virginia; 1 page.

Martiniuk , et al., "Correction of Glycogen Storage Disease Type II by Enzyme Replacement with a Recombinant Human Acid Maltase Produced by Over-Expression in a CHO-HDFR"e9 Cell Line", Biochemical and Biophysical Research Communications, 276(3):917-923 (2000).

McVie-Wylie , et al., "Biochemical and pharmacological characterization of different recombinant acid aglucosidase preparations evaluated for the treatment of Pompe disease", Molecular Genetics and Metabolism, 94: 448-455 (2008).

Sathe, S. , et al., "Preliminary Pharmacokinetic and Safety Data in Patients With Pompe Disease in Firstin-Human Study Receiving

(56) References Cited

OTHER PUBLICATIONS

ATB200/AT2221", Amicus Therapeutics: Poster from the 2017 Muscular Dystrophy Association Scientific Conference, Mar. 19-11, 2017, Arlington, Virginia; 1 page.
Sathe, S. , et al., "Preliminary Safety, Pharmacokinetic, Pharmacodynamic, and Efficacy Data in Patients With Pompe Disease Receiving ATB200/AT2221 in First-in-Human Study", Amicus Therapeutics: Poster from the 4th International Glycogen Storage Disease (GSD) Conference, Jun. 15-17, 2017, University Medical Center, Groningen, The Netherlands; 1 page.
Shin-Buehring, Y.S. , et al., "Separation of acid and neutral a-glucosidase isoenzymes from fetal and adult tissues, cultivated fibroblasts and amniotic fluid cells by DEAE-cellulose and Sephadex G-100 column chromatography", Clinica Chimica Acta 89(3):393-404, 12 pages (1978).
Toonkool, P, et al., (2006) "Expression and purification of dalcochinase, a beta-glucosidase from Dalbergia cochinchinensis Pierre, in yeast and bacterial hosts", Protein Expression and Purification, 48(2):195-204.
Valenzano, K. J., et al., "Identification and characterization of pharmacological chaperones to correct enzyme deficiencies in lysosomal storage disorders", Assay and Drug Development Technologies, 9(3):213-235. (Jun. 2011).
Van Hove, J.L.K. , et al., "High-level production of recombinant human lysosomal acid a-glucosidase in Chinese hamster ovary cells which targets to heart muscle and corrects glycogen accumulation in fibroblasts from patients with Pompe disease", Proc Natl Acad Sci USA, 93:65-70. (1996).
Hoja-Lukowicz, Dorota , et al., "Characterization of the oligosaccharide component of microsomal [beta]-glucuronidase from rat liver", Biochimie, FR, (Jun. 1, 2004), vol. 86, No. 6, pp. 363-372.
Courageot, M-P. et al. (2000) "a-Glucosidase inhibitors reduce dengue virus production by affecting the initial steps ofvirion morphogenesis in the endoplasmic reticulum" J Viral, 74:564-572.
Cox, T. et al. (2000) "Novel oral treatment of Gaucher's disease with N-butyldeoxynojirimycin (OGT 918) to decrease substrate biosynthesis" The Lancet, 355:1481-1485.
Dale, M.P. et al. (1985) "Reversible inhibitors of 6-glucosidase" Biochemistry, 24:3530-3539.
Database Score. Seq ID No. 1 sequence in WO 2012145644A1. Retrieved from: http://score.uspto.gov/ScoreAccessWeb/viewSeqldResult.htm, pp. 1-3; accessed Jan. 22, 2018, 3 pages.
Duke University Medical Center (1997) "Duke Obtains FDA Designation for Pompe Disease Therapy" Press Release, dated Sep. 2, 1997, 2 pages.
European Application No. 15845664.0, filed Apr. 6, 2017, by Amicus Therapeutics, Inc.: Supplementary European Search Report, mailed Feb. 12, 2018, 13 pages.
Fryar, C.D. et al. (Oct. 2012) "Anthropometric Reference Data for Children and Adults: United States 2007-2010" National Center for Health Statistics. Vital Health Stat, Series 11, No. 252, 48 pages.
Genzyme Corporation (2010) Myozyme®. Highlights of Prescribing Information. Cambridge, MA: Genzyme Corporation, Jun. 2010, 3 pages.
Jeyakumar, M. et al. (1999) "Delayed symptom onset and increased life expectancy in Sandhoff disease mice treated with N-butyldeoxynojirimycin" Proc Natl Acad Sci USA, 96:6388-6393.
Khanna. R. et al. (2012) "The pharmacological chaperone AT2220 increases recombinant human acid aglucosidase uptake and glycogen reduction in a mouse model of Pompe disease" PLoS ONE, 7(7):e40776, 14 pages.
Kishnani, P. et al. (2017) "Duvoglustat HCI Increases Systemic and Tissue Exposure of Active Acid a-Glucosidase in Pompe Patients Co-administered with Alglucosidase a" Molecular Therapy, 25(5):1199-1208.
Klinge, L. et al. (2005) "Enzyme replacement therapy in classical infantile Pompe disease: results of a ten-month follow-up study" Neuropediatrics, 36(1):6-11.
Legler, G. and S. Pohl (1986) "Synthesis of 5-amino-5-deoxy-D-galactopyranose and 1,5-dideoxy-1,5-imino-D-galactitol, and their inhibition of alpha- and beta-D-galactosidases" Carbohydrate Res, 155: 119-129.
Mellor, H.R. et al. (2004) "Cellular effects of deoxynojirimycin analogues; uptake, retention and inhibition of glycosphingolipid biosynthesis" Biochem J, 381 :861-866.
Moreland et al., Lysosomal Acid alpha-Glucosidase Consists of Four Different Peptides Processed from a Single Chain Precursor, The Journal of Biological Chemistry, 2005, 280:6780-6791.
National Institutes of Heal th Clinical Center (2002) Patient Education Materials: Giving a subcutaneous injection. Bethesda, MD: NIH Clinical Center, 3 pages.
Okumiya et al., Chemical chaperones improve transport and enhance stability of mutant a-glucosidases in glycogen storage disease type II. Mol. Genet. Metab. 90: 49-57 (2007).
Parenti et al., A Chaperone Enhances Blood a-Glucosidase Activity in Pompe Disease Patients Treated with Enzyme Replacement Therapy. Mol. Ther. 22(11 ):2004-2012 (2014).
Parenti, G. et al. (2005) "Alpha-Glucosidase Enhancement in Fibroblasts from Patients with Pompe Disease" J Inherit Metab Dis, 28(Suppl. 1): 193, Abstract 383-P.
PCT International Search Report and Written Opinion mailed Jan. 6, 2016, in PCT/US2015/053252, 9 pages.
PCT International Search Report and Written Opinion mailed Mar. 7, 2017, in PCT/US2016/069243, 10 pages.
PCT International Search Report and Written Opinion mailed May 8, 2013, in PCT/US2013/029660, 8 pages.
PCT International Search Report and Written Opinion mailed Oct. 1, 2013, in PCT/US2013/039215, 9 pages.
Platt, F.M. et al. (1997) "Prevention of Lysosomal Storage in Tay-Sachs Mice Treated with Nbutyldeoxynojirimycin" Science, 276:428-431.
Porto, C. et al. (2009) "The Pharmacological Chaperone N-butyldeoxynojirimycin Enhances Enzyme Replacement Therapy in Pompe Disease Fibroblasts" Mo/ Ther, 17(6):964-971.
Raben, N. et al. (2005) "Replacing acid alpha-glucosidase in Pompe disease: recombinant and transgenic enzymes are equipotent, but neither completely clears glycogen from type II muscle fibers" Mol Ther, 11 (1):48-56.
Ruvinov, S.B. et al. (1995) "Monovalent Cations Partially Repair a Conformational Defect in a Mutant Tryptophan Synthase a2 132 Complex (,8-E109A)" J Biol Chem, 270: 17333-17338.
U.S. Appl. No. 14/379,131: Non-Final Office Action, dated Sep. 15, 2015, 13 pages.
Van Der Ploeg, AT. et al. (1988) "Receptor-Mediated Uptake of Acid a-Glucosidase Corrects Lysosomal Glycogen Storage in Cultured Skeletal Muscle" Pediatric Research, 24(1 ):90-94.
Van Hove, J.L.K. et al. (1997) "Purification of recombinant human precursor acid a-glucosidase" Biochem Mol Biol Int, 43(3):613-623.
Wilson, B.A. et al. (2003) Prentice Hall Nurse's Drug Guide 2003 Companion Website. [online]. Retrieved from: http://wps.prenhall.com/chet_wilson_drugguides_ 1 /6/1576/403472.cw/index.html; accessed Sep. 30, 2014.
International Search Report and Written Opinion issued in International Application No. PCT/US2017/024981, dated Aug. 3, 2017, 27 pages.
Amalfitano , et al., "Recombinant human acid a-glucosidase enzyme therapy for infantile glycogen storage disease type II: Results of a phase I/II clinical trial", Genetics in Medicine 3(2): 132-138 (2001).
Asano, N , et al., "Nitrogen-in-the-ring pyranoses and furanoses: structural basis of inhibition of mammalian glycosidases", J Med Chem, 37:3701-3706. (1994).
Banati, M , et al., "Enzyme replacement therapy induces T-cell responses in late-onset Pompe disease", Muscle Nerve, 44(5):720-726. (2011).
Barton, N. W., et al., "Replacement Therapy for Inherited Enzyme Deficiency-Macrophage-Targeted Glucocerebrosidase for Gaucher's Disease", N Eng J Med, 324:1464-1470. (1991).
Beck, M. , "Alglucosidase alfa: Long term use in the treatment of patients with Pompe disease", Therapeutics and Clinical Risk Management, 5:767-772. (Sep. 2009).

(56) References Cited

OTHER PUBLICATIONS

Block , et al., "Immobilized-metal affinity chromatography", (IMAC): a review. Methods Enzymol. 2009; 463: 439-73.
Butters, T. D., et al., "Imino Sugar Inhibitors for Treating the Lysosomal Glycosphingolipidoses", Glycobiology, 15(10):43E-52R. (2005).
Chavez , et al., "Domain 5 of the Cation-Independent Man nose 6-Phosphate Receptor Preferentially Binds Phosphodiesters (Man nose 6-Phosphate N-Acetylglucosamine Ester).", Biochemistry (2007), 46: 12604-12617.
Do, H. , et al., "ATB200/AT2221 Cleared Accumulated Glycogen and Reversed Cellular Dysfunction to Increase Functional Muscle Strength in Mouse Model of Pompe Disease", Amicus Technologies: Poster from the 13th Annual Lysosomal Disease Network WORLDSymposium, San Diego, CA, Feb. 13-17, 2017; Poster #7 4, Abstract A-348, 1 page. (2017).
Do, H. , "Chemical Conjugation of Targeting Peptide to ERTs Improve Receptor Binding and Substrate Clearance in Mouse Models of Disease", Amicus Technologies: Presentation from the 10th Lysosomal Disease Network WORLDSymposium, San Diego, CA, Feb. 10-13, 2014; 14 pages. (Feb. 13, 2014).
Do, H, et al., "Chemical Conjugation of Targeting Peptide to ERTs Improve Receptor Binding and Substrate Clearance in Mouse Models of Disease", Amicus Technologies: Poster from the 1 Oth Annual Lysosomal Disease Network WORLDSymposium, San Diego, CA, Feb. 10-13, 2014, Abstract #277; 1 page. (Feb. 13, 2014).
Gotschall, R. , et al., "ATB200/AT2221 Reverses Cellular Dysfunction and Increases Muscle Strength in a Pompe Disease Mouse Model", Amicus Therapeutics: Poster from the 4th International Glycogen Storage Disease (GSD) Conference, Jun. 15-17, 2017, University Medical Center, Groningen, The Netherlands; Abstract 48, 1 page.
Gotschall, R. , "Novel rhGAA with Optimal Glycosylation Is Significantly Better than Alglucosidase Alfa for Glycogen Clearance in Skeletal Muscles of Gaa KO Mice", Amicus Technologies: Poster from the ACMG Annual Clinical Genetics Meeting, Mar. 25-27, 2015, Salt Lake City, Utah; Abstract #739, 1 page. (2015).
Gotschall, R. , "Novel rhGAA with Optimal Glycosylation is Significantly Better than Alglucosidase Alfa for Glycogen Clearance in Skeletal Muscles of Gaa KO Mice", Amicus Technologies: Presentation from the 11th Lysosomal Disease Network WorldSymposium, Feb. 9-13, 2015, Orlando, Florida; 12 pages. (2015).
Gotschall, R. , et al., "Novel rhGAA with Optimal Glycosylation is Significantly Better than Alglucosidase Alfa for Glycogen Clearance in Skeletal Muscles of Gaa KO Mice", Amicus Technologies: Abstract from the 11th Lysosomal Disease Network WORLDSymposium, Feb. 9-13, 2015, Orlando, Florida. Abstract 94, 1 page. (2015).
Johnson, F. K., et al., "First-in-Human Preliminary Pharmacokinetic and Safety Data on a Novel Recombinant Acid a-Glucosidase, ATB200, Co-administered With the Pharmacological Chaperone AT2221 in ERT-Experienced Patients With Pompe Disease", Amicus Technologies: Poster from the 13th Annual Lysosomal Disease Network WORLDSymposium, San Diego, CA, Feb. 13-17, 2017; Poster #LB-26, 1 page.
Jongen, S P, et al., (2007) "N-glycans of recombinant human acid [alpha]-glucosidase expressed in the milk of transgenic rabbits", Database Embase Accession No. EMB-2007342042, Elsevier Science Publishers, (Glycobiology 17(6):600-619).
Khanna, R. , The pharmacological chaperone AT2220 increases the specific activity and lysosomal delivery of mutant acid alpha-glucosidase, and promotes glycogen reduction in a transgenic mouse model of Pompe disease (2014).
Parenti, et al., "Alpha-Glusosidase Enhancement in Fibroblasts from Patients with Pompe Disease", J. Inherit. Metab. Dis. vol. 28 Suppl. I, 2005, 193.
Nippon Rinsho, vol. 68, Suppl 8, pp. 665-669.
Seq ID No. 1 sequence in WO 2012145644 A1, from http://score.uspto.gov/ScoreAccessWeb/viewSeqldResult.htm, pp. 1-3, accessed Jan. 22, 2018.
Nilsson MI et al., lysosomal alpha-glucosidase preproprotein [*Homo sapiens*], Accession No. NP 000143.2, dated Jun. 26, 2021, 4 pages.
"Amicus' AT-GAA Shows Clinically Meaningful & Significant Improvements in Both Musculoskeletal and Respiratory Measures in Late-Onset Pompe Disease Compared to Standard of Care in Pivotal Phase 3 PROPEL Study", Amicus Therapeutics. 2021, Study on the web at: ir.amicusrx.com/news-releases/news-release-details/amicus-gaa-shows-clinically-meaningful-significant-improvements. pp. 1-5.
"Amicus Therapeutics Announces Additional Positive Data in Pompe Disease Phase 1/2 Study at World Muscle Society", Amicus Therapeutics, Oct. 4, 2017, 4 pages.
"Center for Disease Control and Prevention (Data Table of Weight-for-age Charts. 2001, pp. 1-15)."
"EMEA (2006, Scientific Discussion. pages 1-30)."
"Extended European Search Report for Application No. 20207542.0, mailed on Jul. 29, 2021, 11 pages."
"Extended European Search Report issued by the European Patent Office for Application No. 18802722.1, dated Jan. 20, 2021, 8 pages".
"Final Office Action in U.S. Appl. No. 11/440,473, dated Jan. 5, 2015, 8 pages."
"Final Office Action in U.S. Appl. No. 11/440,473, dated May 15, 2009 , 8 pages."
"Final Office Action in U.S. Appl. No. 11/440,473, dated May 19, 2010, 7 pages".
"Final Office Action in U.S. Appl. No. 11/440,473, dated May 9, 2011, 8 pages."
"Guidance for Industry: Estimating the Maximum Safe Starting Dose in Initial Clinical Trials for Therapeutics in Adult Healthy Volunteers", U.S. Department of Health and Human Services, Food and Drug Administration, Center for Drug Evaluation and Research (CDER), Jul. 2005, 30 pages.
"Non-Final Office Action in U.S. Appl. No. 11/440,473, dated Dec. 5, 2008, 8 pages."
"Non-Final Office Action in U.S. Appl. No. 11/440,473, dated Mar. 28, 2014, 9 pages".
"Non-Final Office Action in U.S. Appl. No. 11/440,473, dated May 7, 2008, 8 pages."
"Non-Final Office Action in U.S. Appl. No. 11/440,473, dated Sep. 14, 2009, 6 pages."
"Non-Final Office Action in U.S. Appl. No. 11/440,473, dated Sep. 30, 2010 , 8 pages".
"Non-Final Office Action in U.S. Appl. No. 17/665,179, dated Jul. 11, 2022, 15 pages."
"Opfolda—SmPC", Jun. 2023, 25 pgs.
"Opfolda US Label", Sep. 2023, 2 pgs.
"Pombiliti—SmPC", 37 pgs.
"Pombiliti US Label", Sep. 2023, 24 pgs.
"Pompe Phase 1/2 Study (ATB200-02) Preliminary Data", Amicus Therapeutics, Dec. 8, 2016, pp. 1-13.
"The extended European search report dated Jan. 27, 2021, issued in European Application No. 201774 73.4, 10 pages."
"World Symposium Investor Dinner Slides", Perspectives on Pompe: Progress, Persistence and Passion, Feb. 12, 2020, 41 pages.
Anding, et al., "Increasing Enzyme Mannose-6-Phosphate Levels but Not Miglustat Coadministration Enhances the Efficacy of Enzyme Replacement Therapy in Pompe Mice", Journal of Pharmacology and Experimental Therapeutics, vol. 387, No. 2, Sep. 7, 2023, pp. 188-203.
Andra, et al., "(Ask Dr, Andra: What are Human Equivalent Doses (HED) and How Do I Calculate Them? 2011 pp. 1-4)."
Bellotti, et al., "Molecular Approaches for the Treatment of Pompe Disease", Molecular Neurobiology, Springer US, New York, vol. 57, No. 2, Nov. 2019, 1259-1280.
Berge, et al., "Pharmaceutical Salts", Journal of Pharmaceutical Sciences, vol. 66, No. 1, Jan. 1977, 1-19.
Blair, Hannaha. , "Cipaglucosidase Alfa: First Approval", Drugs, vol. 83, No. 8, May 15, 2023, 739-745.

(56) References Cited

OTHER PUBLICATIONS

Cheung, et al., "Immobilized metal ion affinity chromatography: a review on its applications", Appl Microbiol Biotechnol, Oct. 2012, 1411-1420.
Chien, et al., "Pompe Disease: Early Diagnosis and Early Treatment Make a Difference", Pediatrics and Neonatology, 2013, 54, pp. 219-227.
Ciccone, Isabella, "Combination of Cipaglucosidase Alfa and Miglustat Shows SustainedMotor and Respiratory Function in Pompe Disease", https://www.neurologylive.com/view/combination-cipaglucosidase-alfa-miglustat-shows-sustained-motor-respiratory-function-pompe-disease (accessed Oct. 7, 2025), NeurologyLive, MJH Sciences, May 4, 2023.
Chien, et al. "Immunogenicity of cipaglucosidase alfa/miglustat versus alglucosidase alfa/placebo in late-onset Pompe disease (Lopd): A Phase III, randomized study (Propel)", Molecular Genetics and Metabolism, vol. 135, No. 2, Feb. 2022, S30.
Do, et al., "Stabilized next generation recombinant human acid alphaglucosidase ATB200 clears accumulated glycogen and reverses cellular dysfunction to increase functional muscle strength in a mouse model of Pompe disease", Molecular Genetics and Metabolism 120(12); p. S42 (2017).
Hermans, et al., "Human lysosomal a-glucosidase: functional characterization of the glycosylation sites", Biochem J. 289:681-686 (1993).
Kalia, et al., "Hydrolytic Stability of Hydrazones and Oximes", Angew Chem Int Ed Engl. 2008 ; 47(39): 7523-7526.
Kalia, et al., "Hydrolytic Stability of Hydrazones and Oximes", Supporting Information, Anal. Chem. 1968, 40, 700-706.
Khanna, et al., "Molecular Genetics and Metabolism", vol. 117, Issue 2, Feb. 2016, pp. S66-S67. doi:10.1016/j.ymgme.2015.12.318).
Kuperus, et al., "Long-term benefit of enzyme replacement therapy in Pompe disease A 5-year prospective study", Neurology 89:2365-2373 (2017).
Liu, et al., "The Impact of Sialic Acids on the Pharmacokinetics of a PEGylated Erythropoietin", Journal of Pharmaceutical Sciences, 2012, 101 :4414-4418.
Maga, et al., "Glycosylation-independent Lysosomal Targeting of Acid a-Glucosidase Enhances Muscle Glycogen Clearance in Pompe Mice*", The Journal of Biological Chemistry, vol. 288, No. 3, Jan. 2013, 1428-1483.
Nagase, et al., "Synthetic construct DNA, clone: pF1 KB4173, *Homo sapiens* GAA gene for lysosomal alpha-Jlucosidase precursor, complete eds, without stop codon, in Flexi system", Accession: AB384912.1.
Nair, et al., "A Simple Practice Guide for Dose Conversion Between Animals and Human", Journal of Basic and Clinical Pharmacy, vol. 7, No. 2, 2016, 5 pages, XP055407475.
Parenti , et al., "Lysosomal Storage Diseases: From Pathophysiology to Therapy". Annu. Rev. Med., 2015, 66(1):471-486.
Overkleeft, et al., "Generation of Specific Deoxynojirimycin-type Inhibitors of the Non-lysosomal Glucosylceramidase", The Journal of Biological Chemistry, 1998, vol. 273, No. 41, pp. 26522-26527.
Platt, et al., "N-Butyldeoxygalactonojirimycin Inhibits Glycolipid Biosynthesis but Does Not Affect N-Linked Oligosaccharide Processing", The Journal of Biological Chemistry, 1994, vol. 269, No. 43, pp. 27108-27114.
Raben, et al., "Deconstructing Pompe Disease by Analyzing Single Muscle Fibers", Autophagy, 2007, 3, pp. 546-552.
Richard, et al., "New Insights into Therapeutic Options for Pompe Disease", IUBMB Life, Oct. 2011, 979-986.
Roberts, et al., "First-in-Human Study of ATB200/AT2221 in Patients With Pompe Disease: Interim Results from the ATB200-02 Trial", The 22nd International Congress of the World Muscle Society, Oct. 3-7, 2017, St. Malo, France, 7 pages.
Schoser, et al., "A systemic review of the health economics of Pompe Disease", PharmacoEconomics. 3: 479-493. 2019.
Schoser, et al., "Safety and efficacy of cipaglucosidase alfa plus miglustat versus alglucosidase alfa plus placebo in late-onset Pompe disease (PROPEL): an international, randomised, double-blind, parallel-group, phase 3 trial", The Lancet Neurology, Elsevier, Amsterdam, NL, vol. 20, No. 12, Nov. 17, 2021, 1027-1037.
Shimada, et al., "Endoplasmic reticulum stress induces autophagy through activation of p38 MAPK in fibroblasts from Pompe disease patients carrying c.546GNT mutation", Molecular Genetics and Metabolism 104, 2011, 566-573.
Sola, et al., "Glycosylation of Therapeutic Proteins: An Effective Strategy to Optimize Efficacy", BioDrugs., 2010, 24(1 ):9-21.
Stanley, et al., "Essentials of Glycobiology", 2nd edition, Cold Spring Harbor (NY): Cold Spring Harbor Laboratory Press, Chapter 8, NCBI Bookshelf, 10 pages.
Sugawara, et al., "Structural modeling of mutant rt-glucosidases resulting in a processing/transport defect in Pompe disease", Journal of Human Genetics (2009) 54, 624-330.
Tajima, et al., Structural and biochemical studies on Pompe disease and a "pseudodeficiency of acid aglucosidase", J Hum Genet., 2007, 52:898-906.
Tarnopolsky, et al., "Pompe Disease: Diagnosis and Management. Evidence Based Guidelines from a Canadian Expert Panel", Canadian Journal of Neurological Sciences 43(4):472-485 (2016).
Winkel, et al., "Enzyme replacement therapy in late-onset Pompe's disease: a three-year follow-up", Ann. Neural. Apr. 2004;55(4): 495-502. PMID: 15048888. (Year: 2004).
Xu, et al., "Improved efficacy of a next-generation ERT in murine Pompe disease", JCI Insight, 2019, 4(5):e125358, 20 pages.
Zhou, et al., "Glycan Structure Determinants for Cation-Independent Mannose 6-Phosphate Receptor Binding and Cellular Uptake of a Recombinant Protein", Bioconjugate Chemistry, vol. 24, No. 12, Nov. 12, 2013, pp. 2025-2035.
Zhou, et al., "LC-MS/MS Analysis of Permethylated N-Glycans Facilitating Characterization", Anal Bioanal Chem, vol. 409(2), 2017, pp. 453-466.
Zhou, et al., "The Mechanistic Impact of N-Glycosylation on Stability, Pharmacokinetics, and Immunogenicity of Therapeutic Proteins", Journal of Pharmaceutical Sciences, 2019, 108:1366-1377.
Zhu, et al., "Carbohydrate-remodelled acid a-glucosidase with higher affinity for the cation-independent mannose 6- phosphate receptor demonstrates improved delivery to muscles of Pompe mice", Biochem. J., 389 (Pt 3), 2005, 619-628.
Zhu, et al., "Conjugation of Mannose 6-Phosphate-containing Oligosaccharides to Acid [alpha]-Glucosidase Improves the Clearance of Glycogen in Pompe Mice", Journal of Biological Chemistry, vol. 279, No. 48, Nov. 26, 2004, pp. 50336-50341.
Zhu, et al., "Glycoengineered Acid α-Glucosidase With Improved Efficacy at Correcting the Metabolic Aberrations and Motor Function Deficits in a Mouse Model of Pompe Disease", The American Society of Gene Therapy, Molecular Therapy, vol. 17 No. 6, 954-963 Jun. 2009.
Sun, et al., "Application of immobilized metal affinity chromatography in proteomics", Expert Review of Proteomics, 2(5), 649-657, 2005, DOI: 10.1586/14789450.2.5.649.

* cited by examiner

Structure and Receptor Affinity for High Mannose and Phosphorylated Oligosaccharides Mannose 6-phrosphate (M6P)

Structure and Binding Domains of the CIMPR

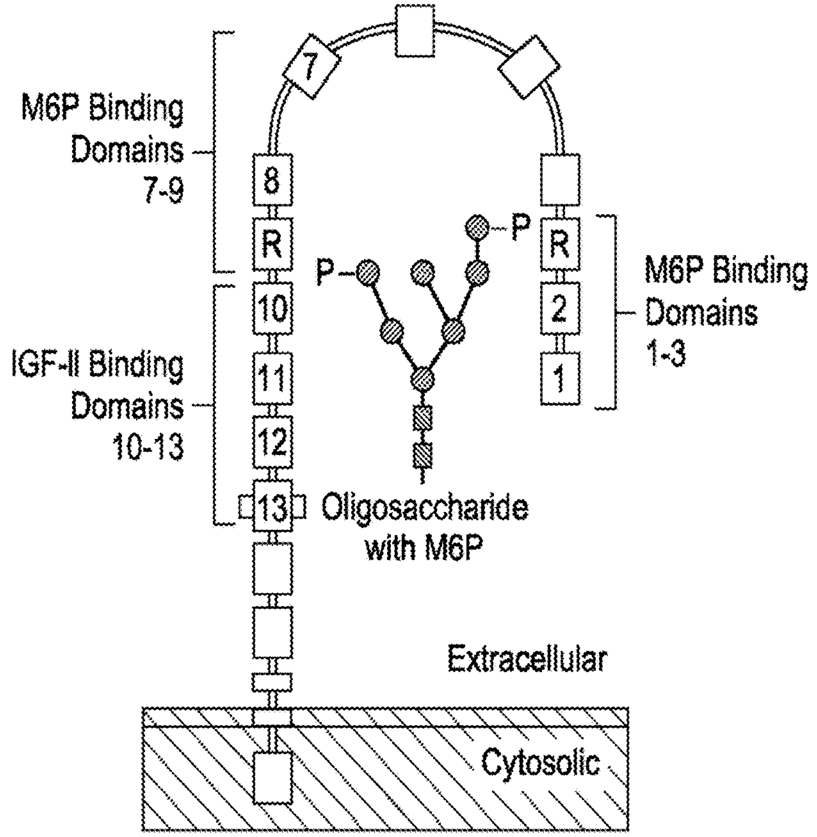

*Fig. 3A*

Ligands; Affinity and In Vivo Location of Three Glycoprotein Receptors

| Ligand | Receptor | Affinity (nmolar) | Location |
|---|---|---|---|
| Bis-Phosphoylated Glycan | CIMPR | 2 | All Cells |
| Mono-Phosphorylated Glycan | | 7,000 | |
| High Mannose Glycan | Mannose Receptor | 20[b] | Macrophages Dendritic Cells |
| De-sialylated Complex Glycan | Asialyoglycoprotein Receptor | 7[c] | Hepatocytes |

Reference: [a]Tong *et al* 1989; [b]Taylor *et al* 1992; [c]Schwartz *et al* 1981

*Fig. 3B*

ATB200 Vector Construction

- Host Cell: DG44
- Vector: pOptivec-110
  - Invitrogen vector
  - 952 aa, native signal peptide
- Screening Pressure: -HT, 500nM MTX Distribution of N-Glycans on rhGAA Preparations

| | Lumizyme | BP-rhGAA* | ATB200 | |
|---|---|---|---|---|
| | | | 1 | 2 |
| *Complex Type N-Glycans* | 70.7% | 48.9% | 51.0% | 47.5% |
| *Hybrid Type N-Glycans* | 6.7% | 9.7% | 4.4% | 3.7% |
| *High Mannose Type N-Glycans:* | | | | |
| *Non-phosphorylated* | 15.8% | 23.7% | 14.0% | 9.9% |
| *Mono-M6P* | 5.2% | 10.4% | 13.4% | 14.2% |
| *Bis-M6P* | **1.6%** | 6.8% | **17.2%** | **24.7%** |

FIG. 10

| Glycan | Alglucosidase Alfa (mol bis-glycan/ mol protein) | ATB200 (mol bis-glycan/ mol protein) |
|---|---|---|
| *Bis-M6P* | 0.1 | 1.3 |

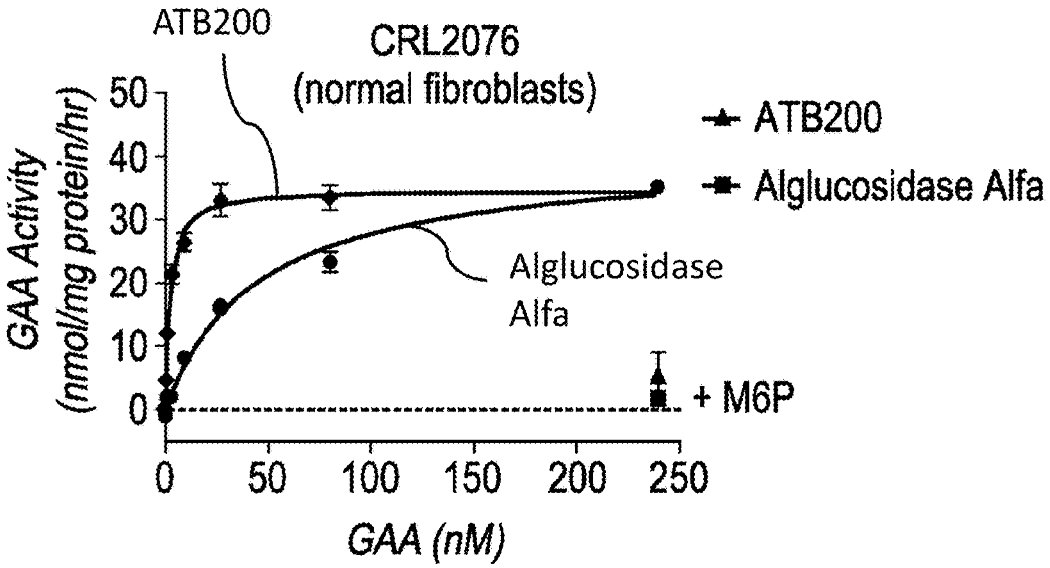
FIG. 13A
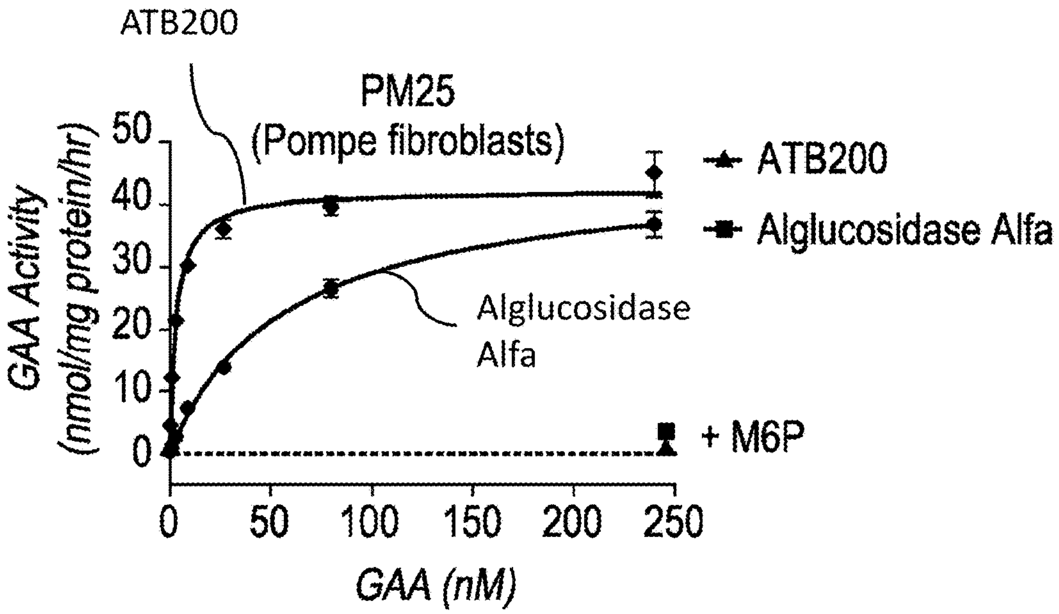
FIG. 13B
| Cell Line | $K_{uptake}$ (nM) | |
|---|---|---|
| | AT200 | Lumizyme |
| normal | 2 | 56 |
| Pompe | 3 | 57 |
FIG. 13C

| Comparison of % glycogen reduction in *Gaa* KO mice after Lumizyme or ATB200 administration (with or without miglustat) | | |
|---|---|---|
| Enzyme ± Chaperone | Quadriceps | Triceps |
| Lumizyme alone (20 mg/kg) | 14 | 14 |
| ATB200 alone (20 mg/kg) | 74 | 62 |
| ATB200 + Miglustat (20 mg/kg) + (10 mg/kg) | 94 | 73 |

SEQUENCE LISTING

```
Sequence total quantity: 2
SEQ ID NO: 1            moltype = AA  length = 952
FEATURE                 Location/Qualifiers
source                  1..952
                        mol_type = protein
                        organism = Homo sapiens
SEQUENCE: 1
MGVRHPPCSH RLLAVCALVS LATAALLGHI LLHDFLLVPR ELSGSSPVLE ETHPAHQQGA  60
SRPGPRDAQA HPGRPRAVPT QCDVPPNSRF DCAPDKAITQ EQCEARGCCY IPAKQGLQGA  120
QMGQPWCFFP PSYPSYKLEN LSSSEMGYTA TLTRTTPTFF PKDILTLRLD VMMETENRLH  180
FTIKDPANRR YEVPLETPRV HSRAPSPLYS VEFSEEPFGV IVHRQLDGRV LLNTTVAPLF  240
FADQFLQLST SLPSQYITGL AEHLSPLMLS TSWTRITLWN RDLAPTPGAN LYGSHPFYLA  300
LEDGGSAHGV FLLNSNAMDV VLQPSPALSW RSTGGILDVY IFLGPEPKSV VQQYLDVVGY  360
PFMPPYWGLG FHLCRWGYSS TAITRQVVEN MTRAHFPLDV QWNDLDYMDS RRDFTFNKDG  420
FRDFPAMVQE LHQGGRRYMM IVDPAISSSG PAGSYRPYDE GLRRGVFITN ETGQPLIGKV  480
WPGSTAFPDF TNPTALAWWE DMVAEFHDQV PFDGMWIDMN EPSNFIRGSE DGCPNNELEN  540
PPYVPGVVGG TLQAATICAS SHQFLSTHYN LHNLYGLTEA IASHRALVKA RGTRPFVISR  600
STFAGHGRYA GHWTGDVWSS WEQLASSVPE ILQFNLLGVP LVGADVCGFL GNTSEELCVR  660
WTQLGAFYPF MRNHNSLLSL PQEPYSFSEP AQQAMRKALT LRYALLPHLY TLFHQAHVAG  720
ETVARPLFLE FPKDSSTWTV DHQLLWGEAL LITPVLQAGK AEVTGYFPLG TWYDLQTVPI  780
EALGSLPPPP AAPREPAIHS EGQWVTLPAP LDTINVHLRA GYIIPLQGPG LTTTESRQQP  840
MALAVALTKG GEARGELFWD DGESLEVLER GAYTQVIFLA RNNTIVNELV RVTSEGAGLQ  900
LQKVTVLGVA TAPQQVLSNG VPVSNFTYSP DTKVLDICVS LLMGEQFLVS WC          952

SEQ ID NO: 2            moltype = AA  length = 896
FEATURE                 Location/Qualifiers
source                  1..896
                        mol_type = protein
                        organism = Homo sapiens
SEQUENCE: 2
QQGASRPGPR DAQAHPGRPR AVPTQCDVPP NSRFDCAPDK AITQEQCEAR GCCYIPAKQG  60
LQGAQMGQPW CFFPPSYPSY KLENLSSSEM GYTATLTRTT PTFFPKDILT LRLDVMMETE  120
NRLHFTIKDP ANRRYEVPLE TPRVHSRAPS PLYSVEFSEE PFGVIVHRQL DGRVLLNTTV  180
APLFFADQFL QLSTSLPSQY ITGLAEHLSP LMLSTSWTRI TLWNRDLAPT PGANLYGSHP  240
FYLALEDGGS AHGVFLLNSN AMDVVLQPSP ALSWRSTGGI LDVYIFLGPE PKSVVQQYLD  300
VVGYPFMPPY WGLGFHLCRW GYSSTAITRQ VVENMTRAHF PLDVQWNDLD YMDSRRDFTF  360
NKDGFRDFPA MVQELHQGGR RYMMIVDPAI SSSGPAGSYR PYDEGLRRGV FITNETGQPL  420
IGKVWPGSTA FPDFTNPTAL AWWEDMVAEF HDQVPFDGMW IDMNEPSNFI RGSEDGCPNN  480
ELENPPYVPG VVGGTLQAAT ICASSHQFLS THYNLHNLYG LTEAIASHRA LVKARGTRPF  540
VISRSTFAGH GRYAGHWTGD VWSSWEQLAS SVPEILQFNL LGVPLVGADV CGFLGNTSEE  600
LCVRWTQLGA FYPFMRNHNS LLSLPQEPYS FSEPAQQAMR KALTLRYALL PHLYTLFHQA  660
HVAGETVARP LFLEFPKDSS TWTVDHQLLW GEALLITPVL QAGKAEVTGY FPLGTWYDLQ  720
TVPIEALGSL PPPPAAPREP AIHSEGQWVT LPAPLDTINV HLRAGYIIPL QGPGLTTTES  780
RQQPMALAVA LTKGGEARGE LFWDDGESLE VLERGAYTQV IFLARNNTIV NELVRVTSEG  840
AGLQLQKVTV LGVATAPQQV LSNGVPVSNF TYSPDTKVLD ICVSLLMGEQ FLVSWC      896
```

METHOD FOR SELECTION OF HIGH M6P RECOMBINANT PROTEINS

CROSS-REFERENCE TO RELATED APPLICATIONS

This application is a continuation of U.S. patent application Ser. No. 16/252,519, filed Jan. 18, 2019, which is a continuation of U.S. patent application Ser. No. 15/473,994, filed Mar. 30, 2017, which claims the benefit of U.S. Provisional Application No. 62/315,400, filed Mar. 30, 2016, and U.S. Provisional Application No. 62/457,584, filed Feb. 10, 2017, the entire contents of which are incorporated herein by reference in their entirety.

TECHNICAL FIELD

Principles and embodiments of the present invention relate generally to the manufacturing of recombinant proteins, particularly lysosomal enzymes that have a high content of mannose-6-phosphate.

BACKGROUND

Lysosomal storage disorders are a group of autosomal recessive genetic diseases characterized by the accumulation of cellular glycosphingolipids, glycogen, or mucopolysaccharides within intracellular compartments called lysosomes. Individuals with these diseases carry mutant genes coding for enzymes which are defective in catalyzing the hydrolysis of one or more of these substances, which then build up in the lysosomes. For example, Pompe disease, also known as acid maltase deficiency or glycogen storage disease type II, is one of several lysosomal storage disorders. Other examples of lysosomal disorders include Gaucher disease, GM1-gangliosidosis, fucosidosis, mucopolysaccharidoses, Hurler-Scheie disease, Niemann-Pick A and B diseases, and Fabry disease. Pompe disease is also classified as a neuromuscular disease or a metabolic myopathy.

Pompe disease is estimated to occur in about 1 in 40,000 births, and is caused by a mutation in the GAA gene, which codes for the enzyme lysosomal α-glucosidase (EC: 3.2.1.20), also commonly known as acid α-glucosidase. Acid α-glucosidase is involved in the metabolism of glycogen, a branched polysaccharide which is the major storage form of glucose in animals, by catalyzing its hydrolysis into glucose within the lysosomes. Because individuals with Pompe disease produce mutant, defective acid α-glucosidase which is inactive or has reduced activity, glycogen breakdown occurs slowly or not at all, and glycogen accumulates in the lysosomes of various tissues, particularly in striated muscles, leading to a broad spectrum of clinical manifestations, including progressive muscle weakness and respiratory insufficiency. Tissues such as the heart and skeletal muscles are particularly affected.

Pompe disease can vary widely in the degree of enzyme deficiency, severity and age of onset, and over 500 different mutations in the GAA gene have been identified, many of which cause disease symptoms of varying severity. The disease has been classified into broad types: early onset or infantile and late onset. Earlier onset of disease and lower enzymatic activity are generally associated with a more severe clinical course. Infantile Pompe disease is the most severe, resulting from complete or near complete acid α-glucosidase deficiency, and presents with symptoms that include severe lack of muscle tone, weakness, enlarged liver and heart, and cardiomyopathy. The tongue may become enlarged and protrude, and swallowing may become difficult. Most affected children die from respiratory or cardiac complications before the age of two. Late onset Pompe disease can present at any age older than 12 months and is characterized by a lack of cardiac involvement and better short-term prognosis. Symptoms are related to progressive skeletal muscle dysfunction, and involve generalized muscle weakness and wasting of respiratory muscles in the trunk, proximal lower limbs, and diaphragm. Some adult patients are devoid of major symptoms or motor limitations. Prognosis generally depends on the extent of respiratory muscle involvement. Most subjects with Pompe disease eventually progress to physical debilitation requiring the use of a wheelchair and assisted ventilation, with premature death often occurring due to respiratory failure.

Recent treatment options for Pompe disease include enzyme replacement therapy (ERT) with recombinant human acid α-glucosidase (rhGAA). Conventional rhGAA products are known under the names alglucosidase alfa, Myozyme® or Lumizyme®, from Genzyme, Inc. ERT is a chronic treatment required throughout the lifetime of the patient, and involves administering the replacement enzyme by intravenous infusion. The replacement enzyme is then transported in the circulation and enters lysosomes within cells, where it acts to break down the accumulated glycogen, compensating for the deficient activity of the endogenous defective mutant enzyme, and thus relieving the disease symptoms. In subjects with infantile onset Pompe disease, treatment with alglucosidase alfa has been shown to significantly improve survival compared to historical controls, and in late onset Pompe disease, alglucosidase alfa has been shown to have a statistically significant, if modest, effect on the 6-Minute Walk Test (6MWT) and forced vital capacity (FVC) compared to placebo.

However, the majority of subjects either remain stable or continue to deteriorate while undergoing treatment with alglucosidase alfa. The reason for the apparent sub-optimal effect of ERT with alglucosidase alfa is unclear, but could be partly due to the progressive nature of underlying muscle pathology, or the poor tissue targeting of the current ERT. For example, the infused enzyme is not stable at neutral pH, including at the pH of plasma (about pH 7.4), and can be irreversibly inactivated within the circulation. Furthermore, infused alglucosidase alfa shows insufficient uptake in key disease-relevant muscles, possibly due to inadequate glycosylation with mannose-6-phosphate (M6P) residues. Such residues bind cation-independent mannose-6-phosphate receptors (CIMPR) at the cell surface, allowing the enzyme to enter the cell and the lysosomes within. Therefore, high doses of the enzyme may be required for effective treatment so that an adequate amount of active enzyme can reach the lysosomes, making the therapy costly and time-consuming.

There are seven potential N-linked glycosylation sites on rhGAA. Since each glycosylation site is heterogeneous in the type of N-linked oligosaccharides (N-glycans) present, rhGAA consist of a complex mixture of proteins with N-glycans having varying binding affinities for M6P receptor and other carbohydrate receptors. rhGAA that contains a high mannose N-glycans having one M6P group (mono-M6P) binds to CIMPR with low (~6,000 nM) affinity while rhGAA that contains two M6P groups on same N-glycan (bis-M6P) bind with high (~2 nM) affinity. Representative structures for non-phosphorylated, mono-M6P, and bis-M6P glycans are shown by FIG. 1A. The mannose-6-P group is shown by FIG. 1B. Once inside the lysosome, rhGAA can enzymatically degrade accumulated glycogen. However, conventional rhGAAs have low total levels of M6P- and bis-M6P bearing glycans and, thus, target muscle cells poorly resulting in inferior delivery of rhGAA to the lysosomes. Productive drug targeting of rhGAA is shown in FIG. 2A. The majority of rhGAA molecules in these conventional products do not have phosphorylated N-glycans, thereby lacking affinity for the CIMPR. Non-phosphorylated high mannose glycans can also be cleared by the mannose receptor which results in non-productive clearance of the ERT (FIG. 2B).

The other type of N-glycans, complex carbohydrates, which contain galactose and sialic acids, are also present on rhGAA. Since complex N-glycans are not phosphorylated they have no affinity for CIMPR. However, complex-type N-glycans with exposed galactose residues have moderate to high affinity for the asialoglycoprotein receptor on liver hepatocytes which leads to rapid non-productive clearance of rhGAA (FIG. 2B).

Current manufacturing processes used to make conventional rhGAA, such as Myozyme®, Lumizyme® or alglucosidase alfa, have not significantly increased the content of M6P or bis-M6P because cellular carbohydrate processing is naturally complex and extremely difficult to manipulate. Accordingly, there remains a need for further improvements to enzyme replacement therapy for treatment of Pompe disease, such as new manufacturing, capturing and purification processes for rhGAA.

Similarly, other recombinant proteins that are targeted to the lysosome, such as other lysosomal enzymes, also bind CIMPR. However, current manufacturing processes used to make other conventional recombinant proteins that are targeted to lysosomes do not provide recombinant proteins with a high content of M6P or bis-M6P. Accordingly, there remains a need for further improvements in the manufacturing, capturing and purification processes for these other recombinant proteins as well.

SUMMARY

One aspect of the present invention is related to a method for producing recombinant human lysosomal proteins. In various embodiments of this aspect, the method comprises culturing host cells in a bioreactor that secrete a recombinant human lysosomal protein, removing media from the bioreactor, filtering the media to provide a filtrate, loading the filtrate onto an anion exchange chromatography (AEX) column to capture the lysosomal protein and eluting a first protein product from the AEX column.

In one or more embodiments, the recombinant human lysosomal protein is recombinant human α-glucosidase (rhGAA). In one or more embodiments, the rhGAA comprises an amino acid sequence that is at least 95% identical to SEQ ID NO: 2.

In one or more embodiments, the method further comprises loading the first protein product onto a chromatography column, and eluting a second protein product from the column. In some embodiments, the column is an immobilized metal affinity chromatography (IMAC) column In one or more embodiments, the method further comprises loading the second protein product onto a chromatography column, and eluting a third protein product from the chromatography column. In some embodiments, the third chromatography column is selected from a cation exchange chromatography (CEX) column and a size exclusion chromatography (SEC) column.

In one or more embodiments, filtering the media is selected from alternating tangential flow filtration (ATF) and tangential flow filtration (TFF).

In one or more embodiments, the method further comprises inactivating viruses in one or more of the first protein product, the second protein product and the third protein product.

In one or more embodiments, the method further comprises filtering the second protein product or the third protein product to provide a filtered product and filling a vial with the filtered product. In one or more embodiments, the method further comprises lyophilizing the filtered product.

In one or more embodiments, the host cells comprise Chinese hamster ovary (CHO) cells. In some embodiments, the host cells comprise CHO cell line GA-ATB-200 or ATB-200-X5-14 or a subculture thereof.

In one or more embodiments, (i) at least 90% of the first protein product or the second protein product or the third protein product binds to cation-independent manose-6-phosphate receptor (CIMPR) or (ii) at least 90% of the first protein product or the second protein product or the third protein product contains an N-glycan carrying mono-mannose-6-phosphate (mono-M6P) or bis-mannose-6-phosphate (bis-M6P).

In one or more embodiments, the recombinant human lysosomal protein is rhGAA comprising seven potential N-glycosylation sites, at least 50% of molecules of the rhGAA comprise an N-glycan unit bearing two mannose-6-phosphate residues at the first site, at least 30% of molecules of the rhGAA comprise an N-glycan unit bearing one mannose-6-phosphate residue at the second site, at least 30% of molecules of the rhGAA comprise an N-glycan unit bearing two mannose-6-phosphate residue at the fourth site, and at least 20% of molecules of the rhGAA comprise an N-glycan unit bearing one mannose-6-phosphate residue at the fourth site.

Another aspect of the present invention is related to a recombinant protein product made by any of the methods described herein.

Another aspect of the present invention is related to pharmaceutical composition comprising the recombinant protein product and a pharmaceutically acceptable carrier.

Yet another aspect of the present invention is related to a method for treating a lysosomal storage disorder, the method comprising administering the pharmaceutical composition to a patient in need thereof.

In one or more embodiments, the lysosomal storage disorder is Pompe disease and the recombinant protein is rhGAA. In one or more embodiments, the patient is co-administered a pharmacological chaperone for a-glucosidase within 4 hours of the administration of the pharmaceutical composition comprising the rhGAA product. In some embodiments, the pharmacological chaperone is selected from 1-deoxynojirimycin and N-butyl-deoxynojirimycin. In some embodiments, the pharmacological chaperone is co-formulated with the rhGAA product.

Various embodiments are listed below. It will be understood that the embodiments listed below may be combined not only as listed below, but in other suitable combinations in accordance with the scope of the invention.

BRIEF DESCRIPTION OF THE DRAWINGS

Further features of the present invention will become apparent from the following written description and the accompanying figures, in which:

FIG. 3A graphically depicts a CIMPR receptor (also known as an IGF2 receptor) and domains of this receptor.

FIG. 3B is a table showing binding affinity (nmolar) of glycans bearing bis- and mono-M6P for CIMPR, the binding affinity of high mannose-type glycans to mannose receptors, and the binding affinity of desialylated complex glycan for asialyoglycoprotein receptors. RhGAA that has glycans bearing M6P and bis-M6P can productively bind to CIMPR on muscle.

As shown in FIG. 2A, 78% of the GAA activity in Lumizyme® eluted prior to addition of M6P. FIG. 2B shows that 73% of the GAA Myozyme® activity eluted prior to addition of M6P. Only 22% or 27% of the rhGAA in Lumizyme® or Myozyme®, respectively, was eluted with M6P. These figures show that most of the rhGAA in these two conventional rhGAA products lack glycans having M6P needed to target CIMPR in target muscle tissues.

FIG. 10 is a table showing a summary of N-glycan structures of Lumizyme® compared to three different preparations of ATB200 rhGAA, identified as BP-rhGAA, ATB200-1 and ATB200-2.

FIG. 13A is a graph comparing ATB200 rhGAA activity (left trace) with Lumizyme® rhGAA activity (right trace) inside normal fibroblasts at various GAA concentrations.

FIG. 13B is a table comparing ATB200 rhGAA activity (left trace) with Lumizyme® rhGAA activity (right trace) inside fibroblasts from a subject having Pompe Disease at various GAA concentrations.

FIG. 13C is a table comparing $K_{uptake}$ of fibroblasts from normal subjects and subjects with Pompe Disease.

DETAILED DESCRIPTION

Figure 1A:
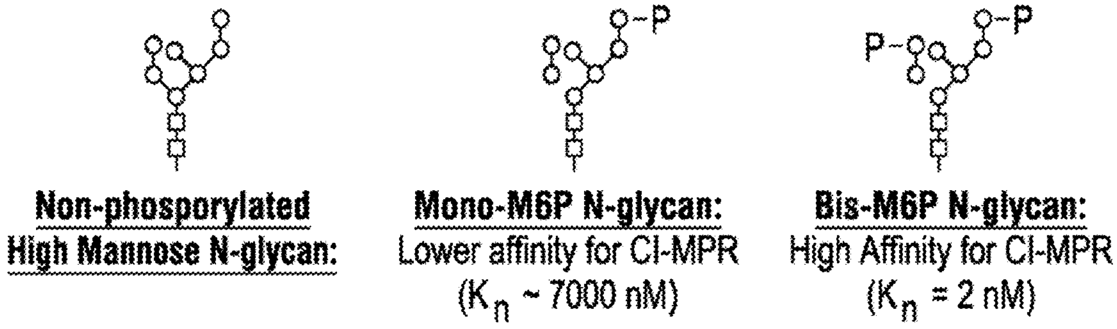
FIG. 1A shows non-phosphorylated high mannose glycan, a mono-M6P glycan, and a bis-M6P glycan.
Figure 1B:
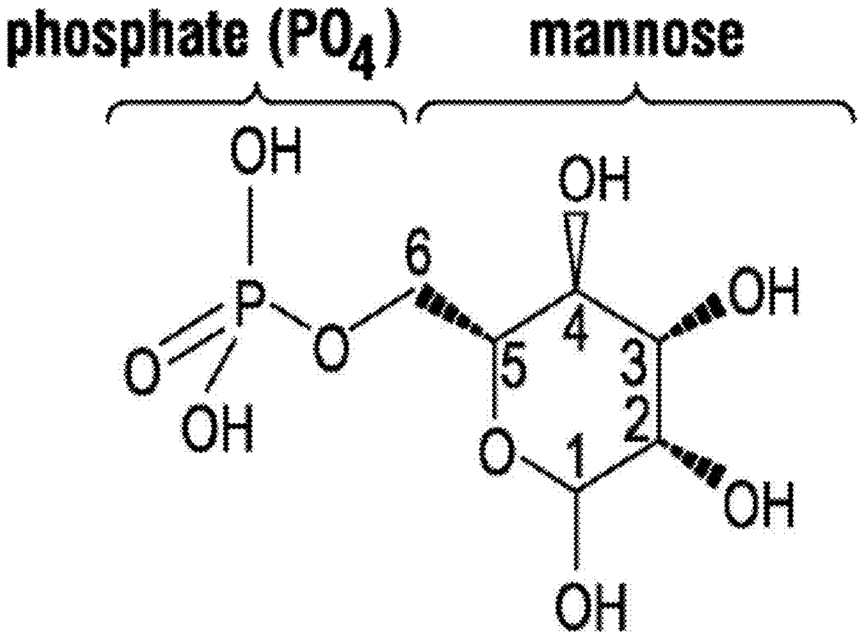
FIG. 1B shows the chemical structure of the M6P group.
Figures 2A, 2B:
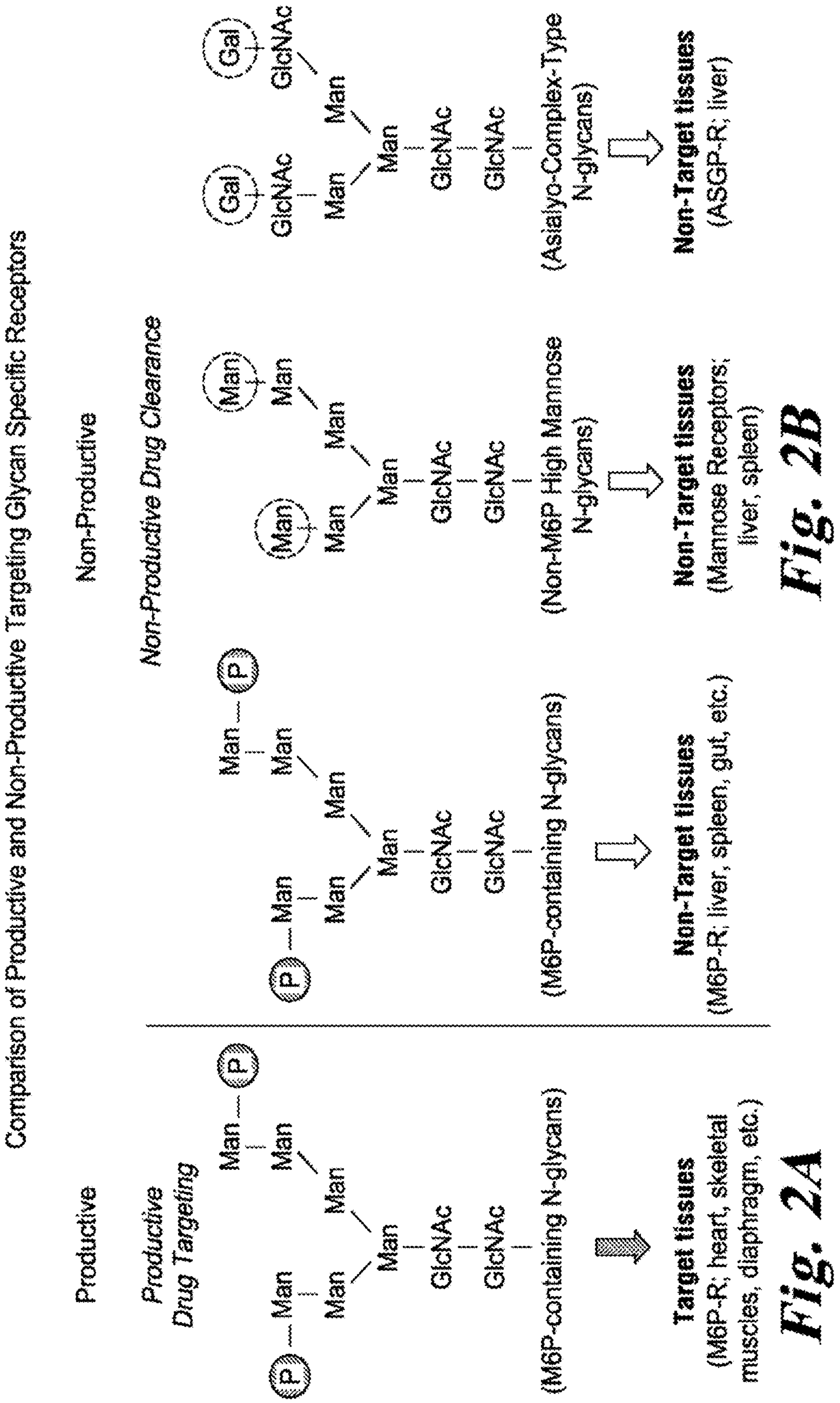
FIG. 2A describes productive targeting of rhGAA via glycans bearing M6P to target tissues (e.g. muscle tissues of subject with Pompe Disease).
FIG. 2B describes non-productive drug clearance to non-target tissues (e.g. liver and spleen) or by binding of non-M6P glycans to non-target tissues.

Before describing several exemplary embodiments of the invention, it is to be understood that the invention is not limited to the details of construction or process steps set forth in the following description. The invention is capable of other embodiments and of being practiced or being carried out in various ways.

Although specific reference is made to GAA, it will be understood by a person having ordinary skill in the art that the methods described herein may be used to produce, capture and purify other recombinant proteins that target the lysosome, including but not limited to the lysosomal enzyme a-galactosidase A.

Various aspects of the invention pertain to new methods for the production, capturing and purification of recombinant human lysosomal proteins, such as recombinant human acid α-glucosidase (rhGAA). Other aspects of the invention pertain to recombinant proteins produced by the processes described herein, as well as pharmaceutical compositions, methods of treatment, and uses of such recombinant proteins.

Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

In the present specification, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

As used herein, the term "lysosomal protein" refers to any protein that is targeted to the lysosome, such as a lysosomal enzyme. Examples of lysosomal enzymes and the associated disease are provided in Table 1 below:

TABLE 1

| Lysosomal Enzyme | Disease |
|---|---|
| Acid α-glucosidase | Pompe disease |
| α-galactosidase A | Fabry disease |
| Acid β-glucosidase | Gaucher disease |
| α-L-iduronidase | Hurler-Scheie disease |
| Iduronate sulfatase | Hunter disease |
| β-galactosidase | GM1-gangliosidosis; Morquio disease B |
| β-glucuronidase | Sly disease (MPS VI) |
| α-fucosidase | Fucosidosis |
| Acid sphingomyelinase | Niemann-Pick A and B |
| β-hexosaminidase A | Tay Sachs disease |
| β-hexosaminidase B | Sandhoff disease |
| β-galactocerebrosidase | Krabbe disease |
| Acid ceramidase | Farber disease |
| Heparan-N-sulfatase | Sanfilippo disease A (MPS IIIa) |
| α-N-acetyl-glucosaminidase | Sanfilippo disease B (MPS IIIb) |
| α-glucosaminide N-acetyltransferase | Sanfilippo disease C (MPS IIIc) |
| N-acetylglucosamine-6-sulfate sulfatase | Sanfilippo disease D (MPS IIId) |
| N-acetylgalactosamine-6-sulfate sulfatase | Morquio disease A (MPS Ivb) |
| Arylsulfatase A | Metachromatic leukodystrophy |
| Arylsulfatase B | Maroteaux-Lamy (MPS VI) |
| Acid lipase | Wolf disease |
| acid α-mannosidase | α-mannosidosis |
| acid β-mannosidase | β-mannosidosis |
| α-N-acetyl-neuraminidase | Sialidosis |
| α-N-acetylgalactosaminidase | Schindler-Kanzaki disease |
| N-aspartyl-β-glucosaminidase | Aspartylglucosaminuria |

As used herein, the term "Pompe disease," also referred to as acid maltase deficiency, glycogen storage disease type II (GSDII), and glycogenosis type II, is intended to refer to a genetic lysosomal storage disorder characterized by mutations in the GAA gene, which codes for the human acid α-glucosidase enzyme. The term includes but is not limited to early and late onset forms of the disease, including but not limited to infantile, juvenile and adult-onset Pompe disease.

As used herein, the term "acid α-glucosidase" is intended to refer to a lysosomal enzyme which hydrolyzes α-1,4 linkages between the D-glucose units of glycogen, maltose, and isomaltose. Alternative names include but are not limited to lysosomal α-glucosidase (EC:3.2.1.20); glucoamylase; 1,4-α-D-glucan glucohydrolase; amyloglucosidase; gamma-amylase and exo-1,4-α-glucosidase. Human acid α-glucosidase is encoded by the GAA gene (National Centre for Biotechnology Information (NCBI) Gene ID 2548), which has been mapped to the long arm of chromosome 17 (location 17q25.2-q25.3). More than 500 mutations have currently been identified in the human GAA gene, many of which are associated with Pompe disease. Mutations resulting in misfolding or misprocessing of the acid α-glucosidase enzyme include T1064C (Leu355Pro) and C2104T (Arg702Cys). In addition, GAA mutations which affect maturation and processing of the enzyme include Leu405Pro and Met519Thr. The conserved hexapeptide WIDMNE at amino acid residues 516-521 is required for activity of the acid α-glucosidase protein. As used herein, the abbreviation "GAA" is intended to refer to the acid α-glucosidase enzyme, while the italicized abbreviation "*GAA*" is intended to refer to the human gene coding for the human acid α-glucosidase enzyme The italicized abbreviation "*Gaa*" is intended to refer to non-human genes coding for non-human acid α-glucosidase enzymes, including but not limited to rat or mouse genes, and the abbreviation "Gaa" is intended to refer to non-human acid α-glucosidase enzymes. Thus, the abbreviation "rhGAA" is intended to refer to the recombinant human acid α-glucosidase enzyme.

As used herein, the term "alglucosidase alfa" is intended to refer to a recombinant human acid α-glucosidase identified as [199-arginine,223-histidine]prepro-α-glucosidase (human); Chemical Abstracts Registry Number 420794-05-0. Alglucosidase alfa is approved for marketing in the United States by Genzyme, as of January 2016, as the products Lumizyme® and Myozyme®.

As used herein, the term "ATB200" is intended to refer to a recombinant human acid α-glucosidase described in co-pending patent application PCT/US2015/053252, the disclosure of which is herein incorporated by reference.

As used herein, the term "glycan" is intended to refer to a polysaccharide chain covalently bound to an amino acid residue on a protein or polypeptide. As used herein, the term "N-glycan" or "N-linked glycan" is intended to refer to a polysaccharide chain attached to an amino acid residue on a protein or polypeptide through covalent binding to a nitrogen atom of the amino acid residue. For example, an N-glycan can be covalently bound to the side chain nitrogen atom of an asparagine residue. Glycans can contain one or several monosaccharide units, and the monosaccharide units can be covalently linked to form a straight chain or a branched chain. In at least one embodiment, N-glycan units attached to ATB200 can comprise one or more monosaccharide units each independently selected from N-acetylglucosamine, mannose, galactose or sialic acid. The N-glycan units on the protein can be determined by any appropriate analytical technique, such as mass spectrometry. In some embodiments, the N-glycan units can be determined by liquid chromatography-tandem mass spectrometry (LC-MS/MS) utilizing an instrument such as the Thermo Scientific Orbitrap Velos Pro™ Mass Spectrometer, Thermo Scientific Orbitrap Fusion Lumos Tribid™ Mass Spectrometer or Waters Xevo® G2-XS QTof Mass Spectrometer.

As used herein, the term "high-mannose N-glycan" is intended to refer to an N-glycan having one to six or more mannose units. In at least one embodiment, a high mannose N-glycan unit can contain a bis(N-acetylglucosamine) chain bonded to an asparagine residue and further bonded to a branched polymannose chain. As used herein interchangeably, the term "M6P" or "mannose-6-phosphate" is intended to refer to a mannose unit phosphorylated at the 6 position; i.e. having a phosphate group bonded to the hydroxyl group at the 6 position. In at least one embodiment, one or more mannose units of one or more N-glycan units are phosphorylated at the 6 position to form mannose-6-phosphate units. In at least one embodiment, the term "M6P" or "mannose-6-phosphate" refers to both a mannose phosphodiester having N-acetylglucosamine (GlcNAc) as a "cap" on the phosphate group, as well as a mannose unit having an exposed phosphate group lacking the GlcNAc cap. In at least one embodiment, the N-glycans of a protein can have multiple M6P groups, with at least one M6P group having a GlcNAc cap and at least one other M6P group lacking a GlcNAc cap.

As used herein, the term "complex N-glycan" is intended to refer to an N-glycan containing one or more galactose and/or sialic acid units. In at least one embodiment, a complex N-glycan can be a high-mannose N-glycan in which one or mannose units are further bonded to one or more monosaccharide units each independently selected from N-acetylglucosamine, galactose and sialic acid.

As used herein, the compound miglustat, also known as N-butyl-1-deoxynojirimycin NB-DNJ or (2R,3R,4R,5S)-1-butyl-2-(hydroxymethyl)piperidine-3,4,5-triol, is a compound having the following chemical formula:

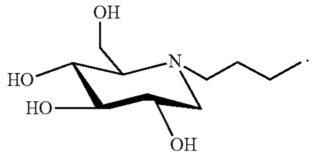

One formulation of miglustat is marketed commercially under the trade name Zavesca® as monotherapy for type 1 Gaucher disease.

As discussed below, pharmaceutically acceptable salts of miglustat may also be used in the present invention. When a salt of miglustat is used, the dosage of the salt will be adjusted so that the dose of miglustat received by the patient is equivalent to the amount which would have been received had the miglustat free base been used.

As used herein, the compound duvoglustat, also known as 1-deoxynojirimycin or DNJ or (2R,3R,4R,5S)-2-(hydroxymethyl)piperidine-3,4,5-triol, is a compound having the following chemical formula:

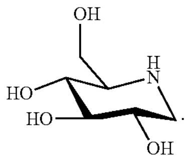

When a salt of duvoglustat is used, the dosage of the salt will be adjusted so that the dose of duvoglustat received by the patient is equivalent to the amount which would have been received had the duvoglustat free base been used.

As used herein, the term "pharmacological chaperone" or sometimes simply the term "chaperone" is intended to refer to a molecule that specifically binds to a lysosomal protein and has one or more of the following effects:

- enhances the formation of a stable molecular conformation of the protein;
- enhances proper trafficking of the protein from the endoplasmic reticulum to another cellular location, preferably a native cellular location, so as to prevent endoplasmic reticulum-associated degradation of the protein;
- prevents aggregation of conformationally unstable or misfolded proteins;
- restores and/or enhances at least partial wild-type function, stability, and/or activity of the protein; and/or
- improves the phenotype or function of the cell harboring the protein.

Thus, a pharmacological chaperone for acid α-glucosidase is a molecule that binds to acid α-glucosidase, resulting in proper folding, trafficking, non-aggregation, and activity of acid α-glucosidase. As used herein, this term includes but is not limited to active site-specific chaperones (ASSCs) which bind in the active site of the enzyme, inhibitors or antagonists, and agonists. In at least one embodiment, the pharmacological chaperone can be an inhibitor or antagonist of acid α-glucosidase. As used herein, the term "antagonist" is intended to refer to any molecule that binds to acid α-glucosidase and either partially or completely blocks, inhibits, reduces, or neutralizes an activity of acid α-glucosidase. In at least one embodiment, the pharmacological chaperone is miglustat. Another non-limiting example of a pharmacological chaperone for acid α-glucosidase is duvoglustat.

As used herein, the term "active site" is intended to refer to a region of a protein that is associated with and necessary for a specific biological activity of the protein. In at least one embodiment, the active site can be a site that binds a substrate or other binding partner and contributes the amino acid residues that directly participate in the making and breaking of chemical bonds.

As used herein, the "therapeutically effective dose" and "effective amount" are intended to refer to an amount of recombinant human lysosomal protein (e.g. rhGAA) and/or of chaperone and/or of a combination thereof, which is sufficient to result in a therapeutic response in a subject. A therapeutic response may be any response that a user (for example, a clinician) will recognize as an effective response to the therapy, including any surrogate clinical markers or symptoms described herein and known in the art. Thus, in at least one embodiment, a therapeutic response can be an amelioration or inhibition of one or more symptoms or markers of Pompe disease such as those known in the art. Symptoms or markers of Pompe disease include but are not limited to decreased acid α-glucosidase tissue activity; cardiomyopathy; cardiomegaly; progressive muscle weakness, especially in the trunk or lower limbs; profound hypotonia; macroglossia (and in some cases, protrusion of the tongue); difficulty swallowing, sucking, and/or feeding; respiratory insufficiency; hepatomegaly (moderate); laxity of facial muscles; areflexia; exercise intolerance; exertional dyspnea; orthopnea; sleep apnea; morning headaches; somnolence; lordosis and/or scoliosis; decreased deep tendon reflexes; lower back pain; and failure to meet developmental motor milestones. It should be noted that a concentration of chaperone (e.g. miglustat) that has an inhibitory effect on acid α-glucosidase may constitute an "effective amount" for purposes of this invention because of dilution (and consequent shift in binding due to the change in equilibrium), bioavailability and metabolism of the chaperone upon administration in vivo.

As used herein, the term "enzyme replacement therapy" or "ERT" is intended to refer to the introduction of a non-native, purified enzyme into an individual having a deficiency in such enzyme. The administered protein can be obtained from natural sources or by recombinant expression. The term also refers to the introduction of a purified enzyme in an individual otherwise requiring or benefiting from administration of a purified enzyme. In at least one embodiment, such an individual suffers from enzyme insufficiency. The introduced enzyme may be a purified, recombinant enzyme produced in vitro, or a protein purified from isolated tissue or fluid, such as, for example, placenta or animal milk, or from plants.

As used herein, the term "combination therapy" is intended to refer to any therapy wherein two or more individual therapies are administered concurrently or consecutively. In at least one embodiment, the results of the combination therapy are enhanced as compared to the effect of each therapy when it is performed individually. Enhancement may include any improvement of the effect of the various therapies that may result in an advantageous result as compared to the results achieved by the therapies when performed alone. Enhanced effect or results can include a synergistic enhancement, wherein the enhanced effect is more than the additive effects of each therapy when performed by itself; an additive enhancement, wherein the enhanced effect is substantially equal to the additive effect of each therapy when performed by itself; or less than a synergistic effect, wherein the enhanced effect is lower than the additive effect of each therapy when performed by itself, but still better than the effect of each therapy when performed by itself. Enhanced effect may be measured by any means known in the art by which treatment efficacy or outcome can be measured.

As used herein, the term "pharmaceutically acceptable" is intended to refer to molecular entities and compositions that are physiologically tolerable and do not typically produce untoward reactions when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans.

As used herein, the term "carrier" is intended to refer to a diluent, adjuvant, excipient, or vehicle with which a compound is administered. Suitable pharmaceutical carriers are known in the art and, in at least one embodiment, are described in "Remington's Pharmaceutical Sciences" by E. W. Martin, 18th Edition, or other editions.

As used herein, the terms "subject" or "patient" are intended to refer to a human or non-human animal. In at least one embodiment, the subject is a mammal. In at least one embodiment, the subject is a human.

As used herein, the term "anti-drug antibody" is intended to refer to an antibody specifically binding to a drug administered to a subject and generated by the subject as at least part of a humoral immune response to administration of the drug to the subject. In at least one embodiment the drug is a therapeutic protein drug product. The presence of the anti-drug antibody in the subject can cause immune responses ranging from mild to severe, including but not limited to life-threatening immune responses which include but are not limited to anaphylaxis, cytokine release syndrome and cross-reactive neutralization of endogenous proteins mediating critical functions. In addition or alternatively, the presence of the anti-drug antibody in the subject can decrease the efficacy of the drug.

As used herein, the term "neutralizing antibody" is intended to refer to an anti-drug antibody acting to neutralize the function of the drug. In at least one embodiment, the therapeutic protein drug product is a counterpart of an endogenous protein for which expression is reduced or absent in the subject. In at least one embodiment, the neutralizing antibody can act to neutralize the function of the endogenous protein.

As used herein, the terms "about" and "approximately" are intended to refer to an acceptable degree of error for the quantity measured given the nature or precision of the measurements. For example, the degree of error can be indicated by the number of significant figures provided for the measurement, as is understood in the art, and includes but is not limited to a variation of ±1 in the most precise significant figure reported for the measurement. Typical exemplary degrees of error are within 20 percent (%), preferably within 10%, and more preferably within 5% of a given value or range of values. Alternatively, and particularly in biological systems, the terms "about" and "approximately" can mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The term "concurrently" as used herein is intended to mean at the same time as or within a reasonably short period of time before or after, as will be understood by those skilled in the art. For example, if two treatments are administered concurrently with each other, one treatment can be administered before or after the other treatment, to allow for time needed to prepare for the later of the two treatments. Therefore "concurrent administration" of two treatments includes but is not limited to one treatment following the other by 20 minutes or less, about 20 minutes, about 15 minutes, about 10 minutes, about 5 minutes, about 2 minutes, about 1 minute or less than 1 minute.

The term "pharmaceutically acceptable salt" as used herein is intended to mean a salt which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, for example, S. M. Birge et al., J. Pharm. Sci., 1977, 66, pp. 1-19, herein incorporated by reference.

The term "pharmaceutically-acceptable acid addition salt" as used herein is intended to mean those salts which retain the biological effectiveness and properties of the free bases and which are not biologically or otherwise undesirable, formed with inorganic acids including but not limited to hydrochloric acid, hydrobromic acid, sulfuric acid, sulfamic acid, nitric acid, phosphoric acid and the like, and organic acids including but not limited to acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid and the like.

The term "pharmaceutically-acceptable base addition salt" as used herein is intended to mean those salts which retain the biological effectiveness and properties of the free acids and which are not biologically or otherwise undesirable, formed with inorganic bases including but not limited to ammonia or the hydroxide, carbonate, or bicarbonate of ammonium or a metal cation such as sodium, potassium, lithium, calcium, magnesium, iron, zinc, copper, manganese, aluminum and the like. Salts derived from pharmaceutically-acceptable organic nontoxic bases include but are not limited to salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins and the like.

ATB200 rhGAA

In at least one embodiment, the recombinant human lysosomal protein (e.g. rhGAA) is expressed in Chinese hamster ovary (CHO) cells and comprises an increased content of N-glycan units bearing one or more mannose-6-phosphate residues when compared to a content of N-glycan units bearing one or more mannose-6-phosphate residues of a conventional recombinant human lysosomal protein such as alglucosidase alfa. In at least one embodiment, the acid α-glucosidase is a recombinant human acid α-glucosidase referred to herein as ATB200, as described in co-pending international patent application PCT/US2015/053252. ATB200 has been shown to bind cation-independent mannose-6-phosphate receptors (CIMPR) with high affinity ($K_D$~2-4 nM) and to be efficiently internalized by Pompe fibroblasts and skeletal muscle myoblasts ($K_{uptake}$~7-14 nM). ATB200 was characterized in vivo and shown to have a shorter apparent plasma half-life ($t_{1/2}$~45 min) than alglucosidase alfa ($t_{1/2}$~60 min).

In at least one embodiment, the recombinant human acid α-glucosidase is an enzyme having an amino acid sequence as set forth in SEQ ID NO: 1 or SEQ ID NO: 2.

SEQ ID NO: 1

```
Met Gly Val Arg His Pro Pro Cys Ser His Arg Leu Leu Ala Val Cys

Ala Leu Val Ser Leu Ala Thr Ala Ala Leu Leu Gly His Ile Leu Leu

His Asp Phe Leu Leu Val Pro Arg Glu Leu Ser Gly Ser Ser Pro Val

Leu Glu Glu Thr His Pro Ala His Gln Gln Gly Ala Ser Arg Pro Gly

Pro Arg Asp Ala Gln Ala His Pro Gly Arg Pro Arg Ala Val Pro Thr

Gln Cys Asp Val Pro Pro Asn Ser Arg Phe Asp Cys Ala Pro Asp Lys

Ala Ile Thr Gln Glu Gln Cys Glu Ala Arg Gly Cys Cys Tyr Ile Pro

Ala Lys Gln Gly Leu Gln Gly Ala Gln Met Gly Gln Pro Trp Cys Phe

Phe Pro Pro Ser Tyr Pro Ser Tyr Lys Leu Glu Asn Leu Ser Ser Ser

Glu Met Gly Tyr Thr Ala Thr Leu Thr Arg Thr Thr Pro Thr Phe Phe

Pro Lys Asp Ile Leu Thr Leu Arg Leu Asp Val Met Met Glu Thr Glu
```

-continued

Asn Arg Leu His Phe Thr Ile Lys Asp Pro Ala Asn Arg Arg Tyr Glu

Val Pro Leu Glu Thr Pro Arg Val His Ser Arg Ala Pro Ser Pro Leu

Tyr Ser Val Glu Phe Ser Glu Glu Pro Phe Gly Val Ile Val His Arg

Gln Leu Asp Gly Arg Val Leu Leu Asn Thr Thr Val Ala Pro Leu Phe

Phe Ala Asp Gln Phe Leu Gln Leu Ser Thr Ser Leu Pro Ser Gln Tyr

Ile Thr Gly Leu Ala Glu His Leu Ser Pro Leu Met Leu Ser Thr Ser

Trp Thr Arg Ile Thr Leu Trp Asn Arg Asp Leu Ala Pro Thr Pro Gly

Ala Asn Leu Tyr Gly Ser His Pro Phe Tyr Leu Ala Leu Glu Asp Gly

Gly Ser Ala His Gly Val Phe Leu Leu Asn Ser Asn Ala Met Asp Val

Val Leu Gln Pro Ser Pro Ala Leu Ser Trp Arg Ser Thr Gly Gly Ile

Leu Asp Val Tyr Ile Phe Leu Gly Pro Glu Pro Lys Ser Val Val Gln

Gln Tyr Leu Asp Val Val Gly Tyr Pro Phe Met Pro Pro Tyr Trp Gly

Leu Gly Phe His Leu Cys Arg Trp Gly Tyr Ser Ser Thr Ala Ile Thr

Arg Gln Val Val Glu Asn Met Thr Arg Ala His Phe Pro Leu Asp Val

Gln Trp Asn Asp Leu Asp Tyr Met Asp Ser Arg Arg Asp Phe Thr

Phe Asn Lys Asp Gly Phe Arg Asp Phe Pro Ala Met Val Gln Glu

Leu His Gln Gly Gly Arg Arg Tyr Met Met Ile Val Asp Pro Ala Ile

Ser Ser Ser Gly Pro Ala Gly Ser Tyr Arg Pro Tyr Asp Glu Gly Leu

Arg Arg Gly Val Phe Ile Thr Asn Glu Thr Gly Gln Pro Leu Ile Gly

Lys Val Trp Pro Gly Ser Thr Ala Phe Pro Asp Phe Thr Asn Pro Thr

Ala Leu Ala Trp Trp Glu Asp Met Val Ala Glu Phe His Asp Gln Val

Pro Phe Asp Gly Met Trp Ile Asp Met Asn Glu Pro Ser Asn Phe Ile

Arg Gly Ser Glu Asp Gly Cys Pro Asn Asn Glu Leu Glu Asn Pro Pro

Tyr Val Pro Gly Val Val Gly Gly Thr Leu Gln Ala Ala Thr Ile Cys

Ala Ser Ser His Gln Phe Leu Ser Thr His Tyr Asn Leu His Asn Leu

Tyr Gly Leu Thr Glu Ala Ile Ala Ser His Arg Ala Leu Val Lys Ala

Arg Gly Thr Arg Pro Phe Val Ile Ser Arg Ser Thr Phe Ala Gly His

Gly Arg Tyr Ala Gly His Trp Thr Gly Asp Val Trp Ser Ser Trp Glu

Gln Leu Ala Ser Ser Val Pro Glu Ile Leu Gln Phe Asn Leu Leu Gly

Val Pro Leu Val Gly Ala Asp Val Cys Gly Phe Leu Gly Asn Thr Ser

Glu Glu Leu Cys Val Arg Trp Thr Gln Leu Gly Ala Phe Tyr Pro Phe

Met Arg Asn His Asn Ser Leu Leu Ser Leu Pro Gln Glu Pro Tyr Ser

Phe Ser Glu Pro Ala Gln Gln Ala Met Arg Lys Ala Leu Thr Leu Arg

Tyr Ala Leu Leu Pro His Leu Tyr Thr Leu Phe His Gln Ala His Val

Ala Gly Glu Thr Val Ala Arg Pro Leu Phe Leu Glu Phe Pro Lys Asp

Ser Ser Thr Trp Thr Val Asp His Gln Leu Leu Trp Gly Glu Ala Leu

Leu Ile Thr Pro Val Leu Gln Ala Gly Lys Ala Glu Val Thr Gly Tyr

Phe Pro Leu Gly Thr Trp Tyr Asp Leu Gln Thr Val Pro Ile Glu Ala

Leu Gly Ser Leu Pro Pro Pro Pro Ala Ala Pro Arg Glu Pro Ala Ile

His Ser Glu Gly Gln Trp Val Thr Leu Pro Ala Pro Leu Asp Thr Ile

Asn Val His Leu Arg Ala Gly Tyr Ile Ile Pro Leu Gln Gly Pro Gly

-continued

Leu Thr Thr Thr Glu Ser Arg Gln Gln Pro Met Ala Leu Ala Val Ala

Leu Thr Lys Gly Gly Glu Ala Arg Gly Glu Leu Phe Trp Asp Asp Gly

Glu Ser Leu Glu Val Leu Glu Arg Gly Ala Tyr Thr Gln Val Ile Phe

Leu Ala Arg Asn Asn Thr Ile Val Asn Glu Leu Val Arg Val Thr Ser

Glu Gly Ala Gly Leu Gln Leu Gln Lys Val Thr Val Leu Gly Val Ala

Thr Ala Pro Gln Gln Val Leu Ser Asn Gly Val Pro Val Ser Asn Phe

Thr Tyr Ser Pro Asp Thr Lys Val Leu Asp Ile Cys Val Ser Leu Leu

Met Gly Glu Gln Phe Leu Val Ser Trp Cys

SEQ ID NO: 2

Gln Gln Gly Ala Ser Arg Pro Gly Pro Arg Asp Ala Gln Ala His Pro

Gly Arg Pro Arg Ala Val Pro Thr Gln Cys Asp Val Pro Pro Asn Ser

Arg Phe Asp Cys Ala Pro Asp Lys Ala Ile Thr Gln Glu Gln Cys Glu

Ala Arg Gly Cys Cys Tyr Ile Pro Ala Lys Gln Gly Leu Gln Gly Ala

Gln Met Gly Gln Pro Trp Cys Phe Phe Pro Pro Ser Tyr Pro Ser Tyr

Lys Leu Glu Asn Leu Ser Ser Ser Glu Met Gly Tyr Thr Ala Thr Leu

Thr Arg Thr Thr Pro Thr Phe Phe Pro Lys Asp Ile Leu Thr Leu Arg

Leu Asp Val Met Met Glu Thr Glu Asn Arg Leu His Phe Thr Ile Lys

Asp Pro Ala Asn Arg Arg Tyr Glu Val Pro Leu Glu Thr Pro Arg Val

His Ser Arg Ala Pro Ser Pro Leu Tyr Ser Val Glu Phe Ser Glu Glu

Pro Phe Gly Val Ile Val His Arg Gln Leu Asp Gly Arg Val Leu Leu

Asn Thr Thr Val Ala Pro Leu Phe Phe Ala Asp Gln Phe Leu Gln Leu

Ser Thr Ser Leu Pro Ser Gln Tyr Ile Thr Gly Leu Ala Glu His Leu

Ser Pro Leu Met Leu Ser Thr Ser Trp Thr Arg Ile Thr Leu Trp Asn

Arg Asp Leu Ala Pro Thr Pro Gly Ala Asn Leu Tyr Gly Ser His Pro

Phe Tyr Leu Ala Leu Glu Asp Gly Gly Ser Ala His Gly Val Phe Leu

Leu Asn Ser Asn Ala Met Asp Val Val Leu Gln Pro Ser Pro Ala Leu

Ser Trp Arg Ser Thr Gly Gly Ile Leu Asp Val Tyr Ile Phe Leu Gly

Pro Glu Pro Lys Ser Val Val Gln Gln Tyr Leu Asp Val Val Gly Tyr

Pro Phe Met Pro Pro Tyr Trp Gly Leu Gly Phe His Leu Cys Arg Trp

Gly Tyr Ser Ser Thr Ala Ile Thr Arg Gln Val Val Glu Asn Met Thr

Arg Ala His Phe Pro Leu Asp Val Gln Trp Asn Asp Leu Asp Tyr

Met Asp Ser Arg Arg Asp Phe Thr Phe Asn Lys Asp Gly Phe Arg

Asp Phe Pro Ala Met Val Gln Glu Leu His Gln Gly Gly Arg Arg Tyr

Met Met Ile Val Asp Pro Ala Ile Ser Ser Ser Gly Pro Ala Gly Ser Tyr

Arg Pro Tyr Asp Glu Gly Leu Arg Arg Gly Val Phe Ile Thr Asn Glu

Thr Gly Gln Pro Leu Ile Gly Lys Val Trp Pro Gly Ser Thr Ala Phe

Pro Asp Phe Thr Asn Pro Thr Ala Leu Ala Trp Trp Glu Asp Met Val

Ala Glu Phe His Asp Gln Val Pro Phe Asp Gly Met Trp Ile Asp Met

Asn Glu Pro Ser Asn Phe Ile Arg Gly Ser Glu Asp Gly Cys Pro Asn

Asn Glu Leu Glu Asn Pro Pro Tyr Val Pro Gly Val Val Gly Gly Thr

Leu Gln Ala Ala Thr Ile Cys Ala Ser Ser His Gln Phe Leu Ser Thr

-continued

His Tyr Asn Leu His Asn Leu Tyr Gly Leu Thr Glu Ala Ile Ala Ser

His Arg Ala Leu Val Lys Ala Arg Gly Thr Arg Pro Phe Val Ile Ser

Arg Ser Thr Phe Ala Gly His Gly Arg Tyr Ala Gly His Trp Thr Gly

Asp Val Trp Ser Ser Trp Glu Gln Leu Ala Ser Ser Val Pro Glu Ile

Leu Gln Phe Asn Leu Leu Gly Val Pro Leu Val Gly Ala Asp Val Cys

Gly Phe Leu Gly Asn Thr Ser Glu Glu Leu Cys Val Arg Trp Thr Gln

Leu Gly Ala Phe Tyr Pro Phe Met Arg Asn His Asn Ser Leu Leu Ser

Leu Pro Gln Glu Pro Tyr Ser Phe Ser Glu Pro Ala Gln Gln Ala Met

Arg Lys Ala Leu Thr Leu Arg Tyr Ala Leu Leu Pro His Leu Tyr Thr

Leu Phe His Gln Ala His Val Ala Gly Glu Thr Val Ala Arg Pro Leu

Phe Leu Glu Phe Pro Lys Asp Ser Ser Thr Trp Thr Val Asp His Gln

Leu Leu Trp Gly Glu Ala Leu Leu Ile Thr Pro Val Leu Gln Ala Gly

Lys Ala Glu Val Thr Gly Tyr Phe Pro Leu Gly Thr Trp Tyr Asp Leu

Gln Thr Val Pro Ile Glu Ala Leu Gly Ser Leu Pro Pro Pro Pro Ala

Ala Pro Arg Glu Pro Ala Ile His Ser Glu Gly Gln Trp Val Thr Leu

Pro Ala Pro Leu Asp Thr Ile Asn Val His Leu Arg Ala Gly Tyr Ile Ile

Pro Leu Gln Gly Pro Gly Leu Thr Thr Thr Glu Ser Arg Gln Gln Pro

Met Ala Leu Ala Val Ala Leu Thr Lys Gly Gly Glu Ala Arg Gly Glu

Leu Phe Trp Asp Asp Gly Glu Ser Leu Glu Val Leu Glu Arg Gly Ala

Tyr Thr Gln Val Ile Phe Leu Ala Arg Asn Asn Thr Ile Val Asn Glu

Leu Val Arg Val Thr Ser Glu Gly Ala Gly Leu Gln Leu Gln Lys Val

Thr Val Leu Gly Val Ala Thr Ala Pro Gln Gln Val Leu Ser Asn Gly

Val Pro Val Ser Asn Phe Thr Tyr Ser Pro Asp Thr Lys Val Leu Asp

Ile Cys Val Ser Leu Leu Met Gly Glu Gln Phe Leu Val Ser Trp Cys

In at least one embodiment, the recombinant human acid α-glucosidase has a wild-type GAA amino acid sequence as set forth in SEQ ID NO: 1, as described in U.S. Pat. No. 8,592,362 and has GenBank accession number AHE24104.1 (GI:568760974). In at least one embodiment, the recombinant human acid α-glucosidase is glucosidase alfa, the human acid α-glucosidase enzyme encoded by the most predominant of nine observed haplotypes of the GAA gene.

In at least one embodiment, the recombinant human acid α-glucosidase is initially expressed as having the full-length 952 amino acid sequence of wild-type GAA as set forth in SEQ ID NO: 1, and the recombinant human acid α-glucosidase undergoes intracellular processing that removes a portion of the amino acids, e.g. the first 56 amino acids. Accordingly, the recombinant human acid α-glucosidase that is secreted by the host cell can have a shorter amino acid sequence than the recombinant human acid α-glucosidase that is initially expressed within the cell. In at least one embodiment, the shorter protein can have the amino acid sequence set forth in SEQ ID NO: 2, which only differs from SEQ ID NO: 1 in that the first 56 amino acids comprising the signal peptide and precursor peptide have been removed, thus resulting in a protein having 896 amino acids. Other variations in the number of amino acids is also possible, such as having 1, 2, 3, 4, 5, 6, 7, 8, 9, 10, 11, 12, 13, 14, 15 or more deletions, substitutions and/or insertions relative to the amino acid sequence described by SEQ ID NO: 1 or SEQ ID NO: 2. In some embodiments, the rhGAA product includes a mixture of recombinant human acid α-glucosidase molecules having different amino acid lengths.

In at least one embodiment, the recombinant human acid α-glucosidase undergoes post-translational and/or chemical modifications at one or more amino acid residues in the protein. For example, methionine and tryptophan residues can undergo oxidation. As another example, the N-terminal glutamine can form pyro-glutamate. As another example, asparagine residues can undergo deamidation to aspartic acid. As yet another example, aspartic acid residues can undergo isomerization to iso-aspartic acid. As yet another example, unpaired cysteine residues in the protein can form disulfide bonds with free glutathione and/or cysteine. Accordingly, in some embodiments the enzyme is initially expressed as having an amino acid sequence as set forth in SEQ ID NO: 1 or SEQ ID NO: 2, and the enzyme undergoes one or more of these post-translational and/or chemical modifications. Such modifications are also within the scope of the present disclosure.

Polynucleotide sequences encoding GAA and such variant human GAAs are also contemplated and may be used to recombinantly express rhGAAs according to the invention.

Preferably, no more than 70, 65, 60, 55, 45, 40, 35, 30, 25, 20, 15, 10, or 5% of the total recombinant human lysosomal protein (e.g. rhGAA) molecules lack an N-glycan unit bearing one or more mannose-6-phosphate residues or lacks a capacity to bind to the cation independent mannose-6-phosphate receptor (CIMPR). Alternatively, 30, 35, 40, 45, 50, 55, 60, 65, 70, 75, 80, 85, 90, 95, 99%, <100% or more of the recombinant human lysosomal protein (e.g. rhGAA) molecules comprise at least one N-glycan unit bearing one or more mannose-6-phosphate residues or has the capacity to bind to CIMPR.

The recombinant human lysosomal protein (e.g. rhGAA) molecules may have 1, 2, 3 or 4 mannose-6-phosphate (M6P) groups on their glycans. For example, only one N-glycan on a recombinant human lysosomal protein molecule may bear M6P (mono-phosphorylated), a single N-glycan may bear two M6P groups (bis-phosphorylated), or two different N-glycans on the same recombinant human lysosomal protein molecule may each bear single M6P groups. Recombinant human lysosomal protein molecules may also have N-glycans bearing no M6P groups. In another embodiment, on average the N-glycans contain greater than 3 mol/mol of M6P and greater than 4 mol/mol sialic acid, such that the recombinant human lysosomal protein comprises on average at least 3 moles of mannose-6-phosphate residues per mole of recombinant human lysosomal protein and at least 4 moles of sialic acid per mole of recombinant human lysosomal protein. On average at least about 3, 4, 5, 6, 7, 8, 9, or 10% of the total glycans on the recombinant human lysosomal protein may be in the form of a mono-M6P glycan, for example, about 6.25% of the total glycans may carry a single M6P group and on average, at least about 0.5, 1, 1.5, 2.0, 2.5, 3.0% of the total glycans on recombinant human lysosomal protein are in the form of a bis-M6P glycan and on average less than 25% of total recombinant human lysosomal protein contains no phosphorylated glycan binding to CIMPR.

The recombinant human lysosomal protein (e.g. rhGAA) may have an average content of N-glycans carrying M6P ranging from 0.5 to 7.0 mol/mol lysosomal protein or any intermediate value of subrange including 0.5, 1.0, 1.5, 2.0, 2.5, 3.0, 3.5, 4.0, 4.5, 5.0, 5.5, 6.0, 6.5, or 7.0 mol/mol lysosomal protein. The lysosomal protein can be fractionated to provide lysosomal protein preparations with different average numbers of M6P-bearing or bis-M6P-bearing glycans thus permitting further customization of lysosomal protein targeting to the lysosomes in target tissues by selecting a particular fraction or by selectively combining different fractions.

In some embodiments, the recombinant human lysosomal protein (e.g. rhGAA) will bear, on average, 2.0 to 8.0 moles of M6P per mole of recombinant human lysosomal protein (e.g. rhGAA). This range includes all intermediate values and subranges including 2.0, 2.5, 3.0, 3.5, 4.0, 4.5, 5.0, 5.5, 6.0, 6.5, 7.0, 7.5 and 8.0 mol M6P/mol recombinant human lysosomal protein (e.g. rhGAA).

Up to 60% of the N-glycans on the recombinant human lysosomal protein (e.g. rhGAA) may be fully sialylated, for example, up to 10%, 20%, 30%, 40%, 50% or 60% of the N-glycans may be fully sialylated. In some embodiments from 4 to 20% of the total N-glycans are fully sialylated. In other embodiments no more than 5%, 10%, 20% or 30% of N-glycans on the recombinant human lysosomal protein (e.g. rhGAA) carry sialic acid and a terminal galactose residue (Gal). This range includes all intermediate values and subranges, for example, 7 to 30% of the total N-glycans on the recombinant human lysosomal protein can carry sialic acid and terminal galactose. In yet other embodiments, no more than 5, 10, 15, 16, 17, 18, 19 or 20% of the N-glycans on recombinant human lysosomal protein have a terminal galactose only and do not contain sialic acid. This range includes all intermediate values and subranges, for example, from 8 to 19% of the total N-glycans on the recombinant human lysosomal protein in the composition may have terminal galactose only and do not contain sialic acid.

In other embodiments of the invention, 40, 45, 50, 55 to 60% of the total N-glycans on the recombinant human lysosomal protein (e.g. rhGAA) are complex type N-glycans; or no more than 1, 2, 3, 4, 5, 6, 7% of total N-glycans on the recombinant human lysosomal protein (e.g. rhGAA) are hybrid-type N-glycans; no more than 5, 10, or 15% of the high mannose-type N-glycans on the recombinant human lysosomal protein (e.g. rhGAA) are non-phosphorylated; at least 5% or 10% of the high mannose-type N-glycans on the recombinant human lysosomal protein (e.g. rhGAA) are mono-M6P phosphorylated; and/or at least 1 or 2% of the high mannose-type N-glycans on the recombinant human lysosomal protein (e.g. rhGAA) are bis-M6P phosphorylated. These values include all intermediate values and subranges. A recombinant human lysosomal protein (e.g. rhGAA) may meet one or more of the content ranges described above.

In some embodiments, the recombinant human lysosomal protein (e.g. rhGAA) will bear, on average, 2.0 to 8.0 moles of sialic acid residues per mole of recombinant human lysosomal protein (e.g. rhGAA). This range includes all intermediate values and subranges including 2.0, 2.5, 3.0, 3.5, 4.0, 4.5, 5.0, 5.5, 6.0, 6.5, 7.0, 7.5 and 8.0 mol residues/mol recombinant human lysosomal protein (e.g. rhGAA). Without being bound by theory, it is believed that the presence of N-glycan units bearing sialic acid residues may prevent non-productive clearance of the recombinant human lysosomal protein (e.g. rhGAA) by asialoglycoprotein receptors.

In one or more embodiments, the recombinant human lysosomal protein (e.g. rhGAA) has M6P and/or sialic acid units at certain N-glycosylation sites of the recombinant human lysosomal protein. For example, as stated above, there are seven potential N-linked glycosylation sites on rhGAA. These potential glycosylation sites are at the following positions of SEQ ID NO: 2: N84, N177, N334, N414, N596, N826 and N869. Similarly, for the full-length amino acid sequence of SEQ ID NO: 1, these potential glycosylation sites are at the following positions: N140, N233, N390, N470, N652, N882 and N925. Other variants of rhGAA can have similar glycosylation sites, depending on the location of asparagine residues. Generally, sequences of ASN-X-SER or ASN-X-THR in the protein amino acid sequence indicate potential glycosylation sites, with the exception that X cannot be HIS or PRO.

In various embodiments, the rhGAA has a certain N-glycosylation profile. In one or more embodiments, at least 20% of the rhGAA is phosphorylated at the first N-glycosylation site (e.g. N84 for SEQ ID NO: 2 and N140 for SEQ ID NO: 1). For example, at least 20%, 25%, 30%, 35%, 40%, 45%, 50%, 55%, 60%, 65%, 70%, 75%, 80%, 85%, 90% or 95% of the rhGAA can be phosphorylated at the first N-glycosylation site. This phosphorylation can be the result of mono-M6P and/or bis-M6P units. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a mono-M6P unit at the first N-glycosylation site. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a bis-M6P unit at the first N-glycosylation site.

In one or more embodiments, at least 20% of the rhGAA is phosphorylated at the second N-glycosylation site (e.g. N177 for SEQ ID NO: 2 and N223 for SEQ ID NO: 1). For example, at least 20%, 25%, 30%, 35%, 40%, 45%, 50%, 55%, 60%, 65%, 70%, 75%, 80%, 85%, 90% or 95% of the rhGAA can be phosphorylated at the second N-glycosylation site. This phosphorylation can be the result of mono-M6P and/or bis-M6P units. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a mono-M6P unit at the second N-glycosylation site. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a bis-M6P unit at the second N-glycosylation site. In one or more embodiments, at least 5% of the rhGAA is phosphorylated at the third N-glycosylation site (e.g. N334 for SEQ ID NO: 2 and N390 for SEQ ID NO: 1). In other embodiments, less than 5%, 10%, 15%, 20% or 25% of the rhGAA is phosphorylated at the third N-glycosylation site. For example, the third N-glycosylation site can have a mixture of non-phosphorylated high mannose glycans, di-, tri-, and tetra-antennary complex glycans, and hybrid glycans as the major species. In some embodiments, at least 3%, 5%, 8%, 10%, 15%, 20%, 25%, 30%, 35%, 40%, 45% or 50% of the rhGAA is sialylated at the third N-glycosylation site.

In one or more embodiments, at least 20% of the rhGAA is phosphorylated at the fourth N-glycosylation site (e.g. N414 for SEQ ID NO: 2 and N470 for SEQ ID NO: 1). For example, at least 20%, 25%, 30%, 35%, 40%, 45%, 50%, 55%, 60%, 65%, 70%, 75%, 80%, 85%, 90% or 95% of the rhGAA can be phosphorylated at the fourth N-glycosylation site. This phosphorylation can be the result of mono-M6P and/or bis-M6P units. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a mono-M6P unit at the fourth N-glycosylation site. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a bis-M6P unit at the fourth N-glycosylation site. In some embodiments, at least 3%, 5%, 8%, 10%, 15%, 20% or 25% of the rhGAA is sialylated at the fourth N-glycosylation site.

In one or more embodiments, at least 5% of the rhGAA is phosphorylated at the fifth N-glycosylation site (e.g. N596 for SEQ ID NO: 2 and N692 for SEQ ID NO: 1). In other embodiments, less than 5%, 10%, 15%, 20% or 25% of the rhGAA is phosphorylated at the fifth N-glycosylation site. For example, the fifth N-glycosylation site can have fucosylated di-antennary complex glycans as the major species. In some embodiments, at least 3%, 5%, 8%, 10%, 15%, 20%, 25%, 30%, 35%, 40%, 45%, 50%, 55%, 60%, 65%, 70%, 75%, 80%, 85%, 90% or 95% of the rhGAA is sialylated at the fifth N-glycosylation site.

In one or more embodiments, at least 5% of the rhGAA is phosphorylated at the sixth N-glycosylation site (e.g. N826 for SEQ ID NO: 2 and N882 for SEQ ID NO: 1). In other embodiments, less than 5%, 10%, 15%, 20% or 25% of the rhGAA is phosphorylated at the sixth N-glycosylation site. For example, the sixth N-glycosylation site can have a mixture of di-, tri-, and tetra-antennary complex glycans as the major species. In some embodiments, at least 3%, 5%, 8%, 10%, 15%, 20%, 25%, 30%, 35%, 40%, 45%, 50%, 55%, 60%, 65%, 70%, 75%, 80%, 85%, 90% or 95% of the rhGAA is sialylated at the sixth N-glycosylation site.

In one or more embodiments, at least 5% of the rhGAA is phosphorylated at the seventh N-glycosylation site (e.g. N869 for SEQ ID NO: 2 and N925 for SEQ ID NO: 1). In other embodiments, less than 5%, 10%, 15%, 20% or 25% of the rhGAA is phosphorylated at the seventh N-glycosylation site. In some embodiments, less than 40%, 45%, 50%, 55%, 60% or 65% % of the rhGAA has any glycan at the seventh N-glycosylation site. In some embodiments, at least 30%, 35% or 40% of the rhGAA has a glycan at the seventh N-glycosylation site.

In various embodiments, the rhGAA has an average fucose content of 0-5 mol per mol of rhGAA, GlcNAc content of 10-30 mol per mol of rhGAA, galactose content of 5-20 mol per mol of rhGAA, mannose content of 10-40 mol per mol of rhGAA, M6P content of 2-8 mol per mol of rhGAA and sialic acid content of 2-8 mol per mol of rhGAA. In various embodiments, the rhGAA has an average fucose content of 2-3 mol per mol of rhGAA, GlcNAc content of 20-25 mol per mol of rhGAA, galactose content of 8-12 mol per mol of rhGAA, mannose content of 22-27 mol per mol of rhGAA, M6P content of 3-5 mol per mol of rhGAA and sialic acid content of 4-7 mol of rhGAA.

The recombinant human lysosomal protein (e.g. rhGAA) is preferably produced by Chinese hamster ovary (CHO) cells, such as CHO cell line GA-ATB-200 or ATB-200-001-X5-14, or by a subculture or derivative of such a CHO cell culture. DNA constructs, which express allelic variants of acid α-glucosidase or other variant acid α-glucosidase amino acid sequences such as those that are at least 90%, 95%, 98% or 99% identical to SEQ ID NO: 1 or SEQ ID NO: 2, may be constructed and expressed in CHO cells. These variant acid α-glucosidase amino acid sequences may contain deletions, substitutions and/or insertions relative to SEQ ID NO: 1 or SEQ ID NO: 2, such as having 1, 2, 3, 4, 5, 6, 7, 8, 9, 10, 11, 12, 13, 14, 15 or more deletions, substitutions and/or insertions relative to the amino acid sequence described by SEQ ID NO: 1 or SEQ ID NO: 2. Those of skill in the art can select alternative vectors suitable for transforming CHO cells for production of such DNA constructs.

Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

The inventors have found that recombinant human acid α-glucosidase having superior ability to target cation-independent mannose-6-phosphate receptors (CIMPR) and cellular lysosomes as well as glycosylation patterns that reduce its non-productive clearance in vivo can be produced using Chinese hamster ovary (CHO) cells. These cells can be induced to express recombinant human acid α-glucosidase with significantly higher levels of N-glycan units bearing one or more mannose-6-phosphate residues than conventional recombinant human acid α-glucosidase products such as alglucosidase alfa. The recombinant human acid α-glucosidase produced by these cells, for example, as exemplified by ATB200, has significantly more muscle cell-targeting mannose-6-phosphate (M6P) and bis-mannose-6-phosphate N-glycan residues than conventional acid α-glucosidase, such as Lumizyme®. Without being bound by theory, it is believed that this extensive glycosylation allows the ATB200 enzyme to be taken up more effectively into target cells, and therefore to be cleared from the circulation more efficiently than other recombinant human acid α-glucosidases, such as for example, alglucosidase alfa, which has a much lower M6P and bis-M6P content. ATB200 has been shown to efficiently bind to CIMPR and be efficiently taken up by skeletal muscle and cardiac muscle and to have a glycosylation pattern that provides a favorable pharmacokinetic profile and reduces non-productive clearance in vivo.

It is also contemplated that the extensive glycosylation of ATB200 can contribute to a reduction of the immunogenicity of ATB200 compared to, for example, alglucosidase alfa. As will be appreciated by those skilled in the art, glycosylation of proteins with conserved mammalian sugars generally enhances product solubility and diminishes product aggregation and immunogenicity. Glycosylation indirectly alters protein immunogenicity by minimizing protein aggregation as well as by shielding immunogenic protein epitopes from the immune system (Guidance for Industry—Immunogenicity Assessment for Therapeutic Protein Products, US Department of Health and Human Services, Food and Drug Administration, Center for Drug Evaluation and Research, Center for Biologics Evaluation and Research, August 2014). Therefore, in at least one embodiment, administration of the recombinant human acid α-glucosidase does not induce anti-drug antibodies. In at least one embodiment, administration of the recombinant human acid α-glucosidase induces a lower incidence of anti-drug antibodies in a subject than the level of anti-drug antibodies induced by administration of alglucosidase alfa.

As described in co-pending international patent application PCT/US2015/053252, cells such as CHO cells can be used to produce the rhGAA described therein, and this rhGAA can be used in the present invention. Examples of such a CHO cell line are GA-ATB-200 or ATB-200-001-X5-14, or a subculture thereof that produces a rhGAA composition as described therein. Such CHO cell lines may contain multiple copies of a gene, such as 5, 10, 15, or 20 or more copies, of a polynucleotide encoding GAA.

The high M6P and bis-M6P rhGAA, such as ATB200 rhGAA, can be produced by transforming CHO cells with a DNA construct that encodes GAA. While CHO cells have been previously used to make rhGAA, it was not appreciated that transformed CHO cells could be cultured and selected in a way that would produce rhGAA having a high content of M6P and bis-M6P glycans which target the CIMPR.

Surprisingly, it was found that it was possible to transform CHO cell lines, select transformants that produce rhGAA containing a high content of glycans bearing M6P or bis-M6P that target the CIMPR, and to stably express this high-M6P rhGAA. Thus, methods for making these CHO cell lines are also described in co-pending international patent application PCT/US2015/053252. This method involves transforming a CHO cell with DNA encoding GAA or a GAA variant, selecting a CHO cell that stably integrates the DNA encoding GAA into its chromosome(s) and that stably expresses GAA, and selecting a CHO cell that expresses GAA having a high content of glycans bearing M6P or bis-M6P, and, optionally, selecting a CHO cell having N-glycans with high sialic acid content and/or having N-glycans with a low non-phosphorylated high-mannose content.

These CHO cell lines may be used to produce rhGAA and rhGAA compositions by culturing the CHO cell line and recovering said composition from the culture of CHO cells.

Production, Capturing and Purification of Recombinant Human Lysosomal Protein

Various embodiments of the present invention pertain to methods for the production and/or capturing and/or purification of recombinant human lysosomal protein (e.g. rhGAA). An exemplary process 600 for producing, capturing and purifying recombinant human lysosomal protein is shown in FIG. 6.

Figure 6:
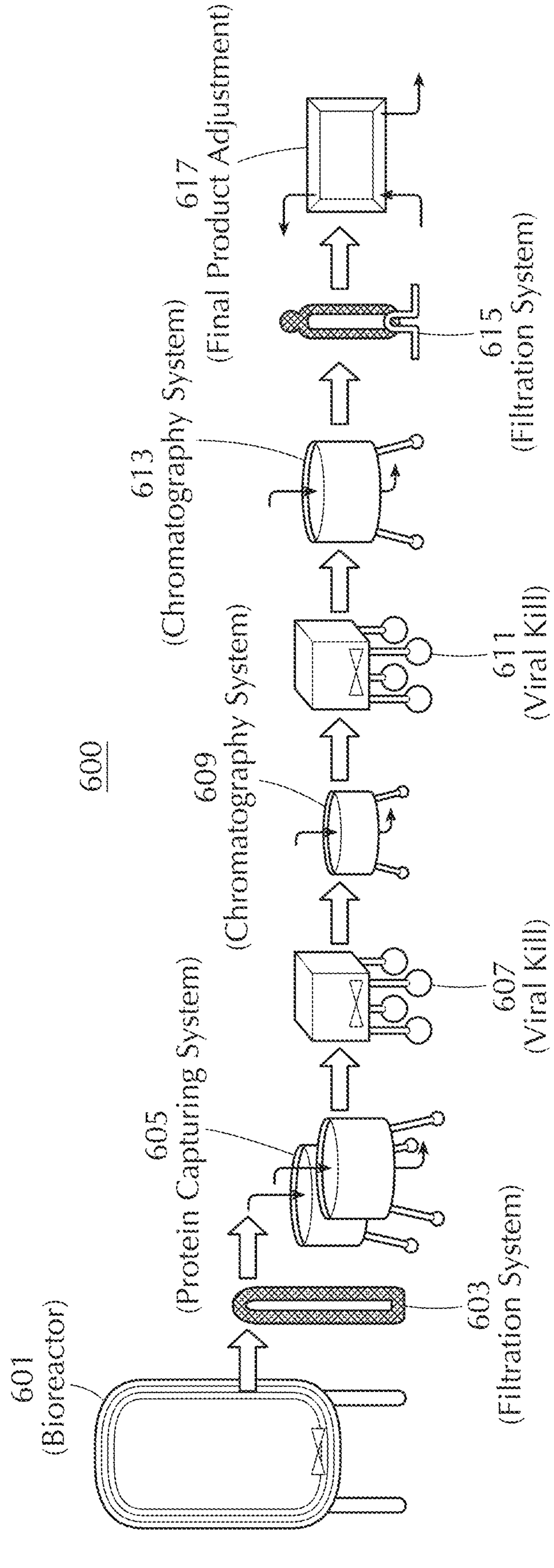
FIG. 6 is a schematic diagram of an exemplary process for the manufacturing, capturing and purification of a recombinant lysosomal protein.
Figure 7A:
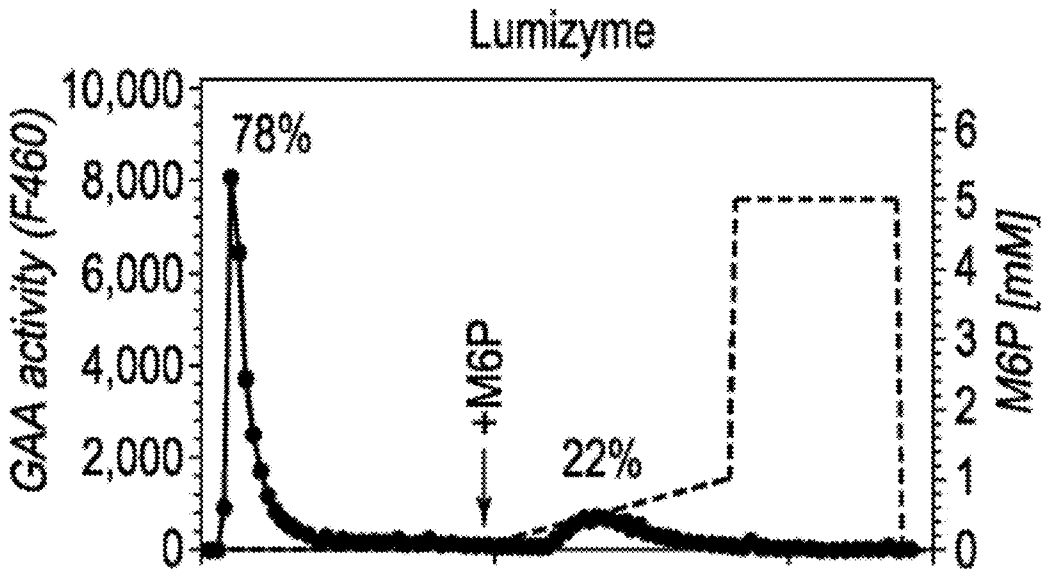
FIGS. 7A and 7B, respectively, are graphs showing the results of CIMPR affinity chromatography of Myozyme® and ATB200 rhGAA. As apparent from FIG. 7B, about 70% of the rhGAA in ATB200 rhGAA contained M6P.
Figure 7B:
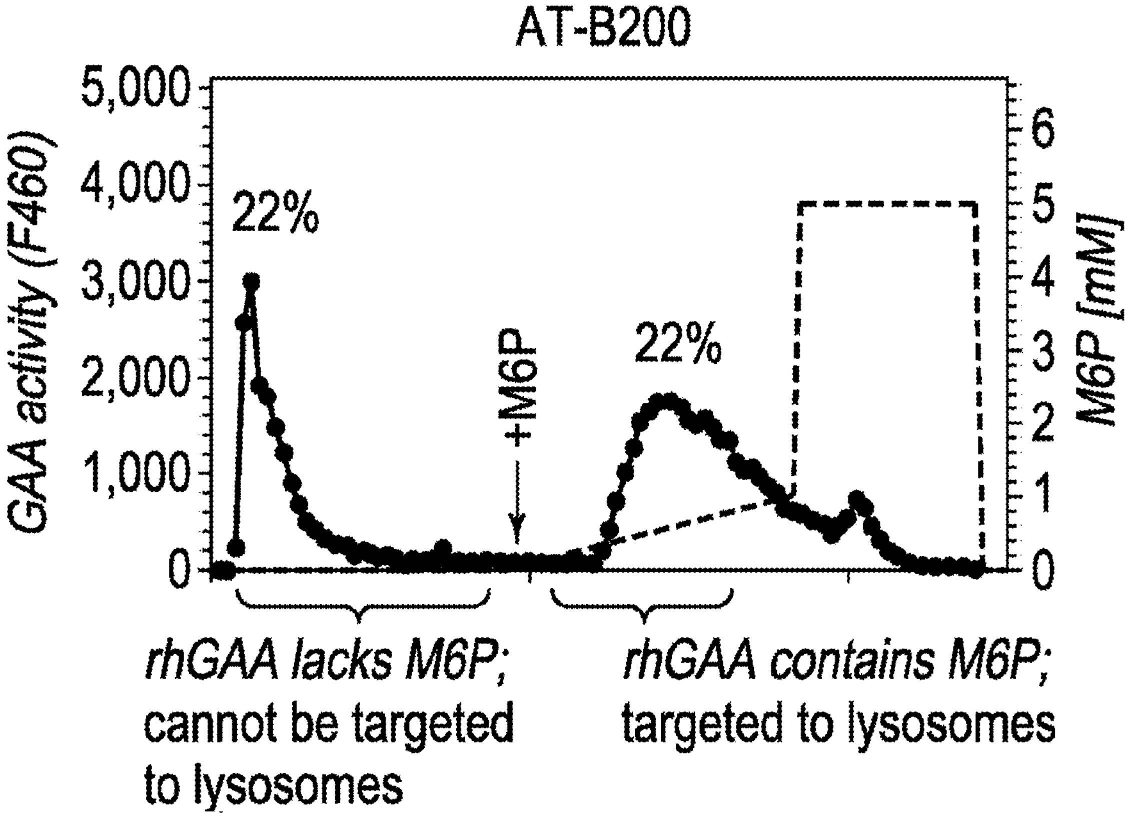

In FIG. 6, the arrows indicate the direction of movement for the various liquid phases containing the recombinant human lysosomal protein. Bioreactor 601 contains a culture of cells, such as CHO cells, that express and secrete recombinant human lysosomal protein (e.g. rhGAA) into the surrounding liquid culture media. The bioreactor 601 can be any appropriate bioreactor for culturing the cells, such as a perfusion, batch or fed-batch bioreactor. In various embodiments, the bioreactor has a volume between about 1 L and about 20,000 L. Exemplary bioreactor volumes include about 1 L, about 10 L, about 20 L, about 30 L, about 40 L, about 50 L, about 60 L, about 70 L, about 80 L, about 90 L, about 100 L, about 150 L, about 200 L, about 250 L, about 300 L, about 350 L, about 400 L, about 500 L, about 600 L, about 700 L, about 800 L, about 900 L, about 1,000 L, about 1,500 L, about 2,000 L, about 2,500 L, about 3,000 L, about 3,500 L, about 4,000 L, about 5,000 L, about 6,000 L, about 7,000 L, about 8,000 L, about 9,000 L, about 10,000 L, about 15,000 L and about 20,000 L.

As shown in FIG. 6, the media can be removed from the bioreactor. Such media removal can be continuous for a perfusion bioreactor or can be batchwise for a batch or fed-batch reactor. The media is filtered by filtration system 603 to remove cells. In some embodiments, the cells removed from the media are re-introduced to the bioreactor and the media comprising the secrete recombinant human lysosomal protein can be further processed. Filtration system 603 can be any suitable filtration system, including an alternating tangential flow filtration (ATF) system, a tangential flow filtration (TFF) system, centrifugal filtration system, etc. In various embodiments, the filtration system utilizes a filter having a pore size between about 10 nanometers and about 2 micrometers. Exemplary filter pore sizes include about 10 nm, about 20 nm, about 30 nm, about 40 nm, about 50 nm, about 60 nm, about 70 nm, about 80 nm, about 90 nm, about 100 nm, about 150 nm, about 200 nm, about 250 nm, about 300 nm, about 350 nm, about 400 nm, about 500 nm, about 600 nm, about 700 nm, about 800 nm, about 900 nm, about 1 μm, about 1.5 μm and about 2 μm.

In various embodiments, the media removal rate is between about 1 L/day and about 20,000 L/day. Exemplary media removal rates include about 1 L/day, about 10 L/day, about 20 L/day, about 30 L/day, about 40 L/day, about 50 L/day, about 60 L/day, about 70 L/day, about 80 L/day, about 90 L/day, about 100 L/day, about 150 L/day, about 200 L/day, about 250 L/day, about 300 L/day, about 350 L/day, about 400 L/day, about 500 L/day, about 600 L/day, about 700 L/day, about 800 L/day, about 900 L/day, about 1,000 L/day, about 1,500 L/day, about 2,000 L/day, about 2,500 L/day, about 3,000 L/day, about 3,500 L/day, about 4,000 L/day, about 5,000 L/day, about 6,000 L/day, about 7,000 L/day, about 8,000 L/day, about 9,000 L/day, about 10,000 L/day, about 15,000 L/day and about 20,000 L/day. Alternatively, the media removal rate can be expressed as a function of the bioreactor volume, such as about 0.1 to about 3 reactor volumes per day. Exemplary media removal rates include about 0.1, about 0.2, about 0.3, about 0.4, about 0.5, about 0.6, about 0.7, about 0.8, about 0.9, about 1, about 1.1, about 1.2, about 1.3, about 1.4, about 1.5, about 2, about 2.5 and about 3 reactor volumes per day.

For a continuous or fed-batch process, the rate at which fresh media is provided to the bioreactor can be between about 1 L/day and about 20,000 L/day. Exemplary media introduction rates include about 1 L/day, about 10 L/day, about 20 L/day, about 30 L/day, about 40 L/day, about 50 L/day, about 60 L/day, about 70 L/day, about 80 L/day, about 90 L/day, about 100 L/day, about 150 L/day, about 200 L/day, about 250 L/day, about 300 L/day, about 350 L/day, about 400 L/day, about 500 L/day, about 600 L/day, about 700 L/day, about 800 L/day, about 900 L/day, about 1,000 L/day, about 1,500 L/day, about 2,000 L/day, about 2,500 L/day, about 3,000 L/day, about 3,500 L/day, about 4,000 L/day, about 5,000 L/day, about 6,000 L/day, about 7,000 L/day, about 8,000 L/day, about 9,000 L/day, about 10,000 L/day, about 15,000 L/day and about 20,000 L/day. Alternatively, the media introduction rate can be expressed as a function of the bioreactor volume, such as about 0.1 to about 3 reactor volumes per day. Exemplary media introduction rates include about 0.1, about 0.2, about 0.3, about 0.4, about 0.5, about 0.6, about 0.7, about 0.8, about 0.9, about 1, about 1.1, about 1.2, about 1.3, about 1.4, about 1.5, about 2, about 2.5 and about 3 reactor volumes per day.

After filtration, the filtrate is loaded onto a protein capturing system 605. The protein capturing system 605 can include one or more chromatography columns. If more than one chromatography column is used, then the columns may be placed in series so that the next column can begin loading once the first column is loaded. Alternatively, the media removal process can be stopped during the time that the columns are switched.

In various embodiments, the protein capturing system 605 includes one or more anion exchange (AEX) columns for the direct product capture of recombinant human lysosomal protein, particularly lysosomal protein having a high M6P content. While not wishing to be bound by any particular theory, it is believed that using AEX chromatography to capture the recombinant human lysosomal protein from the filtered media ensures that the captured recombinant protein product has a higher M6P content, due to the more negative charge of the recombinant protein having one or more M6P groups. As a result, non-phosphorylated recombinant protein and host cell impurities do not bind the column resin as well as the highly phosphorylated recombinant protein, and the non-phosphorylated recombinant protein and host cell impurities passes through the column. Accordingly, the AEX chromatography can be used to enrich the M6P content of the protein product (i.e. select for proteins having more M6P) due to the high affinity of the M6P-containing proteins for the AEX resin.

Furthermore, while not wishing to be bound by any particular theory, it is also believed that having a direct product capture of recombinant protein using AEX chromatography ensures that the recombinant proteins having high M6P content are removed from the media containing proteases and other enzymes that can degrade the protein and/or dephosphorylate the protein. As a result, the high quality product is preserved.

Suitable AEX chromatography columns have functional chemical groups that bind negatively charged proteins. Exemplary functional groups include, but are not limited to, primary, secondary, tertiary, and quaternary ammonium or amine groups. These functional groups may be bound to membranes (e.g. cellulose membranes) or conventional chromatography resins. Exemplary column media include SP, CM, Q and DEAE Sepharose® Fast Flow media from GE Healthcare Lifesciences.

The volume of the AEX chromatography column can be any suitable volume, such as between 1 L and 1,000 L. Exemplary column volumes include about 1 L, about 2 L, about 3 L, about 4 L, about 5 L, about 6 L, about 7 L, about 8 L, about 9 L, about 10 L, about 20 L, about 30 L, about 40 L, about 50 L, about 60 L, about 70 L, about 80 L, about 90 L, about 100 L, about 150 L, about 200 L, about 250 L, about 300 L, about 350 L, about 400 L and about 500 L, about 600 L, about 700 L, about 800 L, about 900 L and about 1,000 L.

Exemplary conditions for an anion-exchange column are provided in Table 2 below:

TABLE 2

| Procedure | Buffer | Flow rate (cm/h) | Volume (CV) | Temperature (° C.) |
|---|---|---|---|---|
| Pre-used Sanitization | 0.1-10M NaOH | ≤25-2500 | ≥1-3 (≥10-120 min) | 15-25 |
| Pre-Equilibration | 20-2000 mM phosphate buffer (PB), pH 6.9-7.3 | ≤25-2500 | ≥1-5 | 15-25 |
| Equilibration | 4-400 mM PB, pH 6.9-7.3 | ≤25-2500 | ≥1-5 | 2-15 |
| Load | NA | ≤10-1000 | NA | 2-15 |
| Wash1 | 4-400 mM PB, pH 6.9-7.3 | ≤25-2500 | ≥2-10 | 2-15 |
| Wash2 | 4-400 mM PB, pH 6.9-7.3 | ≤25-2500 | ≥2-10 | 15-25 |
| Elution | 4-400 mM PB, 20-2000 mM NaCl, pH 6.1-6.5 | ≤25-2500 | NA | 15-25 |
| Strip | 4-400 mM PB, 0.1-10M NaCl, pH 6.1-6.5 | ≤25-2500 | ≥1-5 | 15-25 |
| Post-use Sanitization | 0.1-10M NaOH | ≤25-2500 | ≥1-3 (≥10-120 min) | 15-25 |
| Storage | 0.01-1.0M NaOH | ≤25-2500 | ≥1-5 | 15-25 |

After the recombinant human lysosomal protein is loaded onto the protein capturing system 605, the recombinant human lysosomal protein is eluted from the column(s) by changing the pH and/or salt content in the column.

The eluted recombinant human lysosomal protein can be subjected to further purification steps and/or quality assurance steps. For example, as shown in FIG. 6, the eluted recombinant human lysosomal protein can be subjected to a virus kill step 607. Such a virus kill 607 can include one or more of a low pH kill, a detergent kill, or other technique known in the art.

The recombinant protein product from the virus kill step 607 can be introduced into a second chromatography system 609 to further purify the recombinant protein product. Alternatively, the eluted recombinant protein from the protein capturing system 605 can be fed directly to the second chromatography system 609. In various embodiments, the second chromatography system 609 includes one or more immobilized metal affinity chromatography (IMAC) columns for further removal of impurities. Exemplary metal ions include cobalt, nickel, copper, iron, zinc or gallium.

The volume of the second chromatography column (e.g. IMAC column) can be any suitable volume, such as between 0.1 L and 100 L. Exemplary column volumes include about 0.1 L, about 0.2 L, about 0.3 L, about 0.4 L, about 0.5 L, about 0.6 L, about 0.7 L, about 0.8 L, about 0.9 L, about 1 L, about 1.5 L, about 2 L, about 2.5 L, about 3 L, about 3.5 L, about 4 L, about 4.5 L, about 5 L, about 6 L, about 7 L, about 8 L, about 9 L, about 10 L, about 15 L, about 20 L, about 25 L, about 30 L, about 35 L, about 40 L and about 50 L, about 60 L, about 70 L, about 80 L, about 90 L and about 100 L.

Exemplary conditions for an IMAC column are provided in Table 3 below:

TABLE 3

| Procedure | Buffer | Flow rate (cm/h) | Vol (CV) |
|---|---|---|---|
| Rinse | 4-400 mM PB, pH 6.3-6.7 | ≤25-2500 | ≥1-5 |
| Pre-use Sanitization | 0.01-1.0M NaOH | ≤25-2500 | ≥1-3 (10-30 min) |
| Equilibration | 4-400 mM PB, pH 6.5 | ≤25-2500 | ≥1-5 |
| Wash with WFI | Water For Injection (WFI) | ≤25-2500 | ≥1-3 |
| Chelating | 0.01-1.0M Copper Acetate | ≤25-2500 | ≥1-5 |
| Wash with WFI | WFI | ≤25-2500 | ≥2-10 |
| Wash with acidic buffer | 2-200 mM Sodium Acetate, 0.05-5M NaCl, pH 3.5-4.5 | ≤25-2500 | ≥2-10 |
| Equilibration | 4-400 mM PB, pH 6.3-6.7 | ≤25-2500 | ≥1-5 |
| Blank run with elution buffer | 4-400 mM PB, 15-1500 mM Glycine, pH 6.1-6.5 | ≤25-2500 | ≥2-20 |
| Equilibration | 4-400 mM PB, pH 6.3-6.7 | ≤25-2500 | ≥1-5 |
| Load | NA | ≤25-2500 | ≥1-5 |
| Wash1 | 4-400 mM PB, pH 6.3-6.7 | ≤25-2500 | ≥2-10 |
| Wash2 | 4-400 mM PB, 0.1-10M NaCl, 5-30% propylene glycol, pH 6.3-6.7 | ≤25-2500 | ≥2-10 |
| Wash3 | 4-400 mM PB, pH 6.3-6.7 | ≤25-2500 | ≥2-10 |
| Elution | 4-400 mM PB, 15-1500 mM Glycine, pH 6.1-6.5 | ≤25-2500 | NA |
| Strip | 4-400 mM PB, 50-5000 mM imidazole, pH 6.3-6.7 | ≤25-2500 | ≥1-5 |
| Post-use Sanitization | 0.01-1M NaOH | ≤25-2500 | ≥1-3 (10-30 min) |
| Rinse | 4-400 mM PB, pH 6.3-6.7 | ≤25-2500 | ≥1-5 |
| Storage | 5-30% ethanol | ≤25-2500 | ≥1-5 |

After the recombinant protein is loaded onto the second chromatography system 609, the recombinant protein is eluted from the column(s). As shown in FIG. 6, the eluted recombinant protein can be subjected to a virus kill step 611. As with virus kill 607, virus kill 611 can include one or more of a low pH kill, a detergent kill, or other technique known in the art. In some embodiments, only one of virus kill 607 or 611 is used, or the virus kills are performed at the same stage in the purification process.

As shown in FIG. 6, the recombinant protein product from the virus kill step 611 can be introduced into a third chromatography system 613 to further purify the recombinant protein product. Alternatively, the eluted recombinant protein from the second chromatography system 609 can be fed directly to the third chromatography system 613. In various embodiments, the third chromatography system 613 includes one or more cation exchange chromatography (CEX) columns and/or size exclusion chromatography (SEC) columns for further removal of impurities. The recombinant protein product is then eluted from the third chromatography system 613.

The volume of the third chromatography column (e.g. CEX or SEC column) can be any suitable volume, such as between 0.1 L and 200 L. Exemplary column volumes include about 0.1 L, about 0.2 L, about 0.3 L, about 0.4 L, about 0.5 L, about 0.6 L, about 0.7 L, about 0.8 L, about 0.9 L, about 1 L, about 1.5 L, about 2 L, about 2.5 L, about 3 L, about 3.5 L, about 4 L, about 4.5 L, about 5 L, about 6 L, about 7 L, about 8 L, about 9 L, about 10 L, about 15 L, about 20 L, about 25 L, about 30 L, about 35 L, about 40 L and about 50 L, about 60 L, about 70 L, about 80 L, about 90 L, about 100 L, about 150 L and about 200 L.

Exemplary conditions for a CEX column are provided in Table 4 below:

TABLE 4

| Procedure | Buffer | Flow rate (cm/h) | Vol (CV) |
|---|---|---|---|
| Pre-used Sanitization | 0.1-10M NaOH | ≤25-2500 | ≥1-3 (≥10-120 min) |
| Equilibration | 2-200 mM Sodium citrate, pH 4.0-5.0 | ≤30-3000 | ≥2-10 |
| Load | NA | ≤30-3000 | NA |
| Wash | 2-200 mM Sodium citrate, pH 4.0-5.0 | ≤30-3000 | ≥2-10 |
| Elution | 2-200 mM Sodium citrate, 15-1500 mM NaCl, pH 4.0-5.0 | ≤30-3000 | ≥2-10 |
| Strip | 2-200 mM Sodium citrate, 0.1-10M NaCl, pH 4.0-5.0 | ≤30-3000 | ≥1-5 |
| Post-use Sanitization | 0.1-10M NaOH | ≤25-2500 | ≥1-3 (≥10-120 min) |
| Storage | 0.01-1.0M NaOH | ≤30-3000 | ≥1-5 |

The recombinant protein product may also be subjected to further processing. For example, another filtration system 615 may be used to remove viruses. In some embodiments, such filtration can utilize filters with pore sizes between 5 and 50 μm. Other product processing can include a product adjustment step 617, in which the recombinant protein product may be sterilized, filtered, concentrated, stored and/or have additional components for added for the final product formulation. For example, the recombinant protein product can be concentrated by a factor of 2-10 times, such as from an initial protein concentration of about 2 to about 20 mg/ml to a final protein concentration of about 4 to about 200 mg/ml. This final product can be used to fill vials and may be lyophilized for future use.

Administration of Recombinant Protein

The recombinant human lysosomal protein (e.g. rhGAA), or a pharmaceutically acceptable salt thereof, can be formulated in accordance with the routine procedures as a pharmaceutical composition adapted for administration to human beings. For example, in a preferred embodiment, a composition for intravenous administration is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

Recombinant human lysosomal protein (e.g. rhGAA) (or a composition or medicament containing recombinant human lysosomal protein) is administered by an appropriate route. In one embodiment, the recombinant human lysosomal protein is administered intravenously. In other embodiments, recombinant human lysosomal protein (e.g. rhGAA) is administered by direct administration to a target tissue, such as to heart or skeletal muscle (e.g. intramuscular), or nervous system (e.g. direct injection into the brain; intraventricularly; intrathecally). More than one route can be used concurrently, if desired.

The recombinant human lysosomal protein (e.g. rhGAA) (or a composition or medicament containing recombinant human lysosomal protein) is administered in a therapeutically effective amount (e.g. a dosage amount that, when administered at regular intervals, is sufficient to treat the disease, such as by ameliorating symptoms associated with the disease, preventing or delaying the onset of the disease, and/or lessening the severity or frequency of symptoms of the disease). The amount which will be therapeutically effective in the treatment of the disease will depend on the nature and extent of the disease's effects, and can be determined by standard clinical techniques. In addition, in vitro or in vivo assays may optionally be employed to help identify optimal dosage ranges. The precise dose to be employed will also depend on the route of administration, and the seriousness of the disease, and should be decided according to the judgment of a practitioner and each patient's circumstances. Effective doses may be extrapolated from dose-response curves derived from in vitro or animal model test systems. In at least one embodiment, the recombinant human acid α-glucosidase is administered by intravenous infusion at a dose of about 1 mg/kg to about 100 mg/kg, such as about 5 mg/kg to about 30 mg/kg, typically about 5 mg/kg to about 20 mg/kg. In at least one embodiment, the recombinant human acid α-glucosidase is administered by intravenous infusion at a dose of about 5 mg/kg, about 10 mg/kg, about 15 mg/kg, about 20 mg/kg, about 25 mg/kg, about 30 mg/kg, about 35 mg/kg, about 40 mg/kg, about 50 mg/kg, about 50 mg/kg, about 60 mg/kg, about 70 mg/kg, about 80 mg/kg, about 90 mg/kg or about 100 mg/kg. In at least one embodiment, the recombinant human acid α-glucosidase is administered by intravenous infusion at a dose of about 20 mg/kg. The effective dose for a particular individual can be varied (e.g. increased or decreased) over time, depending on the needs of the individual. For example, in times of physical illness or stress, or if anti-acid α-glucosidase antibodies become present or increase, or if disease symptoms worsen, the amount can be increased.

The therapeutically effective amount of recombinant human acid α-glucosidase (or composition or medicament containing recombinant human acid α-glucosidase) is administered at regular intervals, depending on the nature and extent of the disease's effects, and on an ongoing basis. Administration at a "regular interval," as used herein, indicates that the therapeutically effective amount is administered periodically (as distinguished from a one-time dose). The interval can be determined by standard clinical techniques. In preferred embodiments, recombinant human acid α-glucosidase is administered monthly, bimonthly; weekly; twice weekly; or daily. The administration interval for a single individual need not be a fixed interval, but can be varied over time, depending on the needs of the individual. For example, in times of physical illness or stress, if anti-recombinant human acid α-glucosidase antibodies become present or increase, or if disease symptoms worsen, the interval between doses can be decreased. In some embodiments, a therapeutically effective amount of 5, 10, 20, 50, 100, or 200 mg enzyme/kg body weight is administered twice a week, weekly or every other week with or without a chaperone.

The recombinant human lysosomal protein (e.g. rhGAA) may be prepared for later use, such as in a unit dose vial or syringe, or in a bottle or bag for intravenous administration. Kits containing the recombinant human lysosomal protein (e.g. rhGAA), as well as optional excipients or other active ingredients, such as chaperones or other drugs, may be enclosed in packaging material and accompanied by instructions for reconstitution, dilution or dosing for treating a subject in need of treatment, such as a patient having Pompe disease.

Combination Therapy of rhGAA and Pharmacological Chaperone

In various embodiments, the rhGAA (e.g. ATB200) produced by the processes described herein can be used in combination therapy with a pharmacological chaperone such as miglustat or duvoglustat.

In at least one embodiment, the pharmacological chaperone (e.g. miglustat) is administered orally. In at least one embodiment, the miglustat is administered at an oral dose of about 200 mg to about 400 mg, or at an oral dose of about 200 mg, about 250 mg, about 300 mg, about 350 mg or about 400 mg. In at least one embodiment, the miglustat is administered at an oral dose of about 233 mg to about 400 mg. In at least one embodiment, the miglustat is administered at an oral dose of about 250 to about 270 mg, or at an oral dose of about 250 mg, about 255 mg, about 260 mg, about 265 mg or about 270 mg. In at least one embodiment, the miglustat is administered as an oral dose of about 260 mg.

It will be understood by those skilled in the art that an oral dose of miglustat in the range of about 200 mg to 400 mg or any smaller range therewithin can be suitable for an adult patient with an average body weight of about 70 kg. For patients having a significantly lower body weight than about 70 kg, including but not limited to infants, children or underweight adults, a smaller dose may be considered suitable by a physician. Therefore, in at least one embodiment, the miglustat is administered as an oral dose of from about 50 mg to about 200 mg, or as an oral dose of about 50 mg, about 75 mg, about 100 mg, 125 mg, about 150 mg, about 175 mg or about 200 mg. In at least one embodiment, the miglustat is administered as an oral dose of from about 65 mg to about 195 mg, or as an oral dose of about 65 mg, about 130 mg or about 195 mg.

In at least one embodiment, the miglustat is administered as a pharmaceutically acceptable dosage form suitable for oral administration, and includes but is not limited to tablets, capsules, ovules, elixirs, solutions or suspensions, gels, syrups, mouth washes, or a dry powder for reconstitution with water or other suitable vehicle before use, optionally with flavoring and coloring agents for immediate-, delayed-, modified-, sustained-, pulsed- or controlled-release applications. Solid compositions such as tablets, capsules, lozenges, pastilles, pills, boluses, powder, pastes, granules, bullets, dragées or premix preparations can also be used. In at least one embodiment, the miglustat is administered as a tablet. In at least one embodiment, the miglustat is administered as a capsule. In at least one embodiment, the dosage form contains from about 50 mg to about 300 mg of miglustat. In at least one embodiment, the dosage form contains about 65 mg of miglustat. In at least one embodiment, the dosage form contains about 130 mg of miglustat. In at least one embodiment, the dosage form contains about 260 mg of miglustat. It is contemplated that when the dosage form contains about 65 mg of miglustat, the miglustat can be administered as a dosage of four dosage forms, or a total dose of 260 mg of miglustat. However, for patients who have a significantly lower weight than an average adult weight of 70 kg, including but not limited to infants, children or underweight adults, the miglustat can be administered as a dosage of one dosage form (a total dose of 65 mg of miglustat), two dosage forms (a total dose of 130 mg of miglustat), or three dosage forms (a total dose of 195 mg of miglustat).

Solid and liquid compositions for oral use can be prepared according to methods well known in the art. Such compositions can also contain one or more pharmaceutically acceptable carriers and excipients which can be in solid or liquid form. Tablets or capsules can be prepared by conventional means with pharmaceutically acceptable excipients, including but not limited to binding agents, fillers, lubricants, disintegrants or wetting agents. Suitable pharmaceutically acceptable excipients are known in the art and include but are not limited to pregelatinized starch, polyvinylpyrrolidone, povidone, hydroxypropyl methylcellulose (HPMC), hydroxypropyl ethylcellulose (HPEC), hydroxypropyl cellulose (HPC), sucrose, gelatin, acacia, lactose, microcrystalline cellulose, calcium hydrogen phosphate, magnesium stearate, stearic acid, glyceryl behenate, talc, silica, corn, potato or tapioca starch, sodium starch glycolate, sodium lauryl sulfate, sodium citrate, calcium carbonate, dibasic calcium phosphate, glycine croscarmellose sodium and complex silicates. Tablets can be coated by methods well known in the art. In at least one embodiment, the miglustat is administered as a formulation available commercially as Zavesca® (Actelion Pharmaceuticals).

In at least one embodiment, the miglustat and the recombinant human acid α-glucosidase are administered simultaneously. In at least one embodiment, the miglustat and the recombinant human acid α-glucosidase are administered sequentially. In at least one embodiment, the miglustat is administered prior to administration of the recombinant human acid α-glucosidase. In at least one embodiment, the miglustat is administered less than three hours prior to administration of the recombinant human acid α-glucosidase. In at least one embodiment, the miglustat is administered about two hours prior to administration of the recombinant human acid α-glucosidase. In at least one embodiment, the miglustat is administered less than two hours prior to administration of the recombinant human acid α-glucosidase. In at least one embodiment, the miglustat is administered about 1.5 hours prior to administration of the recombinant human acid α-glucosidase. In at least one embodiment, the miglustat is administered about one hour prior to administration of the recombinant human acid α-glucosidase. In at least one embodiment, the miglustat is administered from about 50 minutes to about 70 minutes prior to administration of the recombinant human acid α-glucosidase. In at least one embodiment, the miglustat is administered from about 55 minutes to about 65 minutes prior to administration of the recombinant human acid α-glucosidase. In at least one embodiment, the miglustat is administered about 30 minutes prior to administration of the recombinant human acid α-glucosidase. In at least one embodiment, the miglustat is administered from about 25 minutes to about 35 minutes prior to administration of the recombinant human acid α-glucosidase. In at least one embodiment, the miglustat is administered from about 27 minutes to about 33 minutes prior to administration of the recombinant human acid α-glucosidase.

In at least one embodiment, the miglustat is administered concurrently with administration of the recombinant human acid α-glucosidase. In at least one embodiment, the miglustat is administered within 20 minutes before or after administration of the recombinant human acid α-glucosidase. In at least one embodiment, the miglustat is administered within 15 minutes before or after administration of the recombinant human acid α-glucosidase. In at least one embodiment, the miglustat is administered within 10 minutes before or after administration of the recombinant human acid α-glucosidase. In at least one embodiment, the miglustat is administered within 5 minutes before or after administration of the recombinant human acid α-glucosidase.

In at least one embodiment, the miglustat is administered after administration of the recombinant human acid α-glucosidase. In at least one embodiment, the miglustat is administered up to 2 hours after administration of the recombinant human acid α-glucosidase. In at least one embodiment, the miglustat is administered about 30 minutes after administration of the recombinant human acid α-glucosidase. In at least one embodiment, the miglustat is administered about one hour after administration of the recombinant human acid α-glucosidase. In at least one embodiment, the miglustat is administered about 1.5 hours after administration of the recombinant human acid α-glucosidase. In at least one embodiment, the miglustat is administered about 2 hours after administration of the recombinant human acid α-glucosidase.

Another aspect of the invention provides a kit for combination therapy of Pompe disease in a patient in need thereof. The kit includes a pharmaceutically acceptable dosage form comprising miglustat, a pharmaceutically acceptable dosage form comprising a recombinant human acid α-glucosidase as defined herein, and instructions for administering the pharmaceutically acceptable dosage form comprising miglustat and the pharmaceutically acceptable dosage form comprising the recombinant acid α-glucosidase to a patient in need thereof. In at least one embodiment, the pharmaceutically acceptable dosage form comprising miglustat is an oral dosage form as described herein, including but not limited to a tablet or a capsule. In at least one embodiment, the pharmaceutically acceptable dosage form comprising a recombinant human acid α-glucosidase is a sterile solution suitable for injection as described herein. In at least one embodiment, the instructions for administering the dosage forms include instructions to administer the pharmaceutically acceptable dosage form comprising miglustat orally prior to administering the pharmaceutically acceptable dosage form comprising the recombinant human acid α-glucosidase by intravenous infusion, as described herein.

Without being bound by theory, it is believed that miglustat acts as a pharmacological chaperone for the recombinant human acid α-glucosidase ATB200 and binds to its active site. For example, miglustat has been found to decrease the percentage of unfolded ATB200 protein and stabilize the active conformation of ATB200, preventing denaturation and irreversible inactivation at the neutral pH of plasma and allowing it to survive conditions in the circulation long enough to reach and be taken up by tissues. However, the binding of miglustat to the active site of ATB200 also can result in inhibition of the enzymatic activity of ATB200 by preventing the natural substrate, glycogen, from accessing the active site. It is believed that when miglustat and the recombinant human acid α-glucosidase are administered to a patient under the conditions described herein, the concentrations of miglustat and ATB200 within the plasma and tissues are such that ATB200 is stabilized until it can be taken up into the tissues and targeted to lysosomes, but, because of the rapid clearance of miglustat, hydrolysis of glycogen by ATB200 within lysosomes is not overly inhibited by the presence of miglustat, and the enzyme retains sufficient activity to be therapeutically useful.

All the embodiments described above may be combined. This includes in particular embodiments relating to:

- the nature of the pharmacological chaperone, for example miglustat; and the active site for which it is specific;
- the dosage, route of administration of the pharmacological chaperone (e.g. miglustat) and the type of pharmaceutical composition including the nature of the carrier and the use of commercially available compositions;
- the nature of the drug, e.g. therapeutic protein drug product, which may be a counterpart of an endogenous protein for which expression is reduced or absent in the subject, suitably recombinant human lysosomal protein (e.g. rhGAA), for example the recombinant human acid α-glucosidase expressed in Chinese hamster ovary (CHO) cells and comprising an increased content of N-glycan units bearing one or more mannose phosphate residues when compared to a content of N-glycan units bearing one or more mannose-6-phosphate residues of alglucosidase alfa; and suitably having an amino acid sequence as set forth in SEQ ID NO: 1 or SEQ ID NO: 2;
- the number and type of N-glycan units on the recombinant human lysosomal protein (e.g. rhGAA), such as the N-acetylglucosamine, galactose, sialic acid or complex N-glycans formed from combinations of these, attached to the recombinant human lysosomal protein;
- the degree of phosphorylation of mannose units on the recombinant human lysosomal protein (e.g. rhGAA) to form mannose-6-phosphate and/or bis-mannose-6-phosphate;
- the dosage and route of administration (e.g. intravenous administration, especially intravenous infusion, or direct administration to the target tissue) of the replacement enzyme (e.g. recombinant human acid α-glucosidase) and the type of formulation including carriers and therapeutically effective amount;
- the dosage interval of the pharmacological chaperone (miglustat) and the recombinant human acid α-glucosidase;
- the nature of the therapeutic response and the results of the combination therapy (e.g. enhanced results as compared to the effect of each therapy performed individually);
- the timing of the administration of the combination therapy, e.g. simultaneous administration of miglustat and the recombinant human acid α-glucosidase or sequential administration, for example wherein the miglustat is administered prior to the recombinant human acid α-glucosidase or after the recombinant human acid α-glucosidase or within a certain time before or after administration of the recombinant human acid α-glucosidase; and
- the nature of the patient treated (e.g. mammal such as human) and the condition suffered by the individual (e.g. enzyme insufficiency).

Any of the embodiments in the list above may be combined with one or more of the other embodiments in the list.

EXAMPLES

Other features of the present invention will become apparent from the following non-limiting examples which illustrate, by way of example, the principles of the invention.

Example 1: Limitations of Existing Myozyme® and Lumizyme® rhGAA Products

To evaluate the ability of the rhGAA in Myozyme® and Lumizyme®, the only currently approved treatments for Pompe disease, these rhGAA preparations were injected onto a CIMPR column (which binds rhGAA having M6P groups) and subsequently eluted with a free M6 gradient. Fractions were collected in 96-well plate and GAA activity assayed by 4MU-α-glucose substrate. The relative amounts of bound and unbound rhGAA were determined based on GAA activity and reported as the fraction of total enzyme.

Figure 4A:
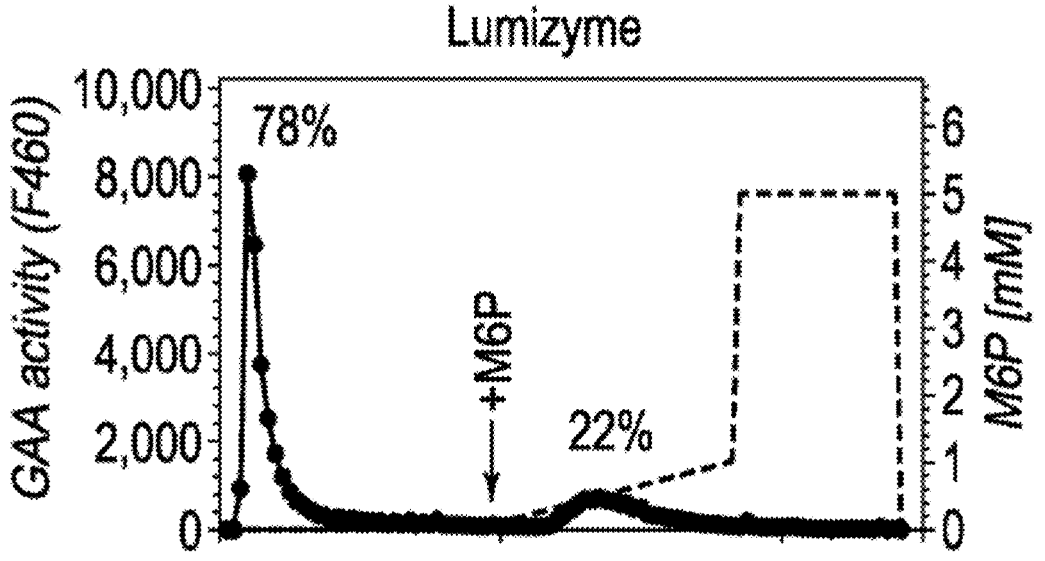
FIGS. 4A and 4B, respectively, are graphs showing the results of CIMPR affinity chromatography of Lumizyme® and Myozyme®. The dashed lines refer to the M6P elution gradient. Elution with M6P displaces GAA molecules bound via an M6P containing glycan to CIMPR.
Figure 4B:
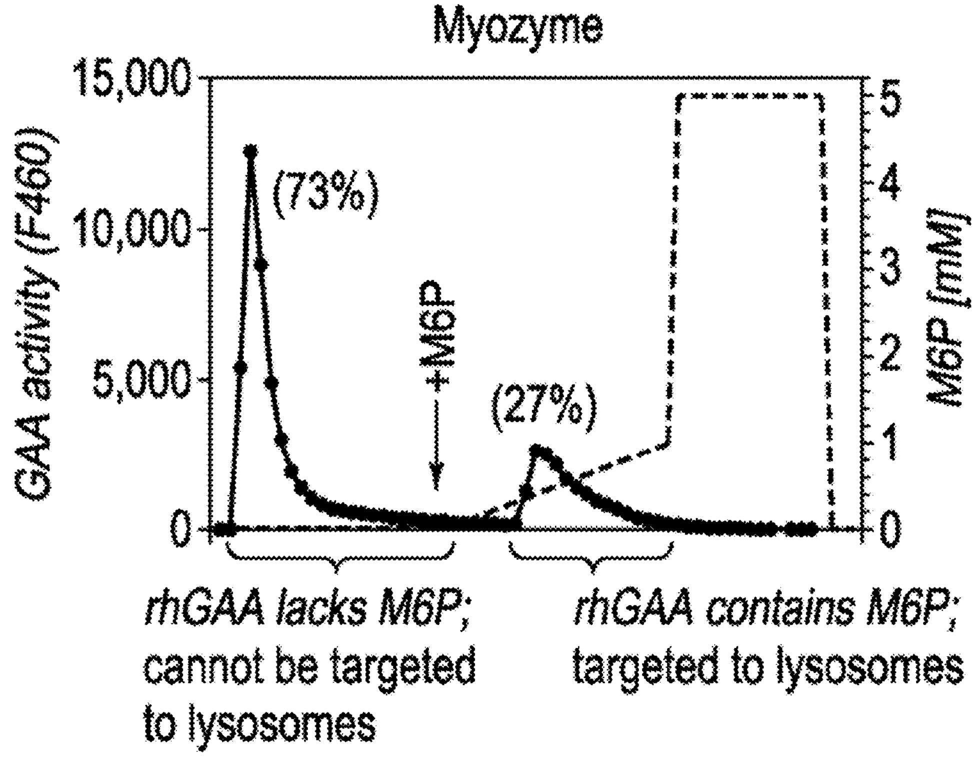

FIGS. 4A-B describe the problems associated with conventional ERTs (Myozyme® and Lumizyme®): 73% of the rhGAA in Myozyme® (FIG. 4B) and 78% of the rhGAA in Lumizyme® (FIG. 4A) did not bind to the CIMPR, see the left-most peaks in each figure. Only 27% of the rhGAA in Myozyme® and 22% of the rhGAA in Lumizyme® contained M6P that can productive to target it to the CIMPR on muscle cells.

An effective dose of Myozyme® and Lumizyme® corresponds to the amount of rhGAA containing M6P which targets the CIMPR on muscle cells. However, most of the rhGAA in these two conventional products does not target the CIMPR receptor on target muscle cells. The administration of a conventional rhGAA where most of the rhGAA is not targeted to muscle cells increases the risk of allergic reaction or induction of immunity to the non-targeted rhGAA.

Figure 5:
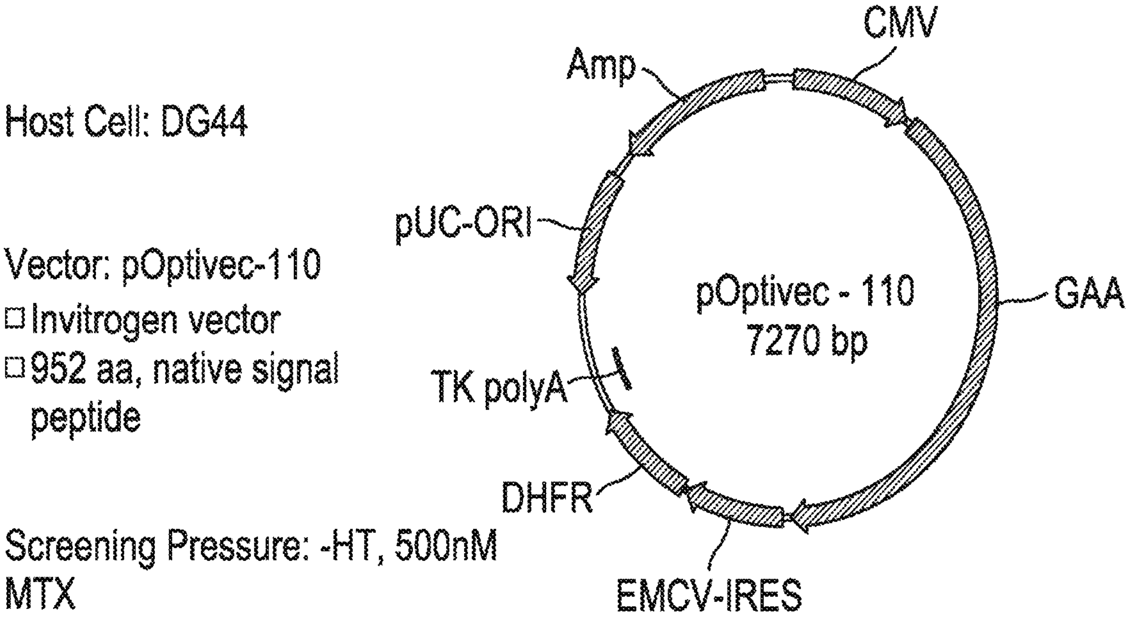
FIG. 5 shows a DNA construct for transforming CHO cells with DNA encoding rhGAA. CHO cells were transformed with a DNA construct encoding rhGAA.

Example 2: Preparation of CHO Cells Producing ATB200 rhGAA Having a High Content of Mono- or Bis-M6P-Bearing N-Glycans CHO cells were transfected with DNA that expresses rhGAA followed by selection of transformants producing rhGAA. A DNA construct for transforming CHO cells with DNA encoding rhGAA is shown in FIG. 5. CHO cells were transfected with DNA that expresses rhGAA followed by selection of transformants producing rhGAA.

After transfection, DG44 CHO (DHFR−) cells containing a stably integrated GAA gene were selected with hypoxanthine/thymidine deficient (-HT) medium). Amplification of GAA expression in these cells was induced by methotrexate treatment (MTX, 500 nM). Cell pools that expressed high amounts of GAA were identified by GAA enzyme activity assays and were used to establish individual clones producing rhGAA. Individual clones were generated on semisolid media plates, picked by ClonePix system, and were transferred to 24-deep well plates. The individual clones were assayed for GAA enzyme activity to identify clones expressing a high level of GAA. Conditioned media for determining GAA activity used a 4-MU-a-Glucosidase substrate. Clones producing higher levels of GAA as measured by GAA enzyme assays were further evaluated for viability, ability to grow, GAA productivity, N-glycan structure and stable protein expression. CHO cell lines, including CHO cell line GA-ATB-200, expressing rhGAA with enhanced mono-M6P or bis-M6P N-glycans were isolated using this procedure.

Example 3: Capturing and Purification of ATB200 rhGAA

Figure 8:
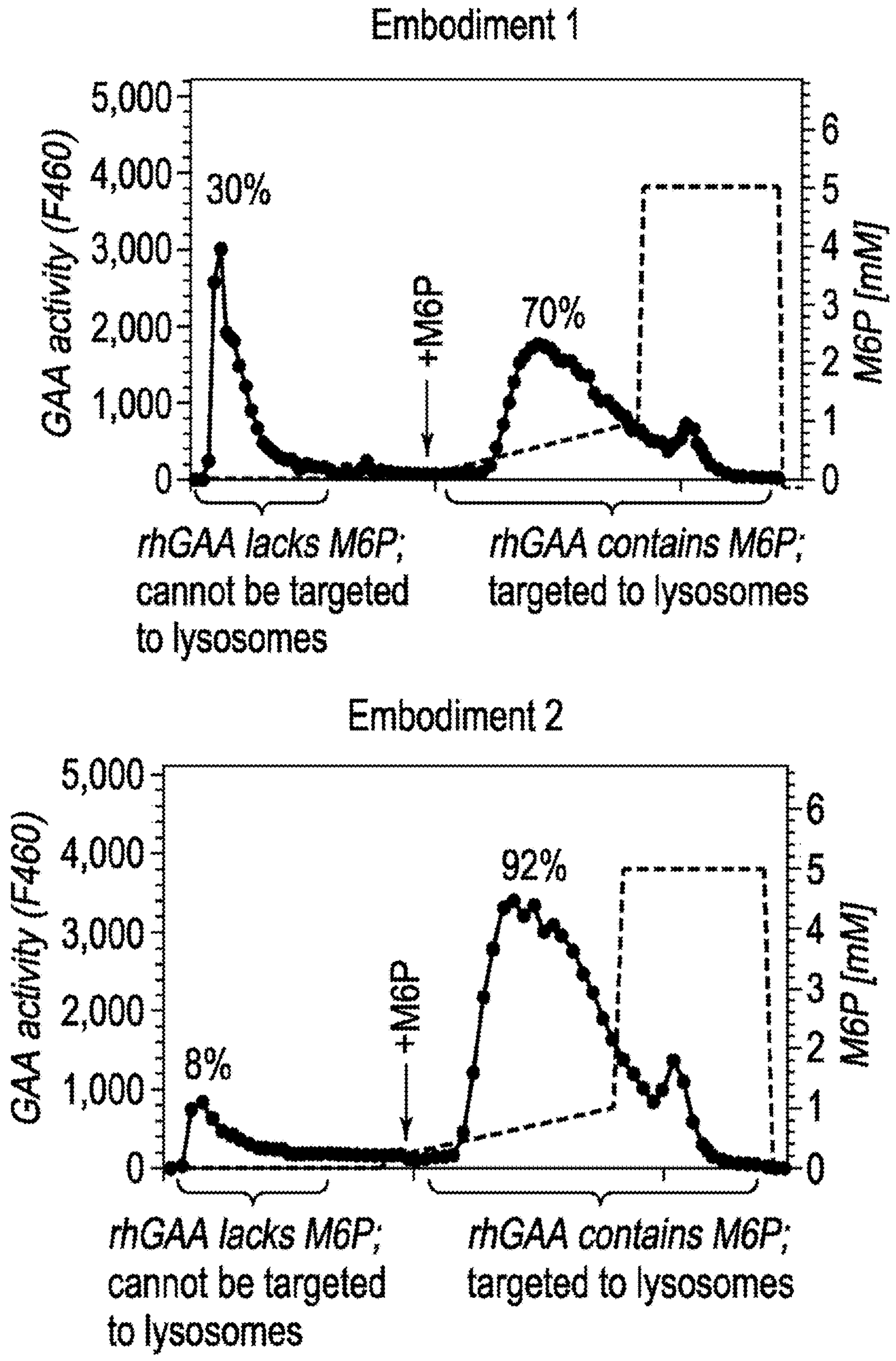
FIG. 8 is a graph showing the results of CIMPR affinity chromatography of ATB200 rhGAA with and without capture on an anion exchange (AEX) column.

Multiple batches of the rhGAA according to the invention were produced in shake flasks and in perfusion bioreactors using CHO cell line GA-ATB-200 and CIMPR binding was measured. Similar CIMPR receptor binding (~70%) to that shown in FIG. 7B and FIG. 8 was observed for purified ATB200 rhGAA from different production batches indicating that ATB200 rhGAA can be consistently produced. As shown by FIGS. 4A, 4B, 7A and 7B, Myozyme® and Lumizyme® rhGAAs exhibited significantly less CIMPR binding than ATB200 rhGAA.

Example 4: Analytical Comparison of ATB200 to Lumizyme®

Figure 9:
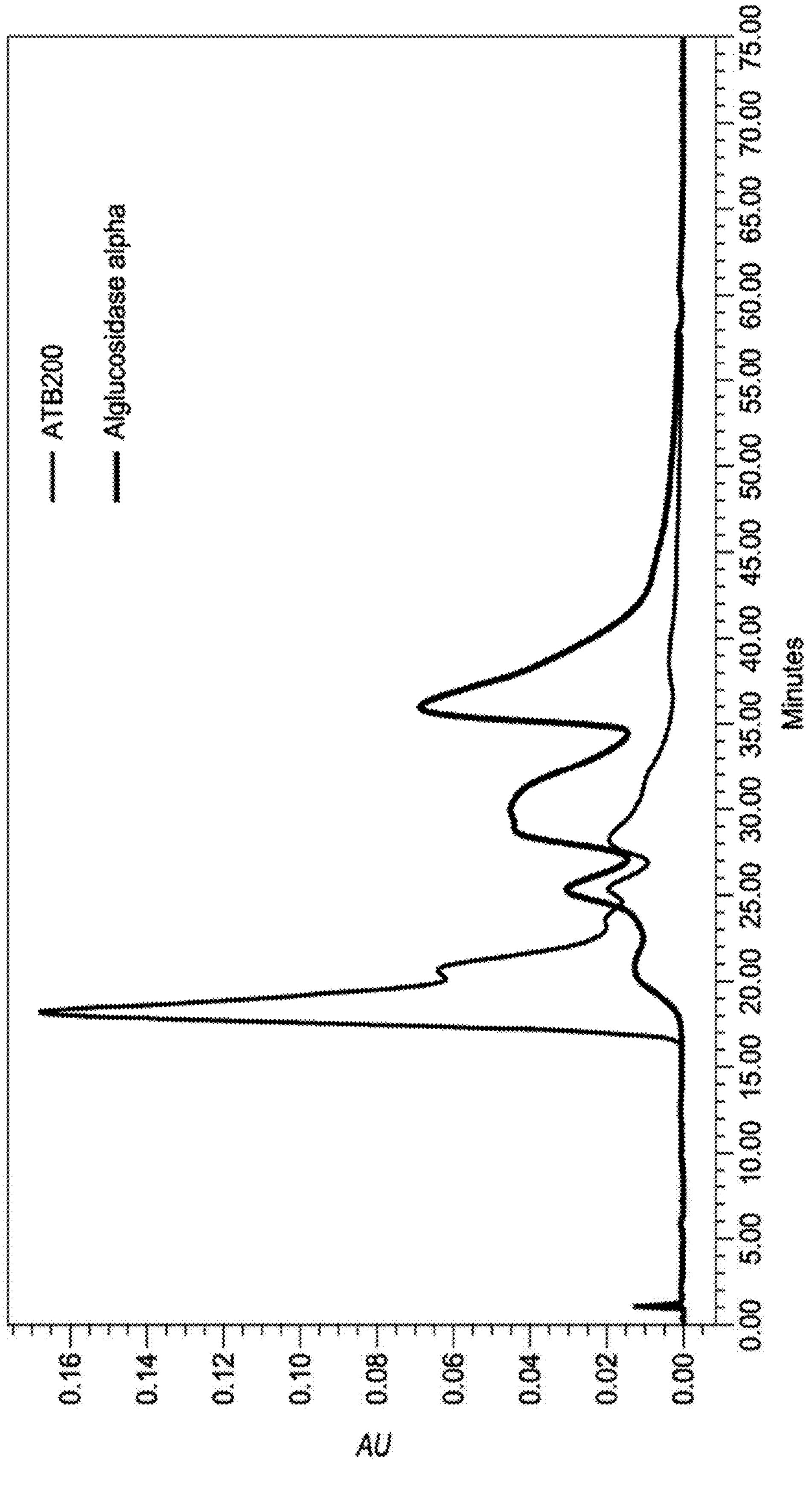
FIG. 9 is a graph showing Polywax elution profiles of Lumizyme® and ATB200 rhGAAs.

Weak anion exchange ("WAX") liquid chromatography was used to fractionate ATB200 rhGAA according to terminal phosphate. Elution profiles were generated by eluting the ERT with increasing amount of salt. The profiles were monitored by UV (A280 nm). ATB200 rhGAA was obtained from CHO cells and purified. Lumizyme® was obtained from a commercial source. Lumizyme® exhibited a high peak on the left of its elution profile. ATB200 rhGAA exhibited four prominent peaks eluting to the right of Lumizyme® (FIG. 9). This confirms that ATB200 rhGAA was phosphorylated to a greater extent than Lumizyme® since this evaluation is by terminal charge rather than CIMPR affinity.

Example 5: Oligosaccharide Characterization of ATB200 rhGAA

Purified ATB200 rhGAA and Lumizyme® glycans were evaluated by MALDI-TOF to determine the individual glycan structures found on each ERT (FIG. 10). ATB200 samples were found to contain lower amounts of non-phosphorylated high-mannose type N-glycans than Lumizyme®. The higher content of M6P glycans in ATB200 than in Lumizyme®, targets ATB200 rhGAA to muscle cells more effectively. The high percentage of mono-phosphorylated and bis-phosphorylated structures determined by MALDI agree with the CIMPR profiles which illustrated significantly greater binding of ATB200 to the CIMPR receptor. N-glycan analysis via MALDI-TOF mass spectrometry confirmed that on average each ATB200 molecule contains at least one natural bis-M6P N-glycan structure. This higher bis-M6P N-glycan content on ATB200 rhGAA directly correlated with high-affinity binding to CIMPR in M6P receptor plate binding assays (KD about 2-4 nM) FIG. 12A.

ATB200 rhGAA was also analyzed for site-specific N-glycan profiles using two different LC-MS/MS analytical techniques. In the first analysis, the protein was denatured, reduced, alkylated and digested prior to LC-MS/MS analysis. During protein denaturation and reduction, 200 μg of protein sample, 5 μL 1 mol/L tris-HCl (final concentration 50 mM), 75 μL 8 mol/L guanidine HCl (final concentration 6 M), 1 μL 0.5 mol/L EDTA (final concentration 5 mM), 2 μL 1 mol/L DTT (final concentration 20 mM) and Milli-Q® water were added to a 1.5 mL tube to provide a total volume of 100 μL. The sample was mixed and incubated at 56° C.

for 30 minutes in a dry bath. During alkylation, the denatured and reduced protein sample was mixed with 5 μL 1 mol/L iodoacetamide (IAM, final concentration 50 mM), then incubated at 10-30° C. in the dark for 30 minutes. After alkylation, 400 μL of precooled acetone was added to the sample and the mixture was frozen at −80° C. refrigeration for 4 hours. The sample was then centrifuged for 5 min at 13000 rpm at 4° C. and the supernatant was removed. 400 μL of precooled acetone was added to the pellets, which was then centrifuged for 5 min at 13000 rpm at 4° C. and the supernatant was removed. The sample was then air dried on ice in the dark to remove acetone residue. 40 μL of 8M urea and 160 μL of 100 mM $NH_4HCO_3$ were added to the sample to dissolve the protein. During trypsin digestion, 50 μg of the protein was then added with trypsin digestion buffer to a final volume of 100 μL, and 5 μL 0.5 mg/mL trypsin (protein to enzyme ratio of 20/1 w/w) was added. The solution was mixed well and incubated overnight (16±2 hours) at 37° C. 2.5 μL 20% TFA (final concentration 0.5%) was added to quench the reaction. The sample was then analyzed using the Thermo Scientific Orbitrap Velos Pro™ Mass Spectrometer.

In the second LC-MS/MS analysis, the ATB200 sample was prepared according to a similar denaturation, reduction, alkylation and digestion procedure, except that iodoacetic acid (IAA) was used as the alkylation reagent instead of IAM, and then analyzed using the Thermo Scientific Orbitrap Fusion Lumos Tribid™ Mass Spectrometer.

The results of the first and second analyses are shown in FIGS. 11A-11H. In FIGS. 11A-11H, the results of the first analysis are represented by left bar (dark grey) and the results from the second analysis are represented by the right bar (light grey). In FIGS. 11B-11G, the symbol nomenclature for glycan representation is in accordance with Varki, A., Cummings, R. D., Esko J. D., et al., *Essentials of Glycobiology,* 2nd edition (2009).

Figure 11A:
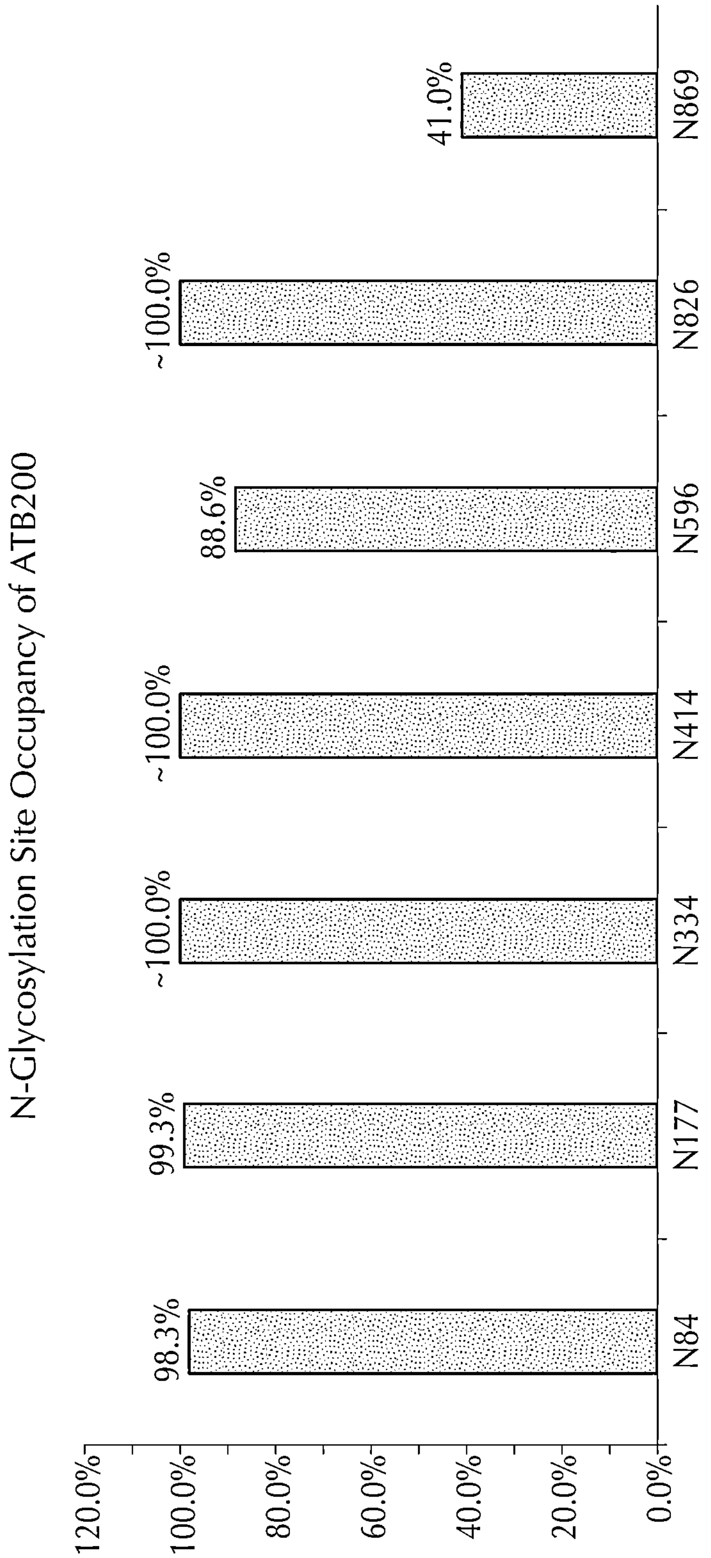
FIGS. 11A-11H show the results of a site-specific N-glycosylation analysis of ATB200 rhGAA.

As can be seen from FIGS. 8A-81, the two analyses provided similar results, although there was some variation between the results. This variation can be due to a number of factors, including the instrument used and the completeness of N-glycan analysis. For example, if some species of phosphorylated glycans were not identified and/or not quantified, then the total number of phosphorylated glycans may be underrepresented, and the percentage of rhGAA bearing the phosphorylated glycans at that site may be underrepresented. As another example, if some species of non-phosphorylated glycans were not identified and/or not quantified, then the total number of non-phosphorylated glycans may be underrepresented, and the percentage of rhGAA bearing the phosphorylated glycans at that site may be overrepresented. FIG. 11A shows the N-glycosylation site occupancy of ATB200. As can be seen from FIG. 11A, the first, second, third, fourth, fifth and sixth N-glycosylation sites are mostly occupied, with both analyses detecting over 90% and up to about 100% of the ATB200 enzyme having a glycan detected at each potential site. However, the seventh potential N-glycosylation site is glycosylated about half of the time.

Figure 11B:
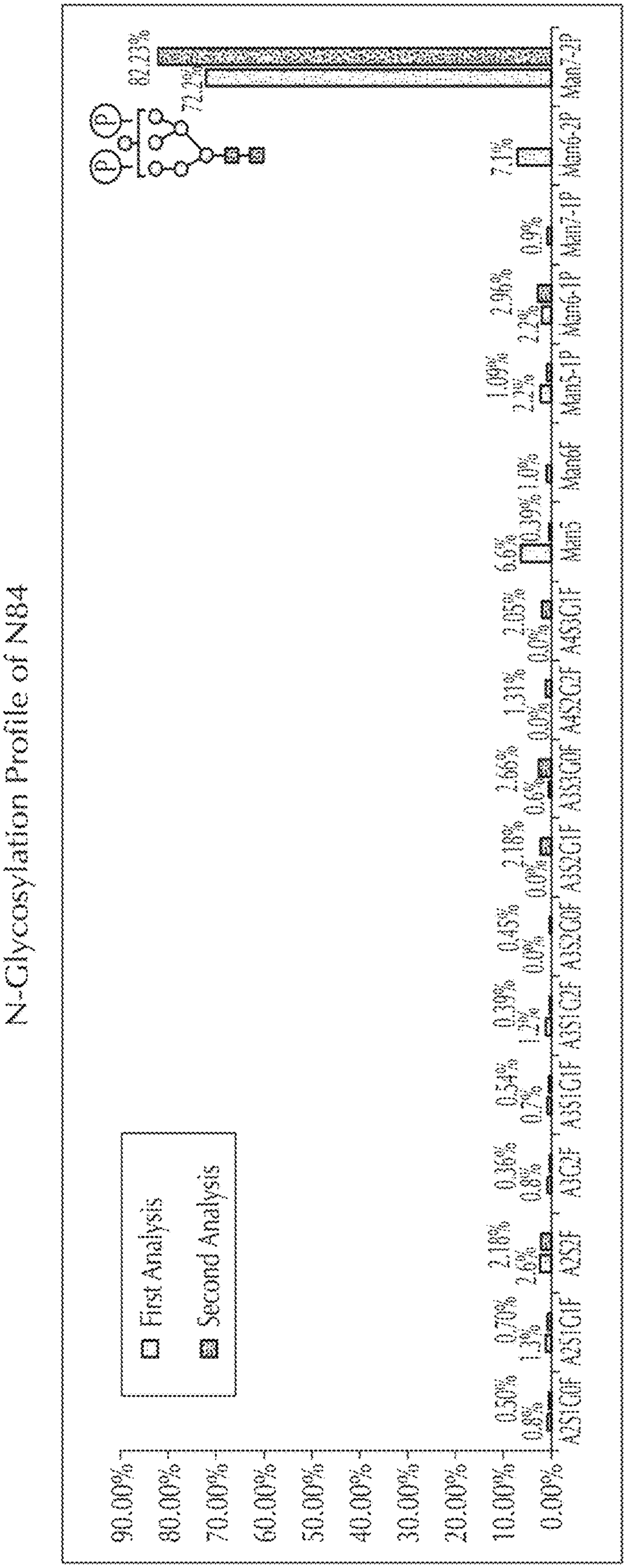

FIG. 11B shows the N-glycosylation profile of the first site, N84. As can be seen from FIG. 11B, the major glycan species is bis-M6P glycans. Both the first and second analyses detected over 75% of the ATB200 had a bis-M6P glycan at the first site.

Figure 11C:
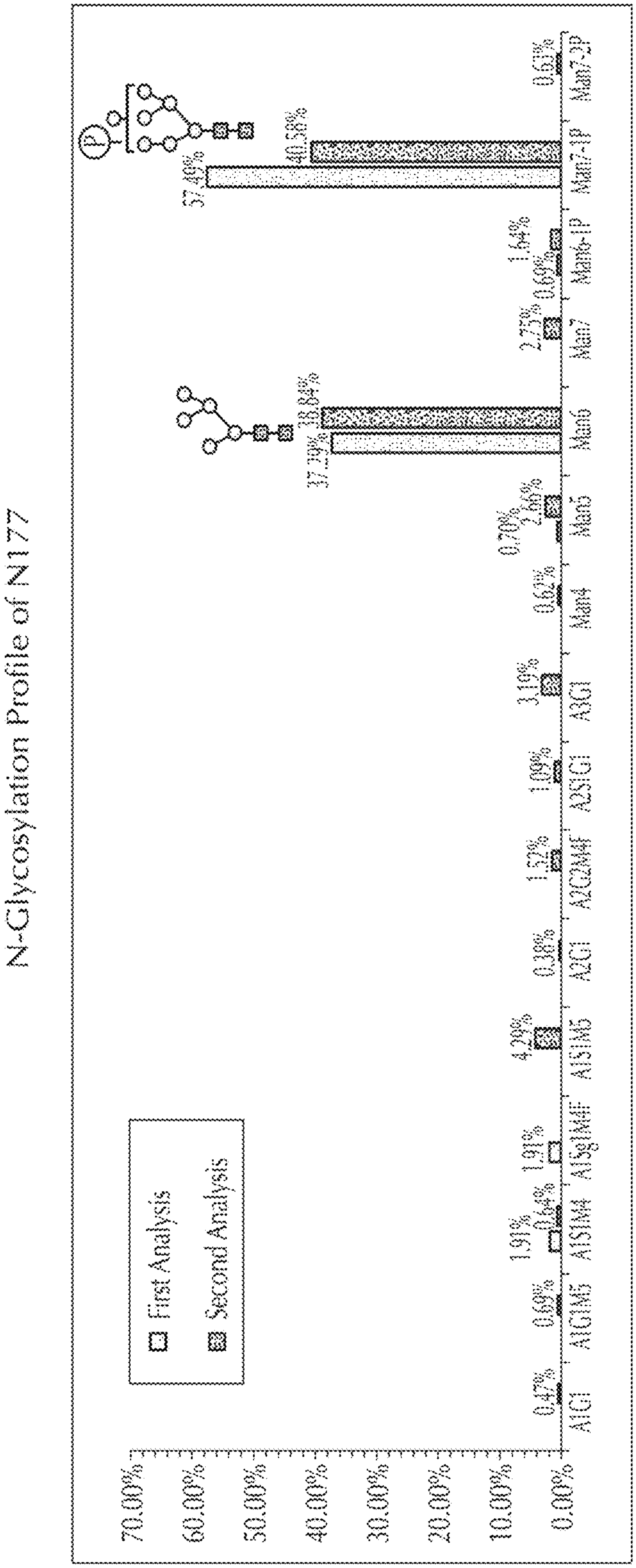

FIG. 11C shows the N-glycosylation profile of the second site, N177. As can be seen from FIG. 11C, the major glycan species are mono-M6P glycans and non-phosphorylated high mannose glycans. Both the first and second analyses detected over 40% of the ATB200 had a mono-M6P glycan at the second site.

Figure 11D:
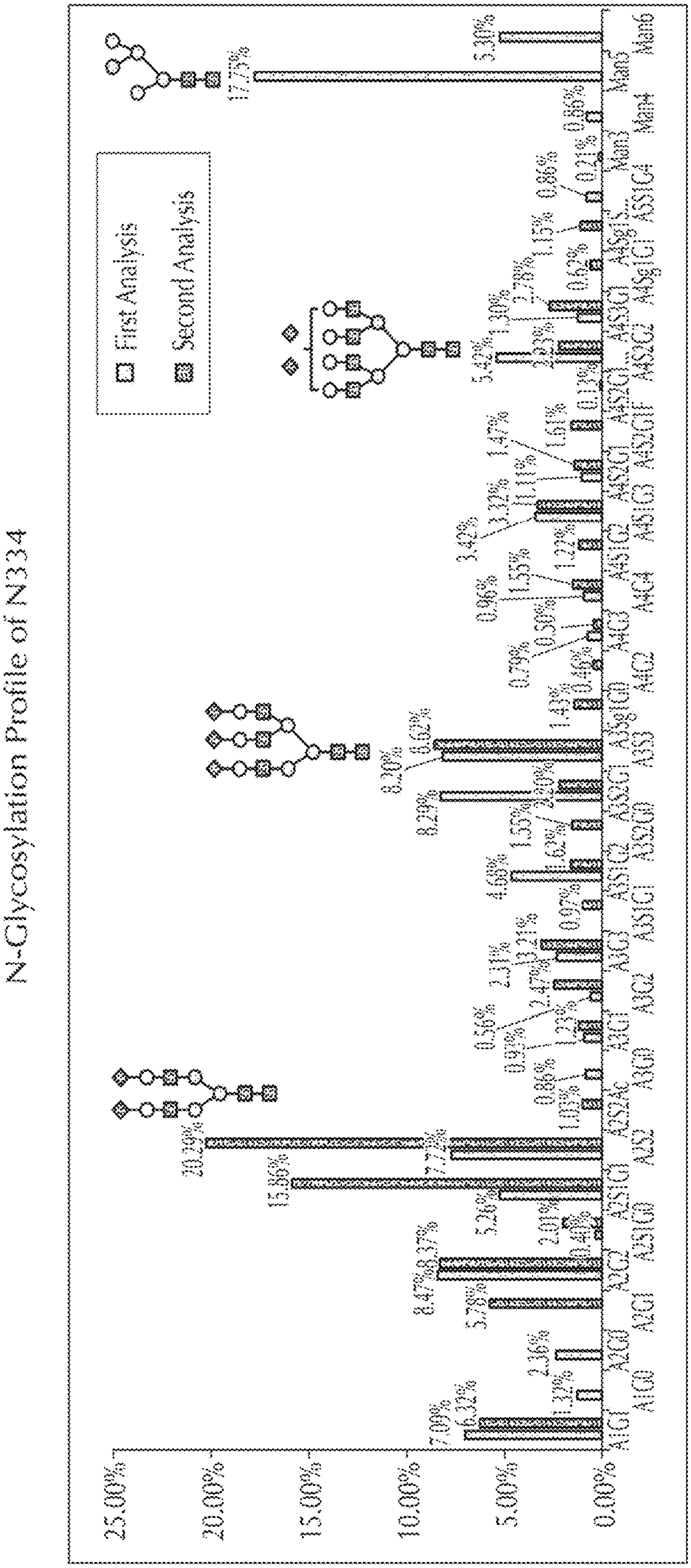

FIG. 11D shows the N-glycosylation profile of the third site, N334. As can be seen from FIG. 11D, the major glycan species are non-phosphorylated high mannose glycans, di-, tri-, and tetra-antennary complex glycans, and hybrid glycans. Both the first and second analyses detected over 20% of the ATB200 had a sialic acid residue at the third site.

Figure 11E:
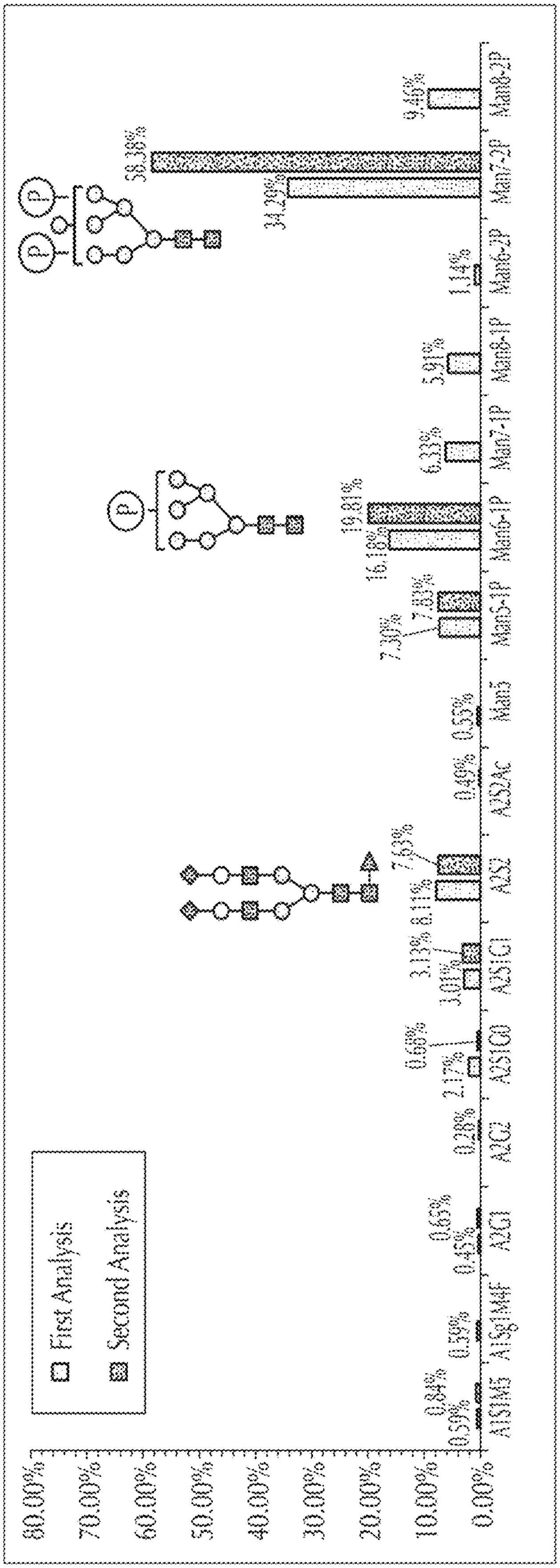

FIG. 11E shows the N-glycosylation profile of the fourth site, N414. As can be seen from FIG. 11E, the major glycan species are bis-M6P and mono-MGP glycans. Both the first and second analyses detected over 40% of the ATB200 had a bis-M6P glycan at the fourth site. Both the first and second analyses also detected over 25% of the ATB200 had a mono-M6P glycan at the fourth site.

Figure 11F:
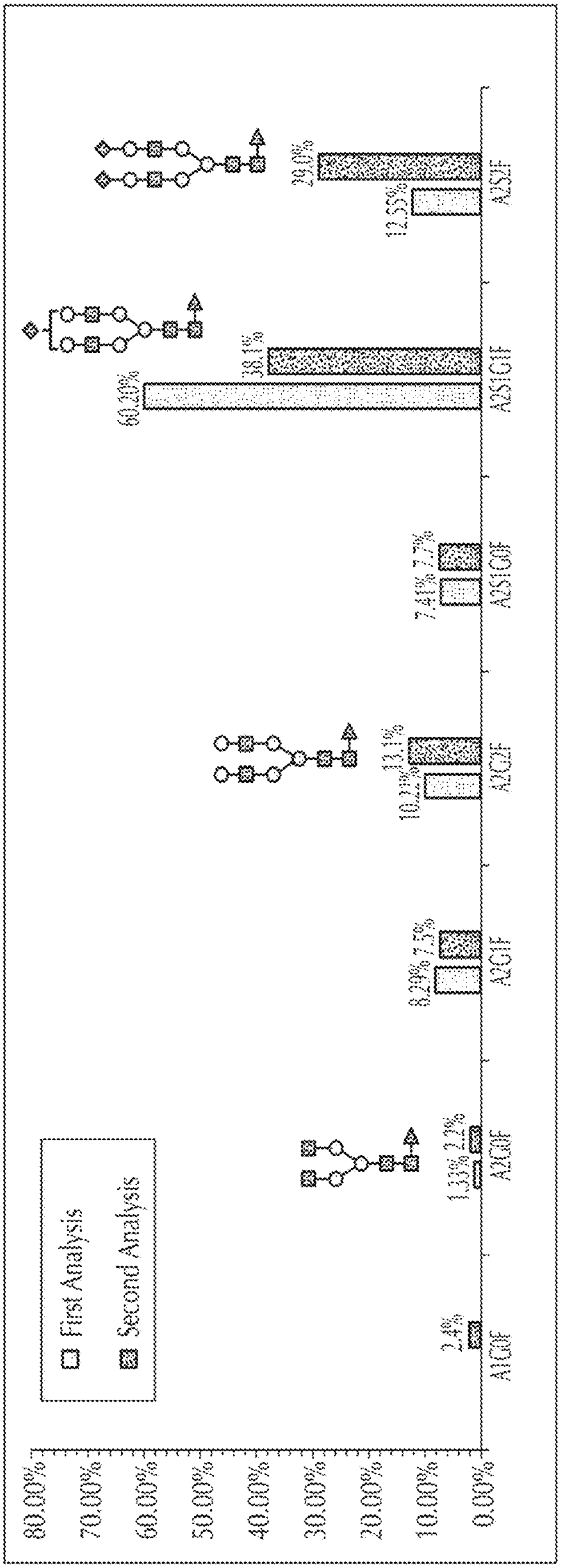

FIG. 11F shows the N-glycosylation profile of the fifth site, N596. As can be seen from FIG. 11F, the major glycan species are fucosylated di-antennary complex glycans. Both the first and second analyses detected over 70% of the ATB200 had a sialic acid residue at the fifth site.

Figure 11G:
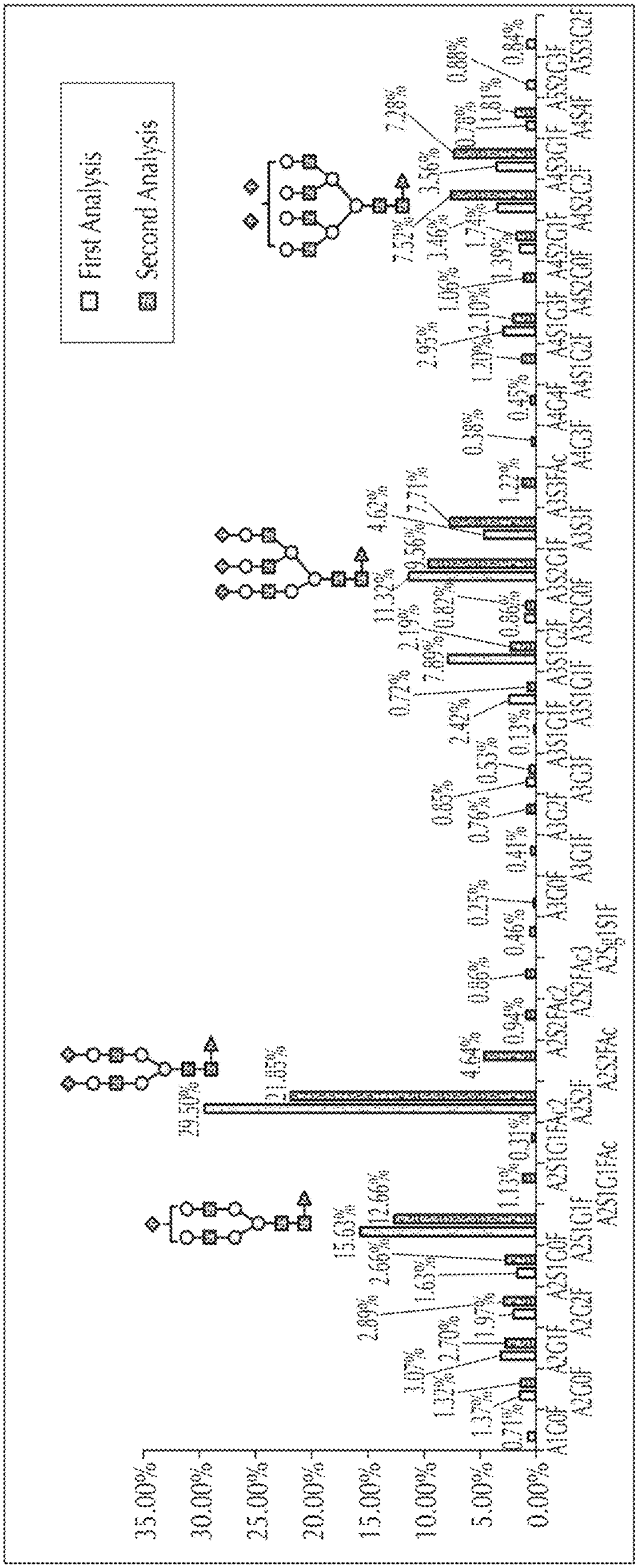

FIG. 11G shows the N-glycosylation profile of the sixth site, N826. As can be seen from FIG. 11G, the major glycan species are di-, tri-, and tetra-antennary complex glycans. Both the first and second analyses detected over 80% of the ATB200 had a sialic acid residue at the sixth site.

An analysis of the glycosylation at the seventh site, N869, showed approximately 40% glycosylation, with the most common glycans being A4S3S3GF (12%), A5S3G2F (10%), A4S2G2F (8%) and A6S3G3F (8%).

Figure 11H:
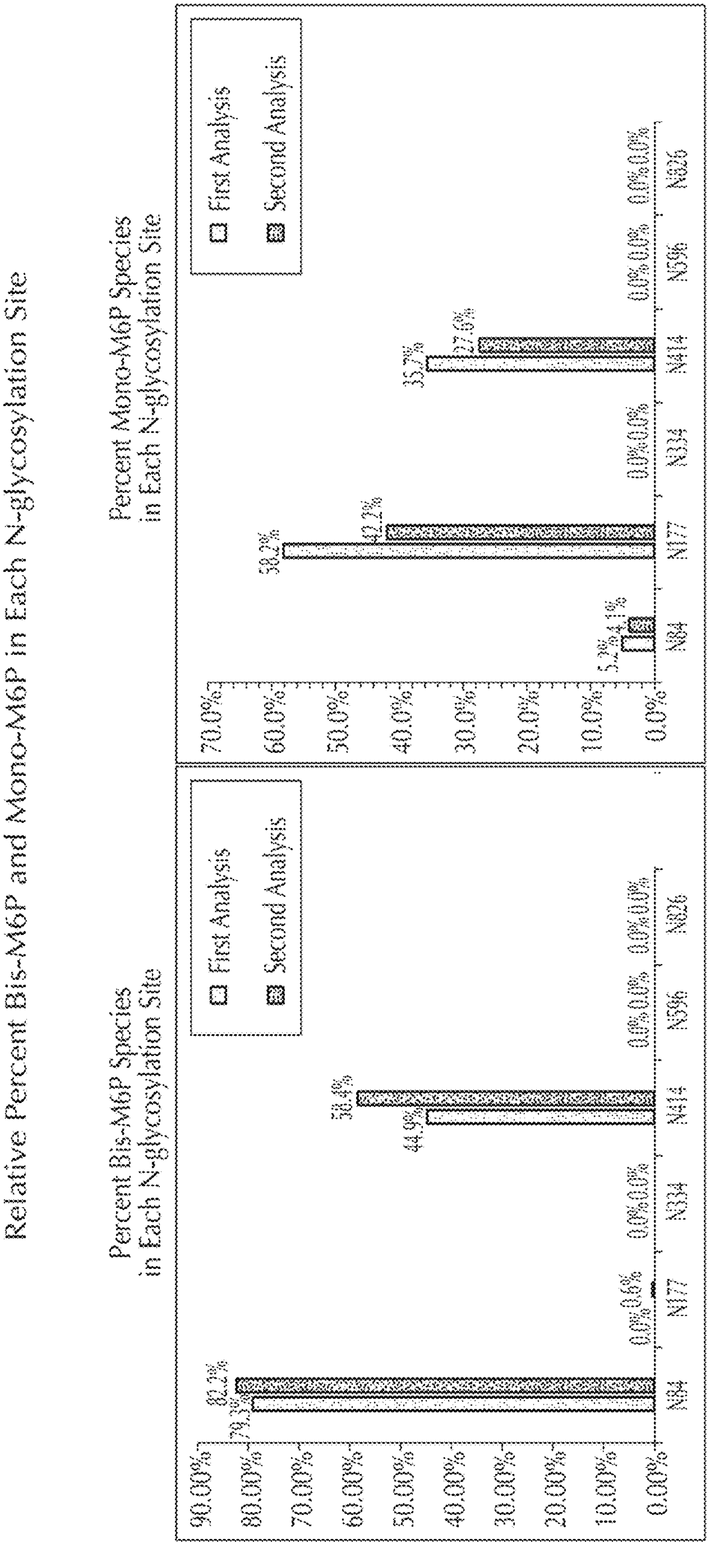

FIG. 11H shows a summary of the phosphorylation at each of the seven potential N-glycosylation sites. As can be seen from FIG. 11H, both the first and second analyses detected high phosphorylation levels at the first, second and fourth sites. Both analyses detected over 80% of the ATB200 was mono- or di-phosphorylated at the first site, over 40% of the ATB200 was mono-phosphorylated at the second site, and over 80% of the ATB200 was mono- or di-phosphorylated at the fourth site.

Another glycan analysis of ATB200 was performed according to a hydrophilic interaction liquid chromatography-fluorescent detection-mass spectrometery (HILIC-FLD-MS) method.

The results of HILIC-FLD-MS analysis are provided in Table 5 below: In Table 5, the first number in the three-digit number indicates the number of branches in the glycan, the second number indicates the number of core fucose units and the third number indicates the number of terminal sialic acid units. Using this nomenclature, "303" represents a tri-antennary glycan (the first 3) with 0 core fucose (the 2nd 0) and 3 terminal sialic acids (the last 3), "212" represents a bi-antennary glycan with 1 core fucose and 2 terminal sialic acids, "404" represents a tetra-antennary glycan with 0 core fucose and 4 terminal sialic acids, etc.

TABLE 5

| FLD Peak Number | MS Peak Number | RT (min) | Glycan Structure | % Peak Area |
|---|---|---|---|---|
| 1 | 1 | | BisP_Man 8 | 2.83% |
| 2 | 2 | 13.41 | BisP_Man 7 | 17.58% |
| | 3 | 14.30 | BisP_Man 6 | 1.02% |
| 3 | 4 | 20.89 | MonoP_Man 6 | 2.34% |
| 4 | 5 | 21.65 | MonoP_Man 5 | 1.16% |
| 5 | 6 | 23.51 | MonoP_Man 8 | 1.28% |

TABLE 5-continued

| FLD Peak Number | MS Peak Number | RT (min) | Glycan Structure | % Peak Area |
|---|---|---|---|---|
| 6 | 7 | 24.33 | MonoP_Man 7 | 4.35% |
| 7 | 8 | 25.61 | MonoP_Man 7_(+)GlcNAc | 0.50% |
| 8 | 9 | 28.76 | MonoP_hMan6_101 | 0.48% |
| 9 | 10 | 30.54 | MonoP_Man 6_(+)GlcNAc | 0.68% |
| 10 | 11 | 33.50 | Man 6 | 3.97% |
| | 12 | 33.65 | 303 | 0.74% |
| 11 | 13 | 34.97 | Man 7 | 0.20% |
| 12 | 14 | 35.64 | 403 | 0.39% |
| 13 | 15 | 36.61 | 302 | 0.36% |
| 14 | 16 | 38.07 | 302 | 0.61% |
| 15 | 17 | 38.53 | Man 5 | 1.85% |
| 16 | 18 | 39.57 | 302 | 0.48% |
| | 19 | 39.78 | hMan 5_101 | 0.42% |
| | 20 | 40.05 | hMan 5_100_(−)Gal | 0.30% |
| 17 | 21 | 40.77 | 301_(−)Gal | 0.52% |
| | 22 | 40.58 | 301 | 0.50% |
| 18 | 23 | 41.47 | 300_(−)Gal | 0.80% |
| 19 | 24 | 42.17 | 301_(−)Gal | 0.11% |
| | 25 | 42.13 | 301 | 0.58% |
| 20 | 26 | 42.89 | 301_(−)Gal | 0.07% |
| | 27 | 42.79 | 301 | 0.80% |
| 21 | 28 | 43.41 | 300 | 0.85% |
| | 29 | 43.28 | 101 | 0.39% |
| 22 | 30 | 43.94 | 202 | 0.63% |
| 23 | 31 | 44.45 | 401 | 0.39% |
| 24 | 32 | 45.04 | MonoP_hMan6_111 | 0.36% |
| 25 | 33 | 45.69 | MonoP_hMan6_111 | 1.45% |
| | 34 | 45.90 | 100 | 0.23% |
| | 35 | 45.90 | 400 | 0.19% |
| 26 | 36 | 46.87 | 201 | 0.49% |
| | 37 | 47.15 | 202 | 0.34% |
| 27 | 38 | 48.19 | 414 | 0.37% |
| 28 | 39 | 48.94 | 202 | 1.97% |
| 29 | 40 | 50.79 | MonoP_Man 6_110_(−)Gal | 1.31% |
| | 41 | 51.37 | 414 | 0.62% |
| 30 | 42 | 52.22 | 313 | 0.74% |
| | 43 | 52.42 | 201_(−)Gal | 0.46% |
| | 44 | 52.42 | 201 | 1.18% |
| | 45 | 53.11 | hMan6_111 | 0.20% |
| 31 | 46 | 53.83 | 200_(−)Gal | 0.80% |
| | 47 | 54.23 | 201 | 1.27% |
| | 48 | 54.75 | 413 | 0.30% |
| 32 | 49 | 55.47 | 200 | 1.30% |
| 33 | 50 | 57.45, 58.34 | 414_(+)GlcNAcGal | 0.14% |
| | 51 | 56.62, 56.91, 57.99 | 413 | 0.94% |
| | 52 | 56.11, 57.26, 57.99 | 312 | 0.98% |
| 34 | 53 | 60.19 | 413 | 0.33% |
| | 54 | 59.39 | 413_(+)GlcNAcGal | 0.42% |
| | 55 | 59.80 | 312 | 0.52% |
| | 56 | 59.49 | 412 | 0.18% |
| 35 | 57 | 60.75 | 413 | 0.78% |
| | 58 | 60.89 | 413_(+)GlcNAcGal | 0.07% |
| 36 | 59 | 61.79 | 413 | 0.20% |
| | 60 | 61.75 | 312 | 0.16% |
| | 61 | 62.12 | 412 | 0.64% |
| 37 | 62 | 63.87 | 311 | 0.73% |
| | 63 | 63.18, 64.32 | 412 | 0.29% |
| | 64 | 63.84 | 413_(+)GlcNAcGal | 0.45% |
| | 65 | 63.5, 64.36 | 311_(−)Gal | 0.42% |
| 38 | 66 | 65.73, 66.20 | 311 | 0.68% |
| | 67 | 65.85, 66.49 | 412 | 0.72% |
| | 68 | 65.91 | 310_(−)Gal | 0.28% |
| 39 | 69 | 67.37 | 212 | 1.42% |
| | 70 | 67.57 | 310 | 0.34% |
| 40 | 71 | 68.67 | 412_(+)GlcNAcGal | 0.24% |
| | 72 | 68.36 | 412 | 0.53% |
| 41 | 73 | 68.36 | 412_(+)GlcNAcGal | 0.17% |
| | 74 | 69.03 | 412 | 0.35% |
| | 75 | 69.30 | 413_(+)2(GlcNAcGal) | 0.16% |
| 42 | 76 | 70.66 | 412_(+)GlcNAcGal | 0.73% |
| 43 | 77 | 71.74 | 211 | 1.09% |
| | 78 | 71.23 | 211_(−)Gal | 0.19% |
| 44 | 79 | 72.46 | 212 | 3.66% |

TABLE 5-continued

| FLD Peak Number | MS Peak Number | RT (min) | Glycan Structure | % Peak Area |
|---|---|---|---|---|
| 45 | 80 | 74.82 | 221_(−)Gal(+)GalNAc | 0.38% |
| | 81 | 74.43, 74.96 | 411_(+)GlcNAcGal | 0.66% |
| 46 | 82 | 75.92 | 410 | 0.42% |
| 47 | 83 | 76.73, 77.87 | 211_(−)Gal | 1.24% |
| | 84 | 77.23 | 211 | 3.64% |
| 48 | 85 | 79.05 | 211 | 1.52% |
| | 86 | 79.38 | 210_(−)2Gal | 0.45% |
| 49 | 87 | 80.11 | 210_(−)Gal | 1.58% |
| 50 | 88 | 81.15 | 210 | 2.41% |
| 51 | 89 | 84.22-87.15 | 311 | 1.26% |
| 52 | 90 | 95.35 | Mono_Acetyl_NANA_212 | 0.99% |
| 53 | 91 | 96.23 | Mono_Acetyl_NANA_211 | 0.76% |
| 54 | 92 | 97.37 | Bis_Acetyl_NANA_212 | 0.42% |

Based on this HILIC-FLD-MS analysis, the ATB200 tested is expected to have an average fucose content of 2-3 mol per mol of ATB200, GlcNAc content of 20-25 mol per mol of ATB200, galactose content of 8-12 mol per mol of ATB200, mannose content of 22-27 mol per mol of ATB200, M6P content of 3-5 mol per mol of ATB200 and sialic acid content of 4-7 mol of ATB200.

Example 6: Characterization of CIMPR Affinity of ATB200

Figures 12A, 12B:
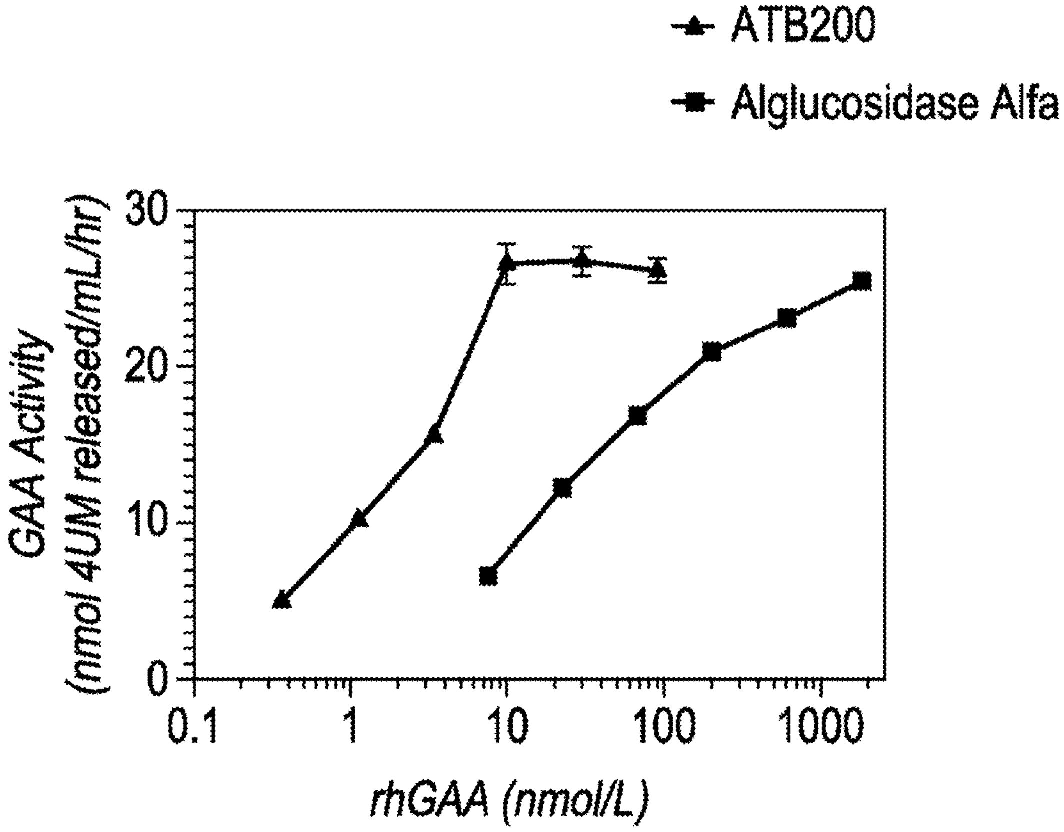
FIG. 12A is a graph comparing the CIMPR binding affinity of ATB200 rhGAA (left trace) with that of Lumizyme® (right trace).
FIG. 12B is a table comparing the Bis-M6P content of Lumizyme® and ATB200 rhGAA.

In addition to having a greater percentage of rhGAA that can bind to the CIMPR, it is important to understand the quality of that interaction. Lumizyme® and ATB200 rhGAA receptor binding was determined using a CIMPR plate binding assay. Briefly, CIMPR-coated plates were used to capture GAA. Varying concentrations of rhGAA were applied to the immobilized receptor and unbound rhGAA was washed off. The amount of remaining rhGAA was determined by GAA activity. As shown by FIG. 12A, ATB200 rhGAA bound to CIMPR significantly better than Lumizyme®.

FIG. 12B shows the relative content of bis-M6P glycans in Lumizyme®, a conventional rhGAA, and ATB200 according to the invention. For Lumizyme® there is on average only 10% of molecules have a bis-phosphorylated glycan. Contrast this with ATB200 where on average every rhGAA molecule has at least one bis-phosphorylated glycan.

Example 7: ATB200 rhGAA was More Efficiently Internalized by Fibroblast than Lumizyme The relative cellular uptake of ATB200 and Lumizyme® rhGAA were compared using normal and Pompe fibroblast cell lines. Comparisons involved 5-100 nM of ATB200 rhGAA according to the invention with 10-500 nM conventional rhGAA Lumizyme®. After 16-hr incubation, external rhGAA was inactivated with TRIS base and cells were washed 3-times with PBS prior to harvest. Internalized GAA measured by 4MU-a-Glucoside hydrolysis and was graphed relative to total cellular protein and the results appear in FIGS. 13A-B.

ATB200 rhGAA was also shown to be efficiently internalized into cells (FIGS. 13A and 13B), respectively, show that ATB200 rhGAA is internalized into both normal and Pompe fibroblast cells and that it is internalized to a greater degree than conventional Lumizyme® rhGAA. ATB200 rhGAA saturates cellular receptors at about 20 nM, while about 250 nM of Lumizyme® is needed. The uptake efficiency constant ($K_{uptake}$) extrapolated from these results is 2-3 nm for ATB200 and 56 nM for Lumizyme® as shown by FIG. 13C. These results suggest that ATB200 rhGAA is a well-targeted treatment for Pompe disease.

Example 8: Glycogen Reduction in Gaa-Knockout Mice

Figure 14A:
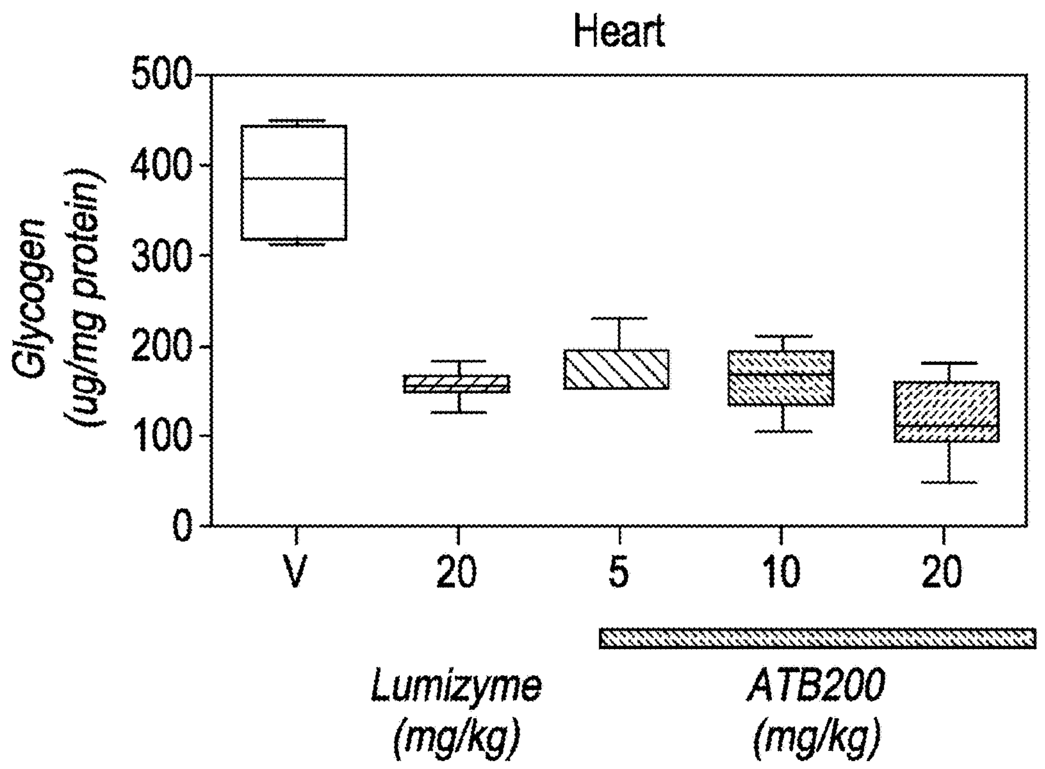
FIG. 14A is a graph showing the amount of glycogen relative to dose of recombinant human acid α-glucosidase in mouse heart muscle after contact with vehicle (negative control), with 20 mg/ml alglucosidase alfa (Lumizyme®), or with 5, 10 or 20 mg/kg ATB200.
Figure 14B:
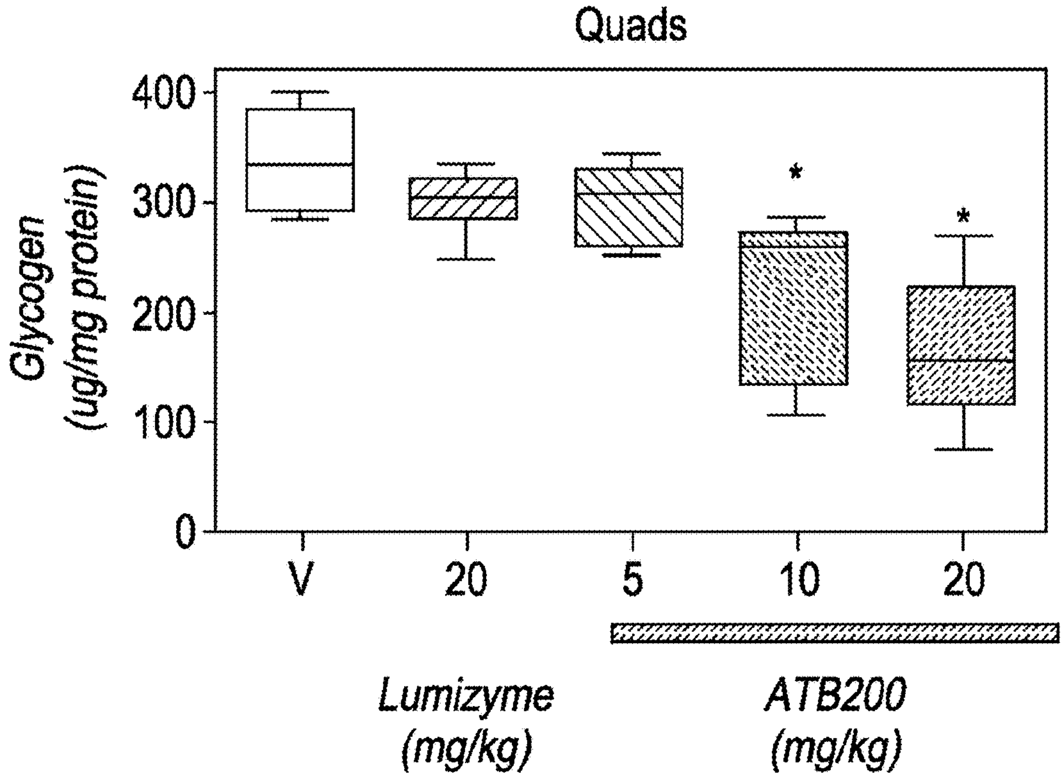
FIG. 14B is a graph showing the amount of glycogen relative to dose of recombinant human acid α-glucosidase in mouse quadriceps muscle after contact with vehicle (negative control), with 20 mg/ml alglucosidase alfa (Lumizyme®), or with 5, 10 or 20 mg/kg ATB200.
Figures 14C, 15:
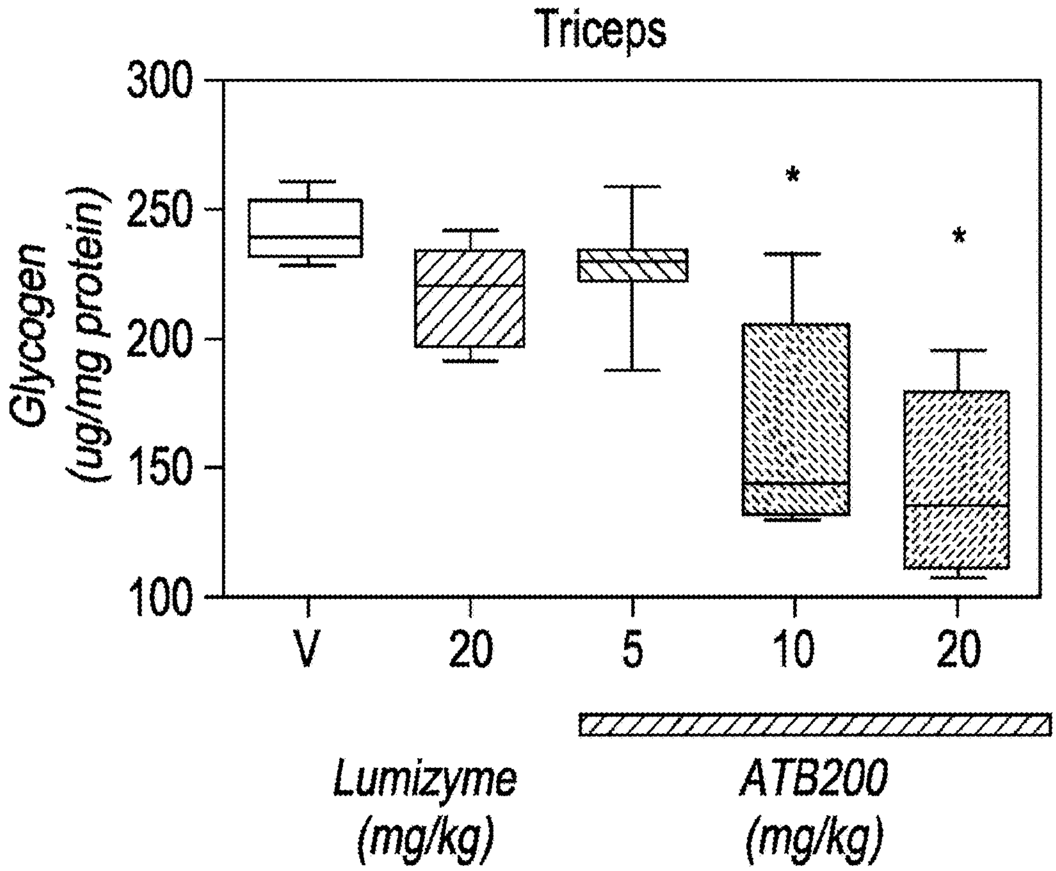
FIG. 14C is a graph showing the amount of glycogen relative to dose of recombinant human acid α-glucosidase in mouse triceps muscle after contact with vehicle (negative control), with 20 mg/ml alglucosidase alfa (Lumizyme®), or with 5, 10 or 20 mg/kg ATB200.
FIG. 15 is a table showing that the combination of ATB200 rhGAA and chaperone miglustat provided significantly better glycogen clearance in GAA knock-out mice than treatments with either Lumizyme® or ATB200 rhGAAs without the miglustat chaperone.

FIGS. 14A to 14C show the effects of administering alglucosidase alfa (Lumizyme®) and ATB200 on glycogen clearance in Gaa knockout mice. Animals were given two IV bolus administrations (every other week); tissues were harvested two weeks after the last dose and analyzed for acid α-glucosidase activity and glycogen content.

As seen from FIGS. 14A to 14C, ATB200 was found to deplete tissue glycogen in acid α-glucosidase (Gaa) knockout mice in a dose-dependent fashion. The 20 mg/kg dose of ATB200 consistently removed a greater proportion of stored glycogen in Gaa knockout mice than the 5 and 10 mg/kg dose levels. However, as seen in FIGS. 14A to 14C, ATB200 administered at 5 mg/kg showed a similar reduction of glycogen in mouse heart and skeletal muscles (quadriceps and triceps) to Lumizyme® administered at 20 mg/kg, while ATB200 dosed at 10 and 20 mg/kg showed significantly better reduction of glycogen levels in skeletal muscles than Lumizyme®.

FIG. 15 shows the effects of administering alglucosidase alfa (Lumizyme®) and ATB200 on glycogen clearance in Gaa knockout mice, as well as the effect of co-administration of ATB200 and miglustat on glycogen clearance. Twelve week old GAA KO mice treated with Lumizyme® or ATB200, 20 mg/kg IV every other week 4 injections; miglustat was co-administered at 10 mg/kg PO, 30 min prior to rhGAA as indicated. Tissues were collected 14 days after last enzyme dose for glycogen measurement. FIG. 15 shows the relative reduction of glycogen in quadriceps and triceps skeletal muscle, with ATB200 providing a greater reduction of glycogen than Lumizyme®, and ATB200/miglustat providing an even greater reduction of glycogen.

Example 9: Muscle Physiology and Morphology in Gaa-Knockout Mice

Gaa knockout mice were given two IV bolus administrations of recombinant human acid α-glucosidase (alglucosidase alfa or ATB200) at 20 mg/kg every other week. Miglustat was orally administered at dosages of 10 mg/kg to a subset of animals treated with ATB200 30 mins prior to administration of ATB200. Control mice were treated with vehicle alone. Soleus, quadriceps and diaphragm tissue is harvested two weeks after the last dose of recombinant human acid α-glucosidase. Soleus and diaphragm tissue were analyzed for glycogen levels, by staining with periodic acid-Schiff reagent (PAS), and for lysosome proliferation, by measuring levels of the lysosome-associated membrane protein (LAMP1) marker, which is upregulated in Pompe disease. Semi-thin sections of quadriceps muscle embedded in epoxy resin (Epon) were stained with methylene blue and observed by electron microscopy (1000×) to determine the extent of the presence of vacuoles. Quadriceps muscle samples were analyzed immunohistochemically to determine levels of the autophagy markers microtubule-associated protein 1A/1B-light chain 3 phosphatidylethanolamine conjugate (LC3A II) and p62, the insulin-dependent glucose transporter GLUT4 and the insulin-independent glucose transporter GLUT1.

In a similar study, Gaa knockout mice were given four IV bolus administrations of recombinant human acid α-glucosidase (alglucosidase alfa or ATB200) at 20 mg/kg every other week. Miglustat was orally administered at dosages of 10 mg/kg to a subset of animals treated with ATB200 30 mins prior to administration of ATB200. Control mice were treated with vehicle alone. Cardiac muscle tissue was harvested two weeks after the last dose of recombinant human acid α-glucosidase and analyzed for glycogen levels, by staining with periodic acid-Schiff reagent (PAS), and for lysosome proliferation, by measuring levels of LAMP1.

Figure 16:
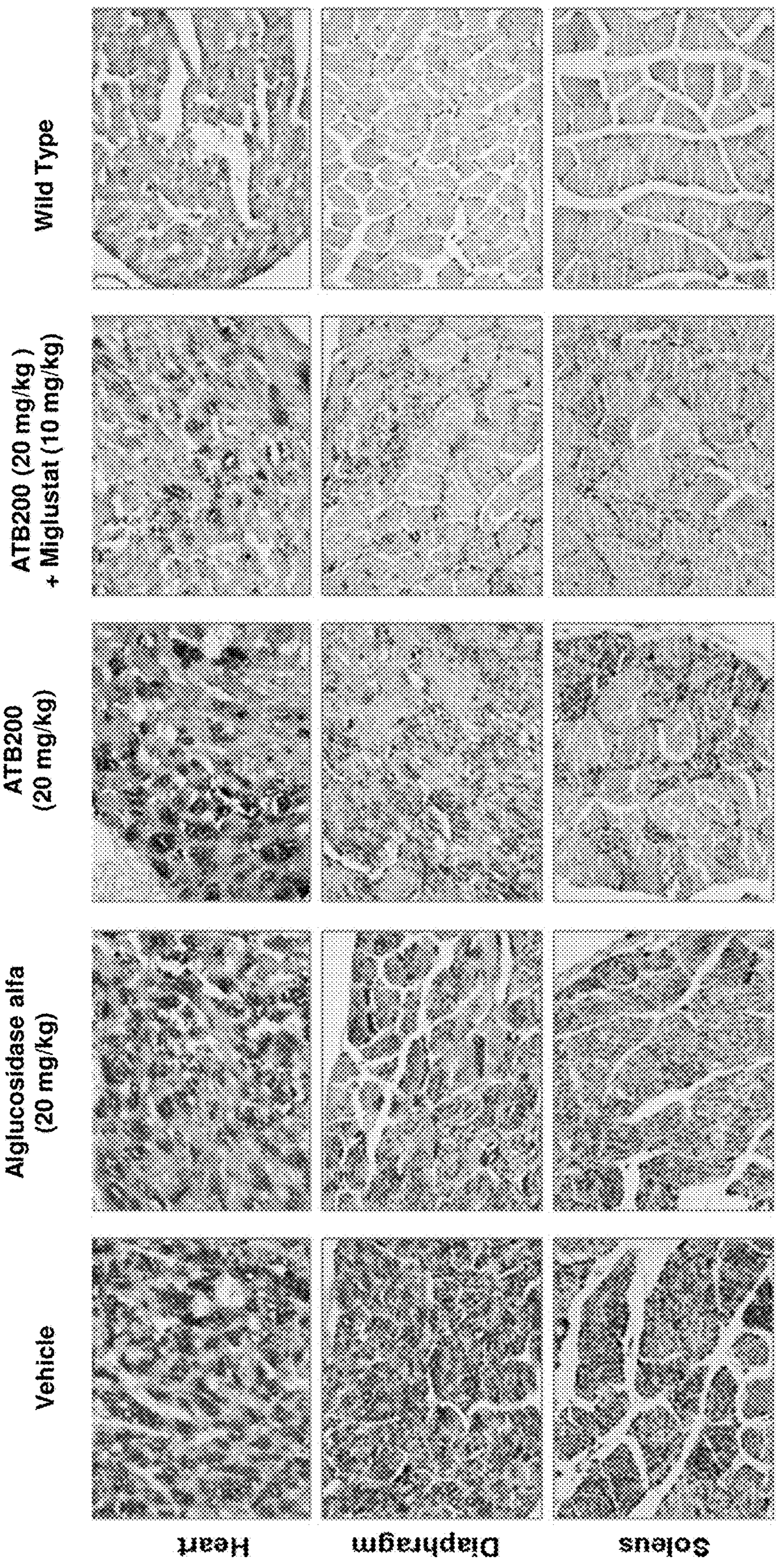
FIG. 16 is a series of electron micrographs of heart, diaphragm and soleus muscle from wild-type and Gaa-knockout mice treated with vehicle, alglucosidase alfa and ATB200 in the presence and absence of miglustat, showing levels of lysosome associated membrane protein (LAMP-1).
Figure 17:
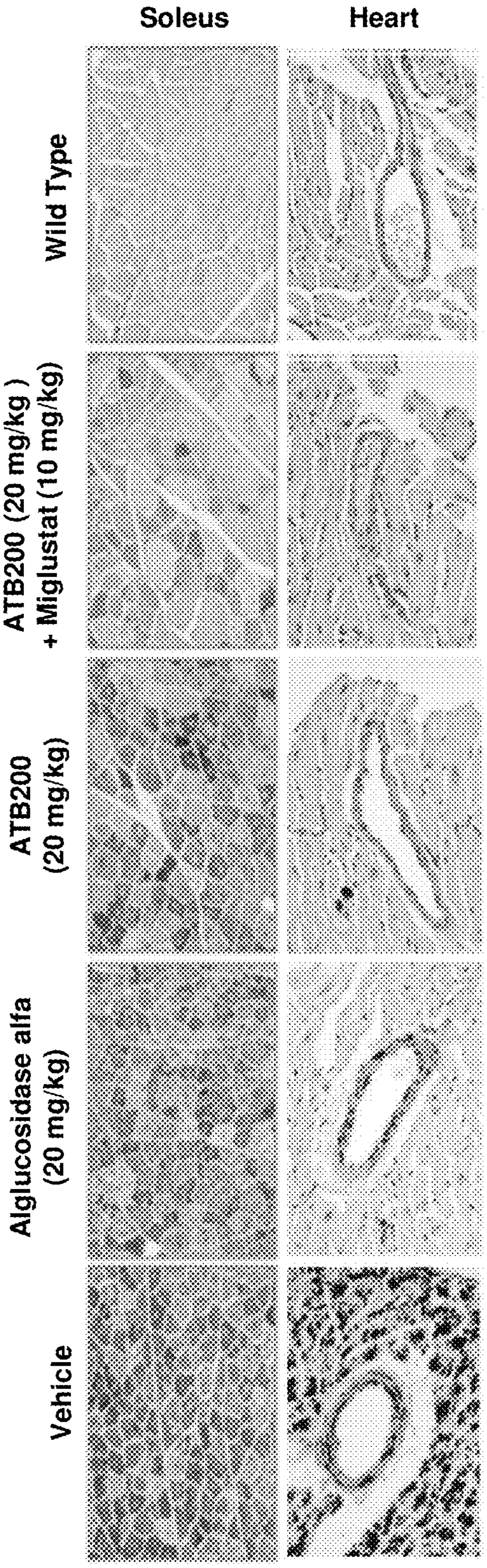
FIG. 17 is a series of electron micrographs of heart and soleus muscle from wild-type and Gaa-knockout mice treated with vehicle, alglucosidase alfa and ATB200 in the presence and absence of miglustat, showing glycogen levels by staining with periodic acid-Schiff reagent (PAS).

As seen in FIG. 16, administration of ATB200 showed a reduction in lysosome proliferation in heart, diaphragm and skeletal muscle (soleus) tissue compared to conventional treatment with alglucosidase alfa, and co-administration of miglustat with ATB200 showed a significant further reduction in lysosomal proliferation, approaching the levels seen in wild type (WT) mice. In addition, as seen in FIG. 17, administration of ATB200 showed a reduction in punctate glycogen levels in heart and skeletal muscle (soleus) tissue compared to conventional treatment with alglucosidase alfa, and co-administration of miglustat with ATB200 showed a significant further reduction, again approaching the levels seen in wild type (WT) mice.

Figure 18:
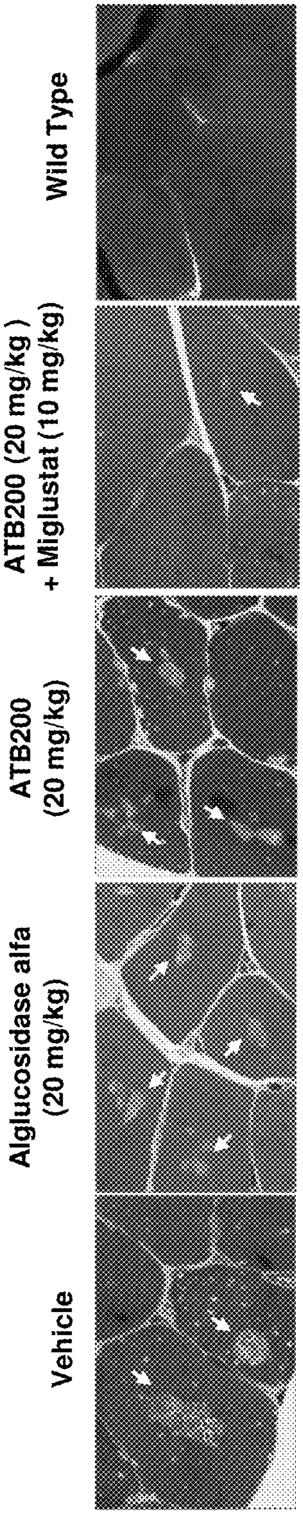
FIG. 18 is a series of electron micrographs (1000×) of quadriceps muscle from wild-type and Gaa-knockout mice treated with vehicle, alglucosidase alfa and ATB200 in the presence and absence of miglustat, stained with methylene blue to show vacuoles (indicated by arrows).
Figure 19:
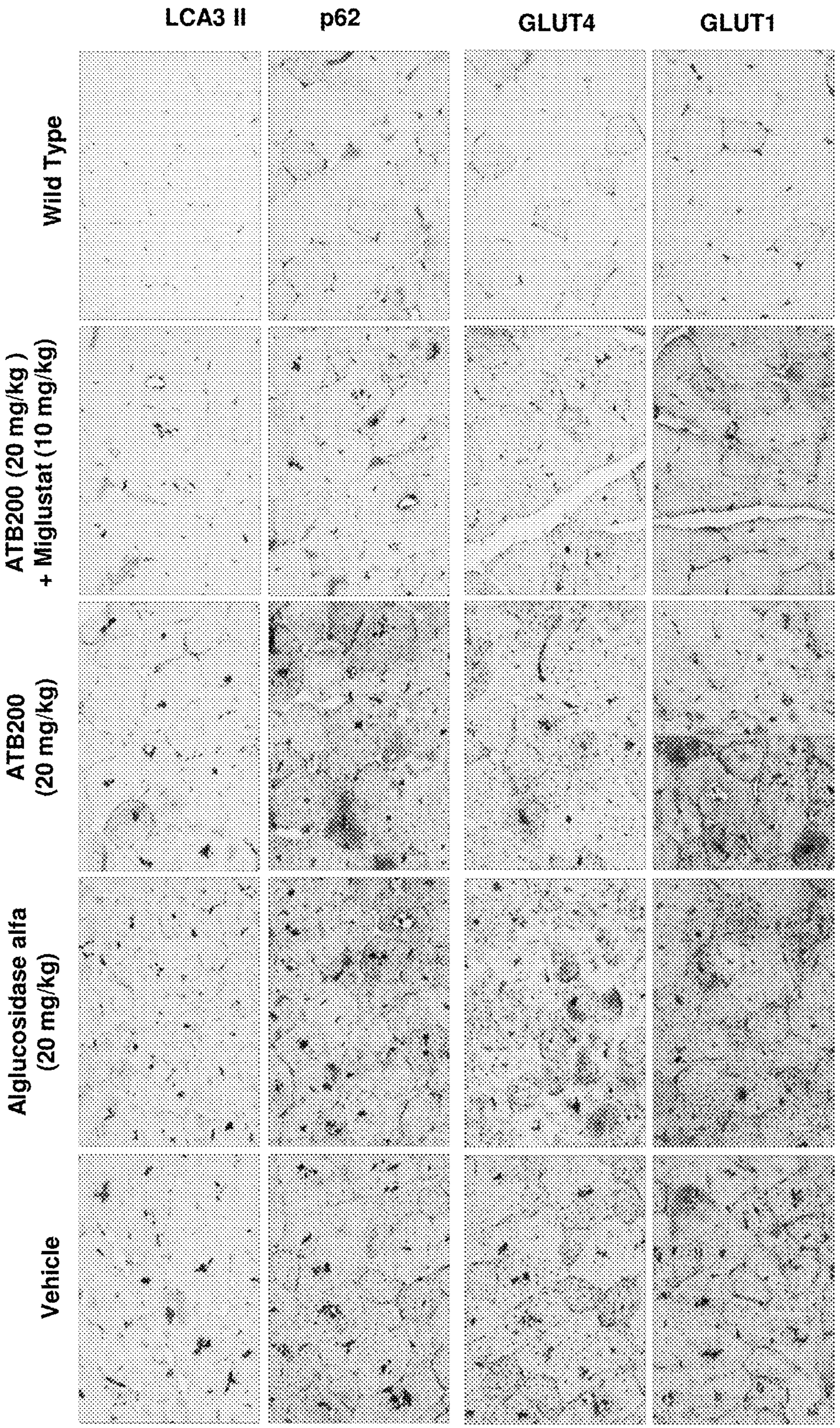
FIG. 19 is a series of electron micrographs (40×) of quadriceps muscle from wild-type and Gaa-knockout mice treated with vehicle, alglucosidase alfa and ATB200 in the presence and absence of miglustat, showing levels of the autophagy markers microtubule-associated protein 1A/1B-light chain 3 phosphatidylethanolamine conjugate (LC3A II) and p62, the insulin-dependent glucose transporter GLUT4 and the insulin-independent glucose transporter GLUT1.

As well, as seen in FIG. 18, co-administration of miglustat with ATB200 significantly reduced the number of vacuoles in muscle fiber in the quadriceps of Gaa knockout mice compared to untreated mice and mice treated with alglucosidase alfa. As seen in FIG. 19, levels of both LC3 II and p62 are increased in Gaa knockout mice compared to wild type mice, but are reduced significantly upon treatment with ATB200 and miglustat, indicating that the increase in autophagy associated with acid α-glucosidase deficiency is reduced upon co-administration of ATB200 and miglustat. In addition, levels of the insulin-dependent glucose transporter GLUT4 and the insulin-independent glucose transporter GLUT1 are increased in Gaa knockout mice compared to wild type mice, but again, are reduced significantly upon treatment with ATB200 and miglustat. The elevated GLUT4 and GLUT1 levels associated with acid α-glucosidase deficiency can contribute to increased glucose uptake into muscle fibers and increased glycogen synthesis both basally and after food intake. Thus, combination treatment with ATB200 and miglustat has been found to improve skeletal muscle morphology and physiology in a mouse model of Pompe disease.

Example 10: Muscle Function in Gaa-Knockout Mice

Figure 21A:
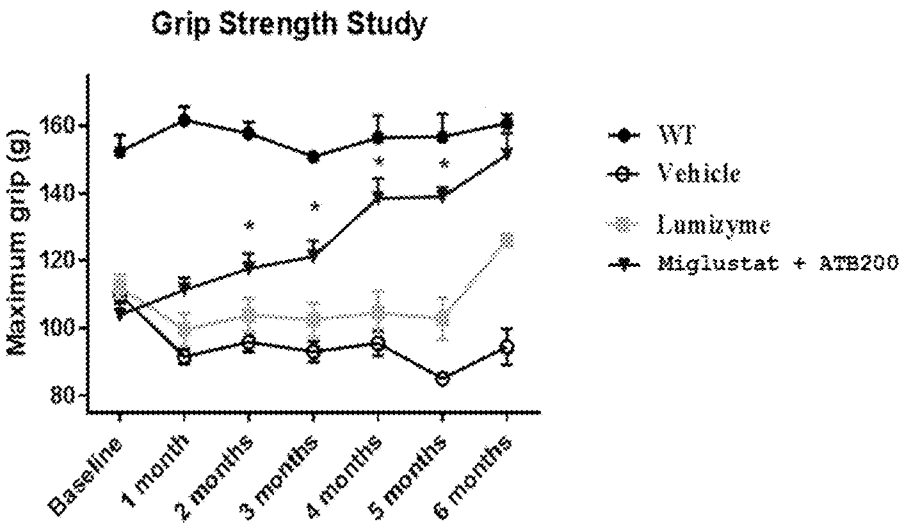
FIGS. 21A and 21B are graphs showing wire hand and grip strength muscle data for wild-type and Gaa-knockout mice treated with vehicle, alglucosidase alfa and ATB200 in the presence of miglustat.
Figure 21B:
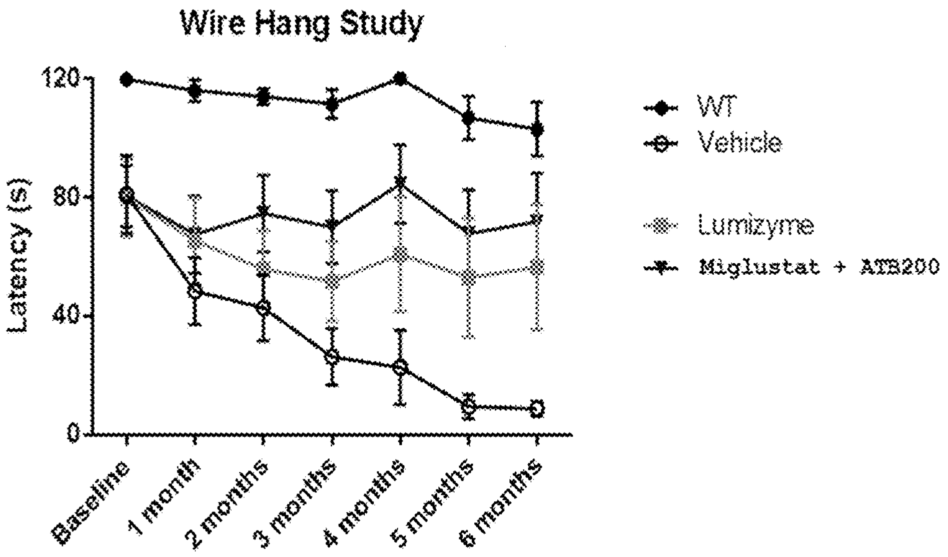
Figure 22A:
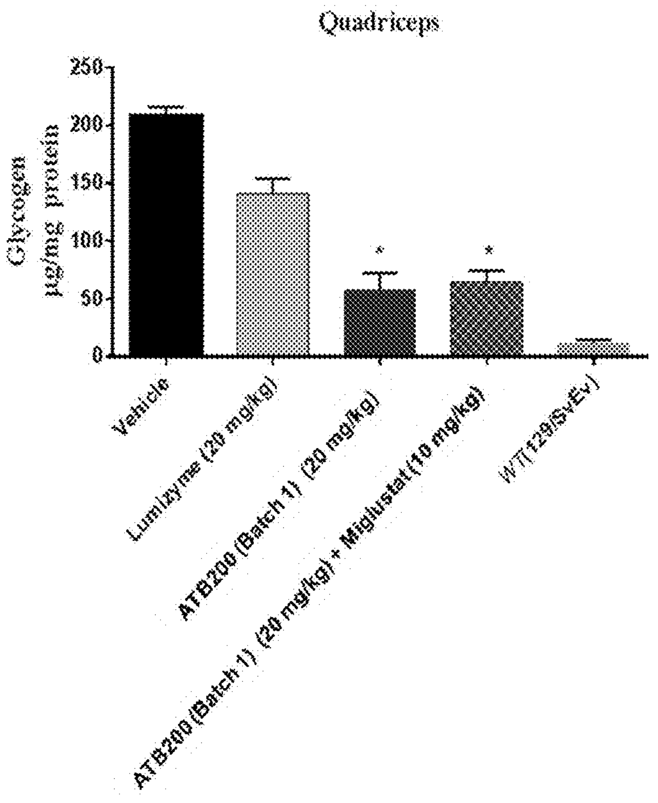
FIGS. 22A-22G are graphs showing glycogen levels in quadriceps, triceps and heart cells from wild-type and Gaa-knockout mice treated with vehicle, alglucosidase alfa and ATB200 in the presence and absence of miglustat.
Figure 22B:
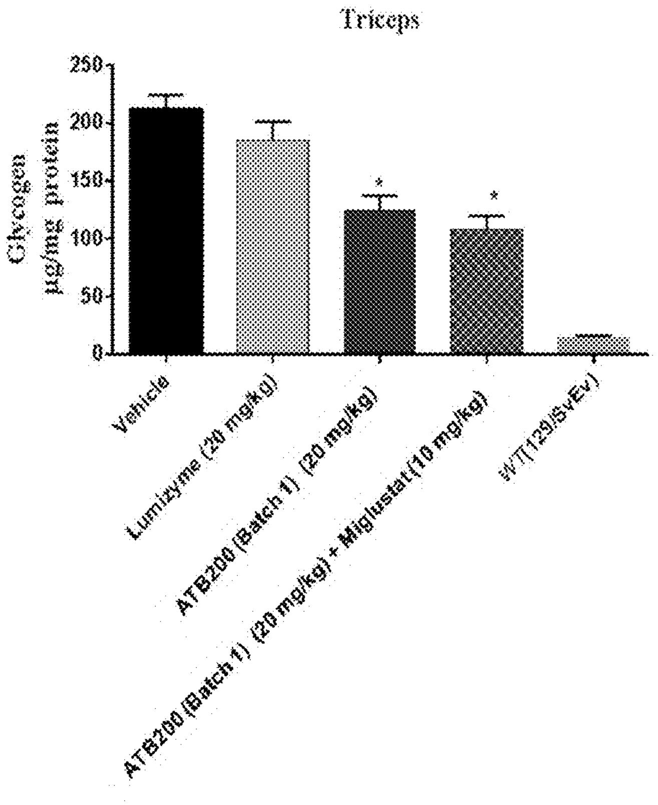
Figure 22C:
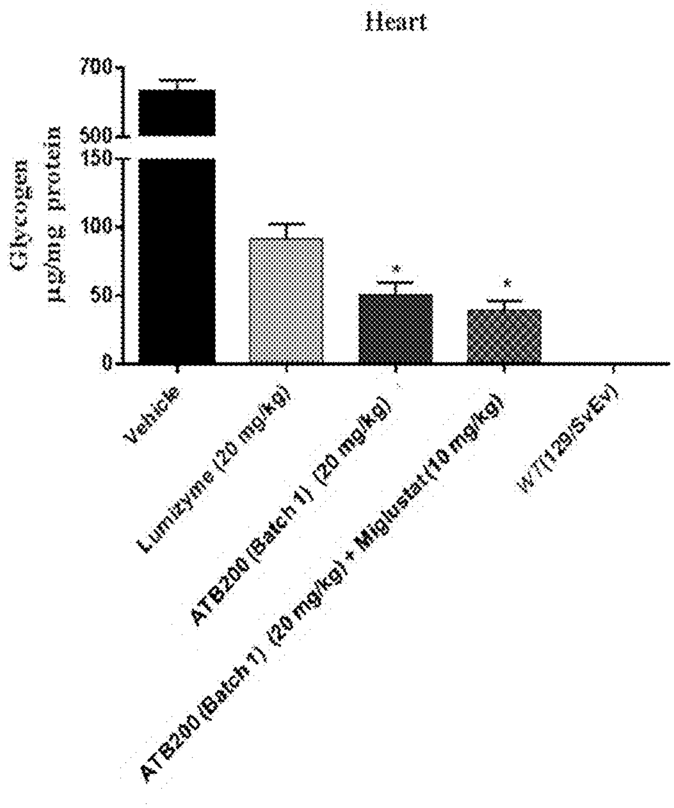
Figure 22D:
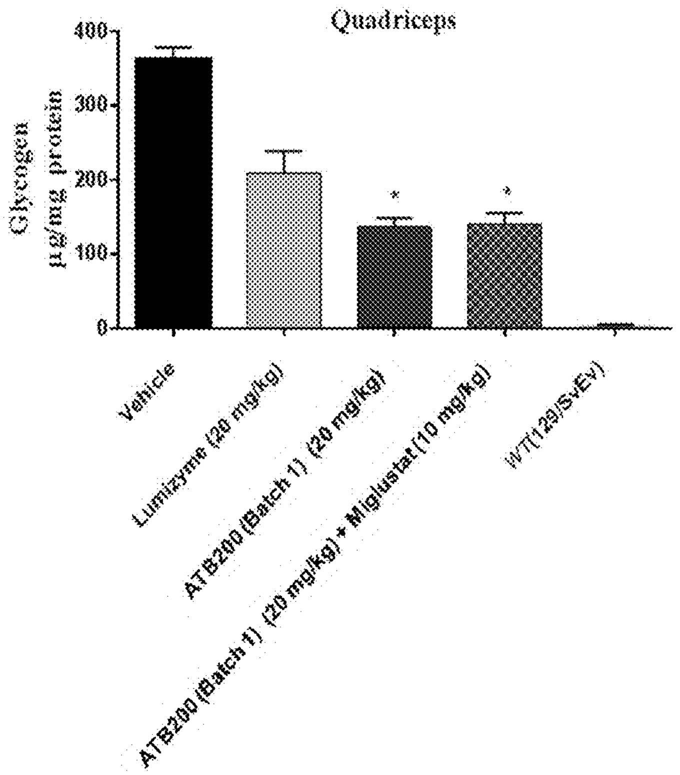
Figure 22E:
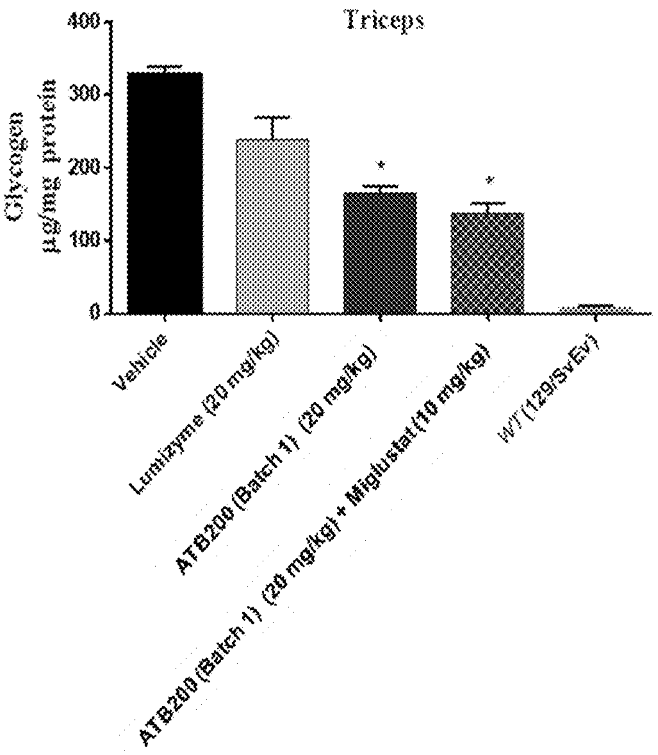
Figure 22F:
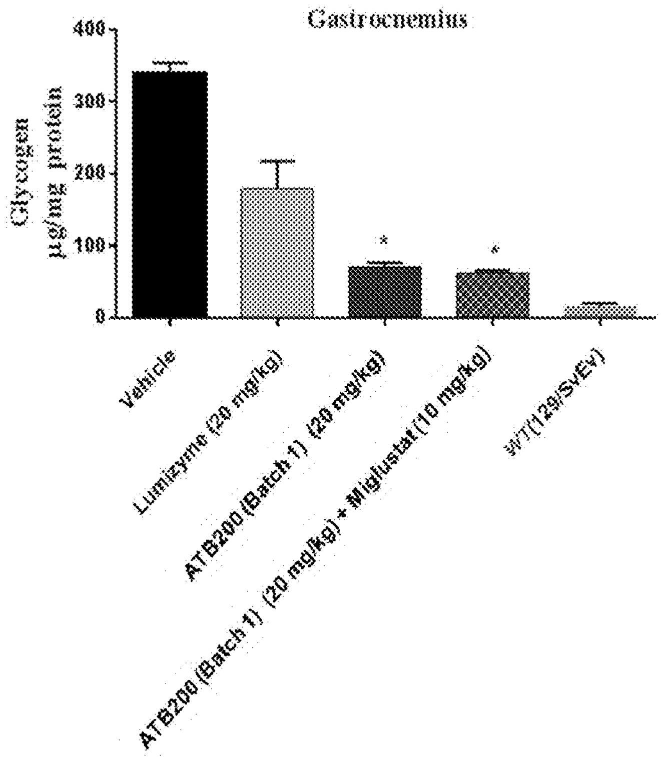
Figure 22G:
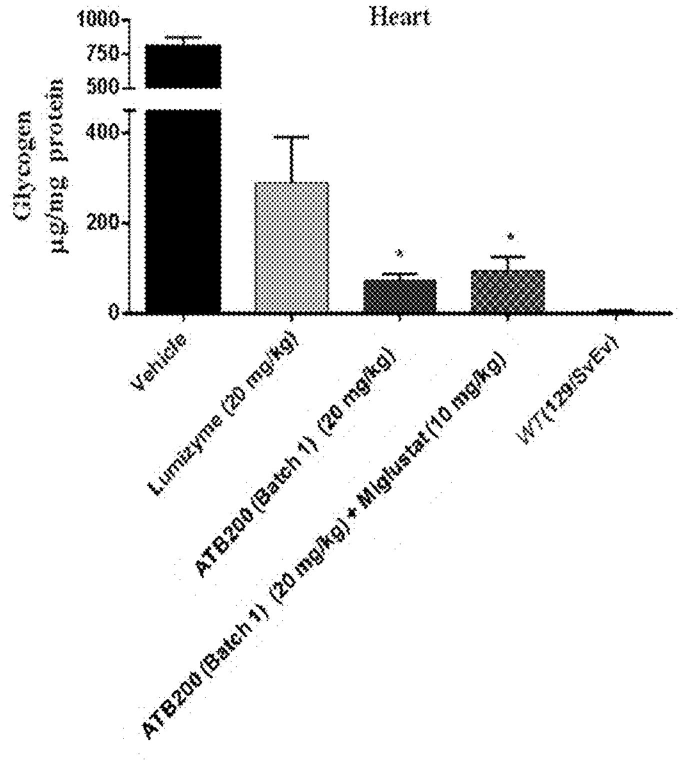

In longer-term studies of 12 biweekly administrations, 20 mg/kg ATB200 plus 10 mg/kg miglustat progressively increased functional muscle strength in Gaa KO mice from baseline as measured by both grip strength and wire hang tests (FIGS. 21A-21B). Alglucosidase alfa (Lumizyme®)-treated mice receiving the same ERT dose (20 mg/kg) were observed to decline under identical conditions throughout most of the study (FIGS. 21A-21B). As with the shorter-term study, ATB200/miglustat had substantially better glycogen clearance after 3 months (FIGS. 22A-22C) and 6 months (FIGS. 22D-22G) of treatment than alglucosidase alfa. ATB200/miglustat also reduced autophagy and intracellular accumulation of LAMP1 and dysferlin after 3 months of treatment (FIG. 23) compared to alglucosidase alfa. In FIG. 21A, * indicates statistically significant compared to Lumizyme® alone ($p<0.05$, 2-sided t-test). In FIGS. 22A-22G, * indicates statistically significant compared to Lumizyme® alone ($p<0.05$, multiple comparison using Dunnett's method under one-way ANOVA analysis).

Taken together, these data indicate that ATB200/miglustat was efficiently targeted to muscles to reverse cellular dysfunction and improve muscle function. Importantly, the apparent improvements in muscle architecture and reduced autophagy and intracellular accumulation of LAMP1 and dysferlin may be good surrogates for improved muscle physiology that correlate with improvements in functional muscle strength. These results suggest that monitoring autophagy and these key muscle proteins may be a rational, practical method to assess the effectiveness therapeutic treatments for Pompe disease in Gaa KO mice that may prove to be useful biomarkers from muscle biopsies in clinical studies.

Figure 23:
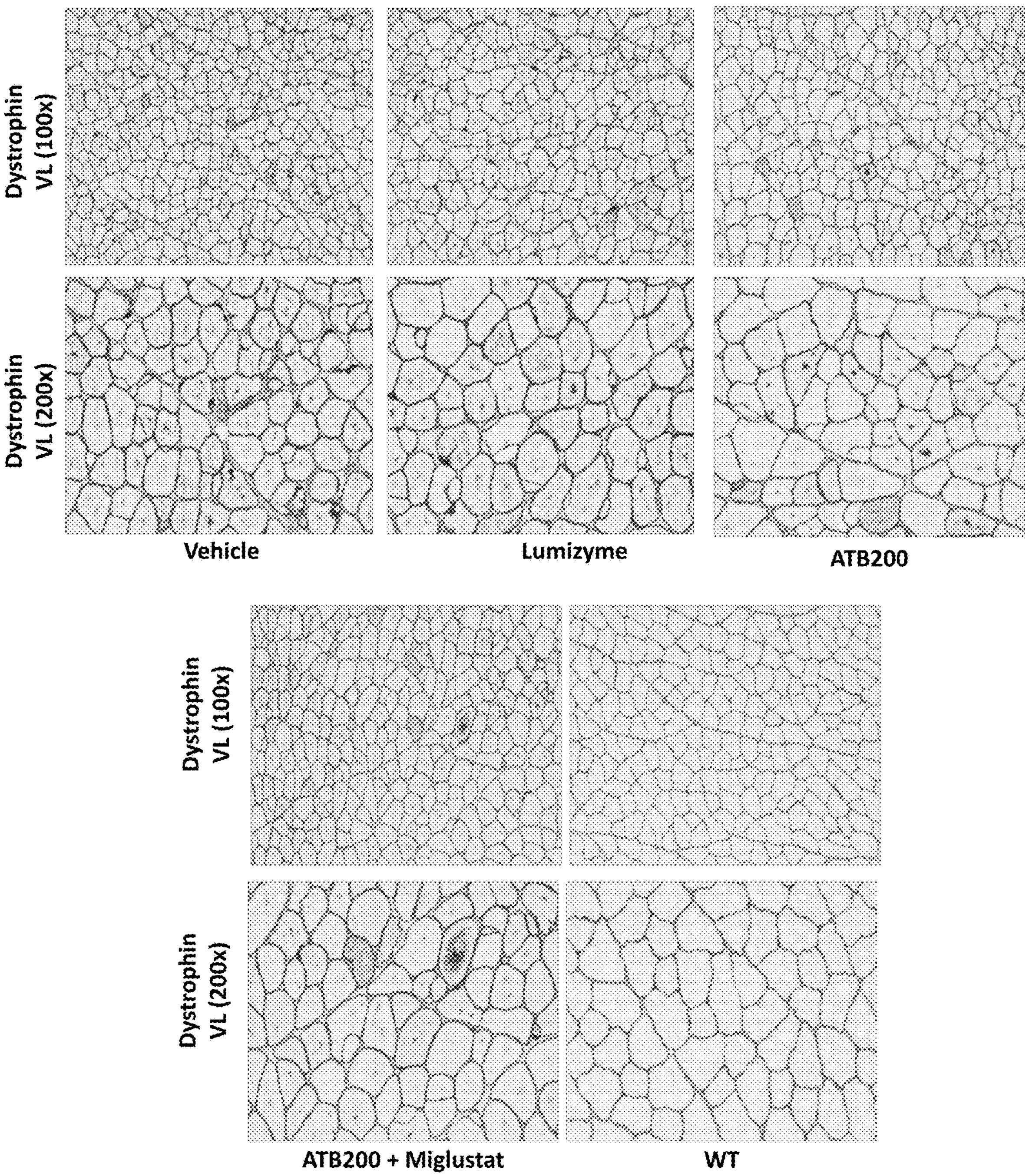
FIG. 23 is a series of photomicrographs (100× and 200×) of muscle fibers of vastus lateralis (VL) from wild-type and Gaa-knockout mice treated with vehicle, alglucosidase alfa and ATB200 in the presence and absence of miglustat, showing dystrophin signals.

FIG. 23 shows that 6 months of ATB200 administration with or without miglustat lowered intracellular accumulation of dystrophin in Gaa KO mice. There was a greater reduction for dystrophin accumulation for ATB200±miglustat than with Lumizyme®.

Example 11: Capturing of rha-Gal A

Figure 20A:
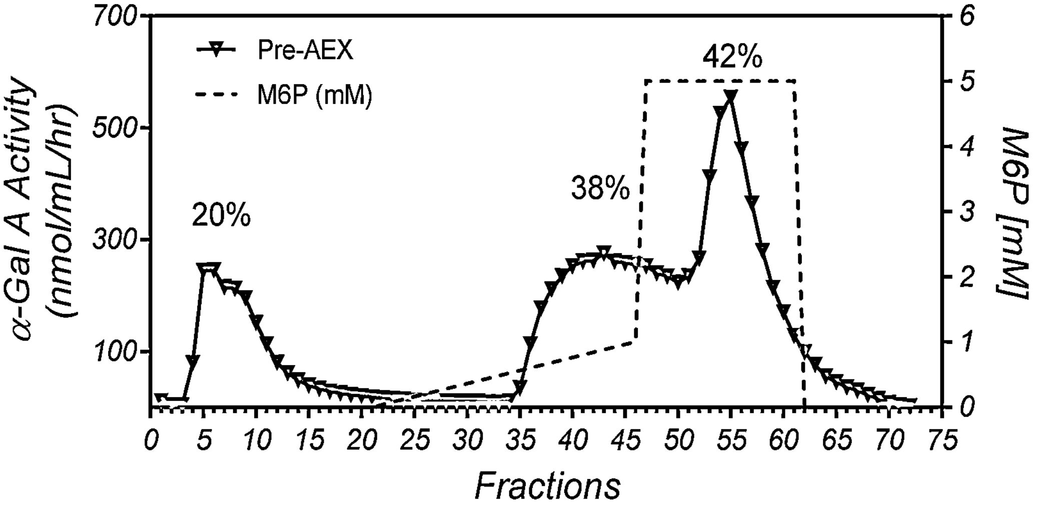
FIGS. 20A and 20B, respectively, are graphs showing the results of CIMPR affinity chromatography of recombinant a-galactosidase A (rha-Gal A) enzyme before and after capture and purification on an anion exchange (AEX) column.
Figure 20B:
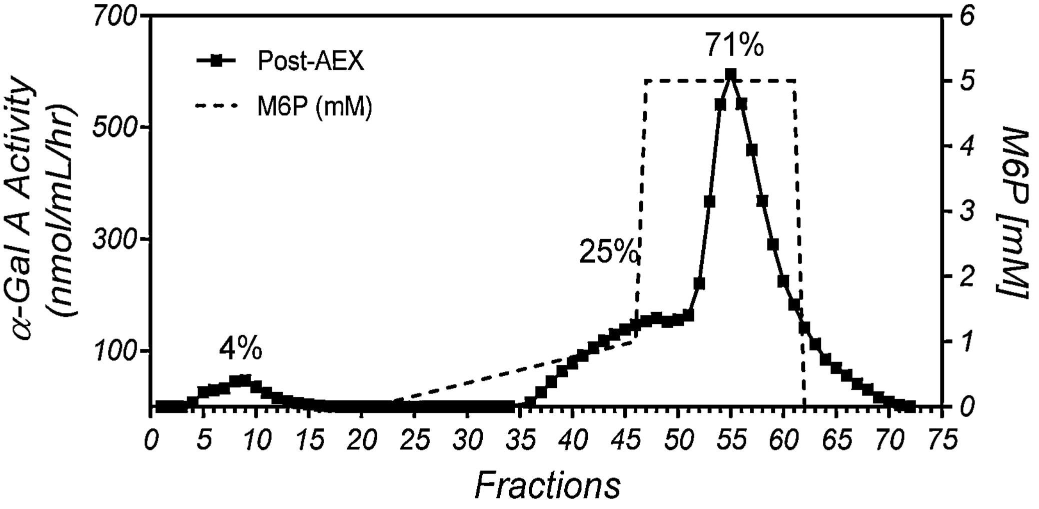

The CIMPR binding profile of recombinant human α-galactosidase A (rha-Gal A) in spent cell culture medium was measured before product capture using AEX chromatography (FIG. 20A) and after product capture using AEX chromatography (FIG. 20B). The dashed line in both graphs refers to the M6P elution gradient. Prior to AEX product capture, 80% of the rha-Gal A is able to bind to the CIMPR. After AEX product capture, the total rhα-Gal A bound increases to 96%.

Example 12: Pharmacokinetic and Safety Data on Recombinant Acid α-Glucosidase ATB200 Co-Administered with Migluststat in ERT-Experienced and ERT-Naïve Patients with Pompe Disease This study was designed to primarily evaluate the safety, tolerability, and pharmacokinetics (PK) of ATB200 co-administered with miglustat. A PK/pharmacodynamic (PD) translational model from Gaa knockout mouse predicted that a combination of ATB200 20 mg/kg with a high dose (e.g. 260 mg) of miglustat in humans would provide optimal glycogen reduction.

In the description below, "high dose" of miglustat refers to a dose of about 260 mg and "low dose" of miglustat refers to a dose of about 130 mg.

The objective was to evaluate the preliminary total GAA protein, ATB200 and miglustat PK data, and safety markers from 10 patients in this of this phase ½ study.

Figure 24:
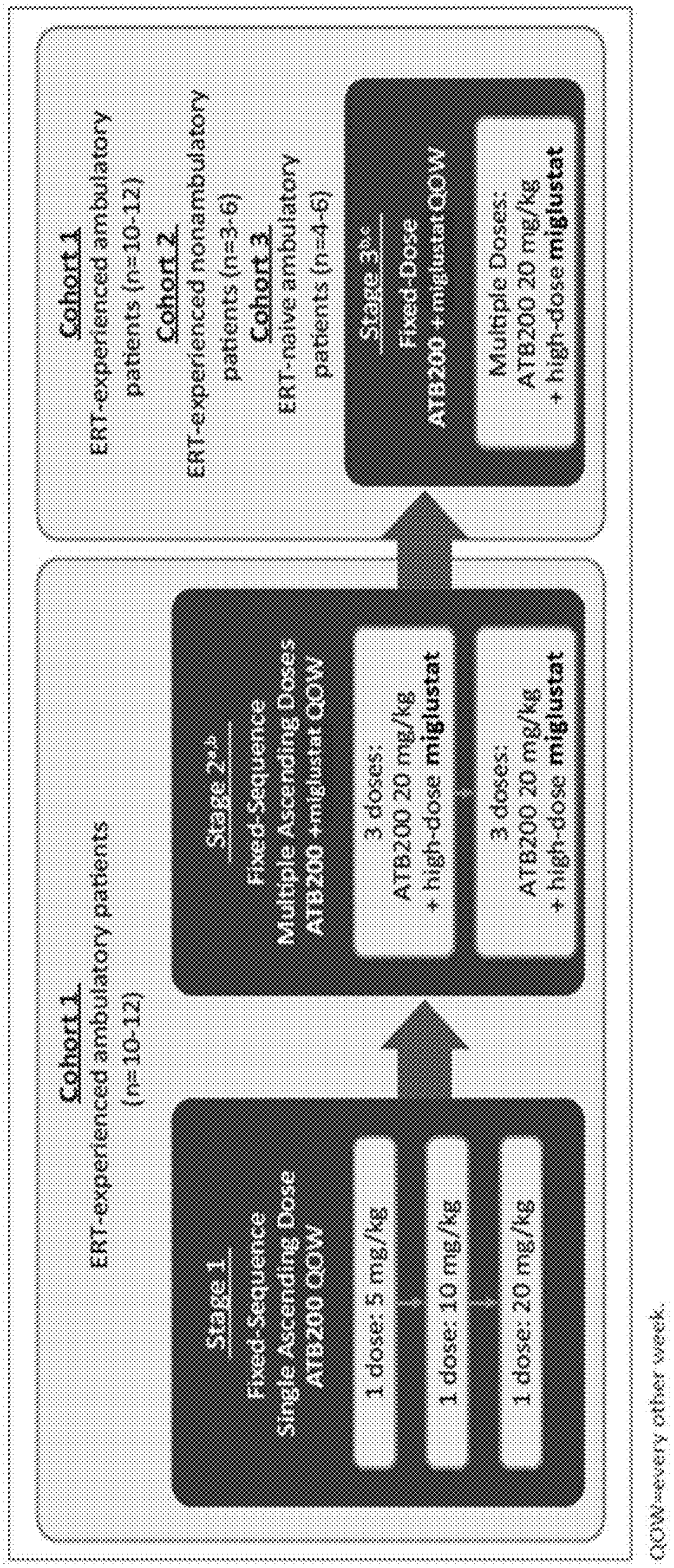
FIG. 24 shows the study design of an open-label, fixed-sequence, ascending-dose, first-in-human, phase ½ study to assess the safety, tolerability, PK, PD, and efficacy of intravenous infusions of ATB200 co-administered with oral miglustat in adults with Pompe disease.

This is an open-label, fixed-sequence, ascending-dose, first-in-human, phase ½ study to assess the safety, tolerability, PK, PD, and efficacy of intravenous infusions of ATB200 co-administered with oral miglustat in adults with Pompe disease (FIG. 24). Mean total GAA protein and miglustat PK results from the first 8 Cohort 1 patients through Visit 9 and the first 2 Cohort 3 patients were assessed.

[a]Safety data from 2 sentinel patients from Cohort 1 were reviewed at each dose level before dosing in Cohorts 2 and 3.

[b]During Stages 2 and 3, miglustat was orally administered prior to the start of ATB200 intravenous infusion. For all doses, ATB200 was intravenously infused for a 4-hour duration.

[c]The first 2 patients in Cohorts 2 and 3 served as sentinel patients for their respective cohorts.

Key inclusion criteria:

- Males and females aged 18-65 years who were diagnosed with Pompe disease based on documented deficiency of GAA enzyme activity or by GAA genotyping
  - Received ERT with alglucosidase alfa for 2-6 years (or ≥2 years for Cohort 2) prior to trial initiation (Cohort 1)
  - Currently receiving alglucosidase alfa at a frequency of every other week and completed the last 2 infusions without a drug-related adverse event resulting in dose interruption (Cohorts 1 and 2)
  - Must be able to walk between 200 and 500 meters on the 6-Minute Walk Test (Cohorts 1 and 3)
  - Upright forced vital capacity must be 30%-80% of predicted normal value (Cohorts 1 and 3)
  - Must be wheelchair-bound and unable to walk unassisted (Cohort 2)

PK Analysis:

- Blood samples for plasma total GAA protein and activity concentration were collected
- Stage 1: prior to start of ATB200 infusion and 1, 2, 3, 3.5, 4, 4.5, 5, 6, 8, 10, 12, and 24 hour(s) post-start of infusion
- Stages 2 and 3: 1, 2, 3, 4, 4.5, 5, 6, 7, 9, 11, 13, and 25 hour(s) post-miglstat oral administration
- Blood samples for plasma miglustat concentrations were taken just prior to miglustat oral administration (time 0) and 1, 1.5, 2, 2.5, 3, 4, 5, 6, 9, 11, and 25 hour(s) after miglustat oral administration. Plasma miglustat is determined by a validated LC-MS/MS assay
- Total GAA protein concentrations in plasma for ATB200 5, 10, and 20 mg/kg were determined by a validated LC-MS/MS quantification of rhGAA-specific "signature" peptide(s)

A preliminary analysis was completed in 8 patients in Cohort 1 who completed Stages 1 and 2 and 2 patients in Cohort 3 who started Stage 3

Initial ERT-switch patients are representative of the Pompe disease population, with mean 5.02 years on ERT (Table 6)

TABLE 6

Baseline Characteristics

| Baseline Characteristics (N = 12[a]) | ERT-Experienced Ambulatory (n = 10) | Naïve (n = 2) |
|---|---|---|
| Time on ERT (Lumizyme ®/Myozyme ®), years, mean (STDV) | 5.02 (1.2) | N/A |
| Age, years, mean (range) | 47.7 (8.19) | 33.0 (12.73) |
| Sex, M/F, % | 80/20 | 0/100 |
| 6MWT, meters, mean (STDV) | 398.4 (95.92) | 432.1 (67.81) |
| Upright FVC, mean %, predicted (STDV) | 51.9 (13.84) | 51.0 (26.87) |

6MWT = 6-minute walk test; FVC = forced vital capacity; N/A = not available; STDV = standard deviation.
[a]n = 10 from Cohort 1 (ambulatory ERT-switch) through interim data analysis; n = 2 from Cohort 3 (naive).

Total GAA Protein

Figure 25A:
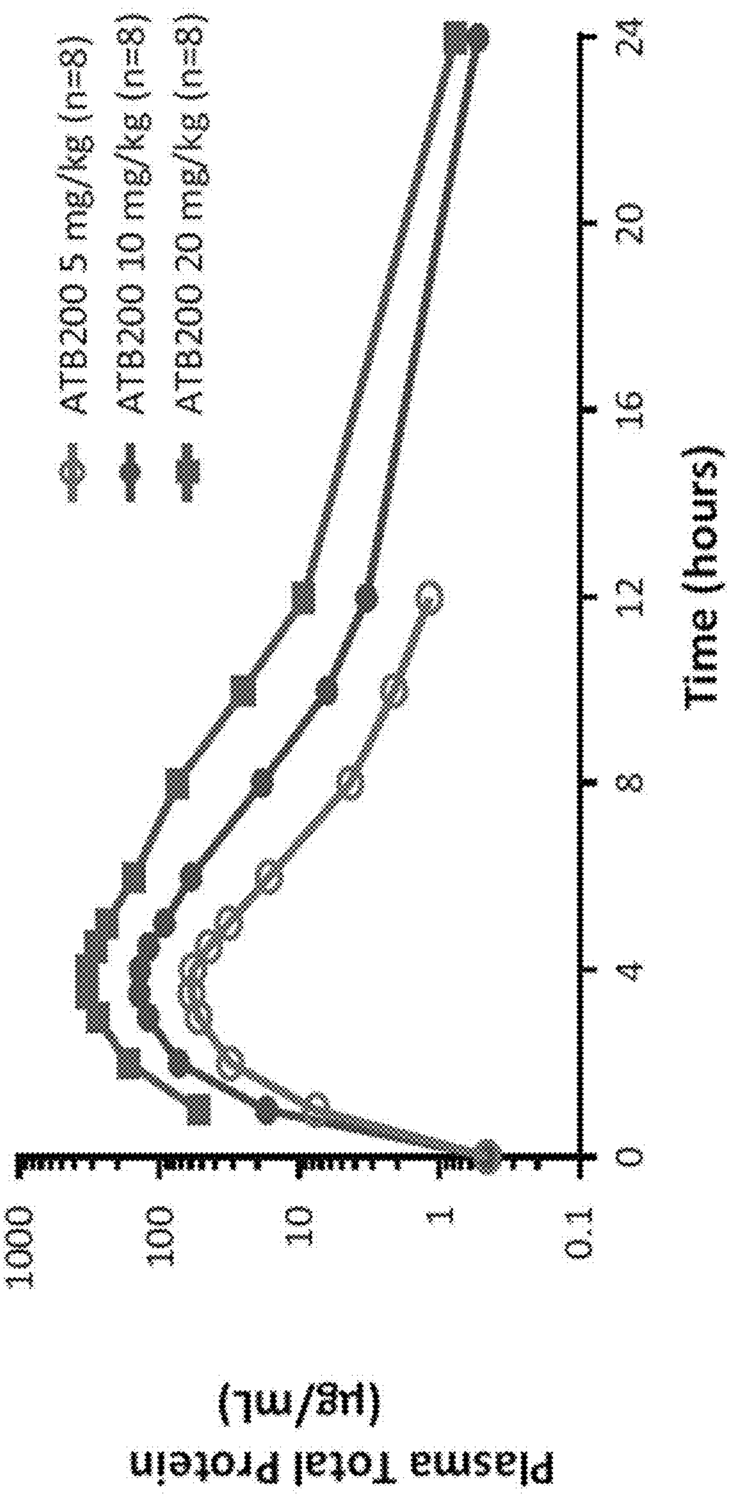
FIGS. 25A-25B are graphs showing the concentration-time profiles of GAA total protein in plasma in human subjects after dosing of 5, 10 or 20 mg/kg ATB200, 20 mg/kg ATB200 and 130 mg miglustat, or 20 mg/kg ATB200 and 260 mg miglustat.
Figure 25B:
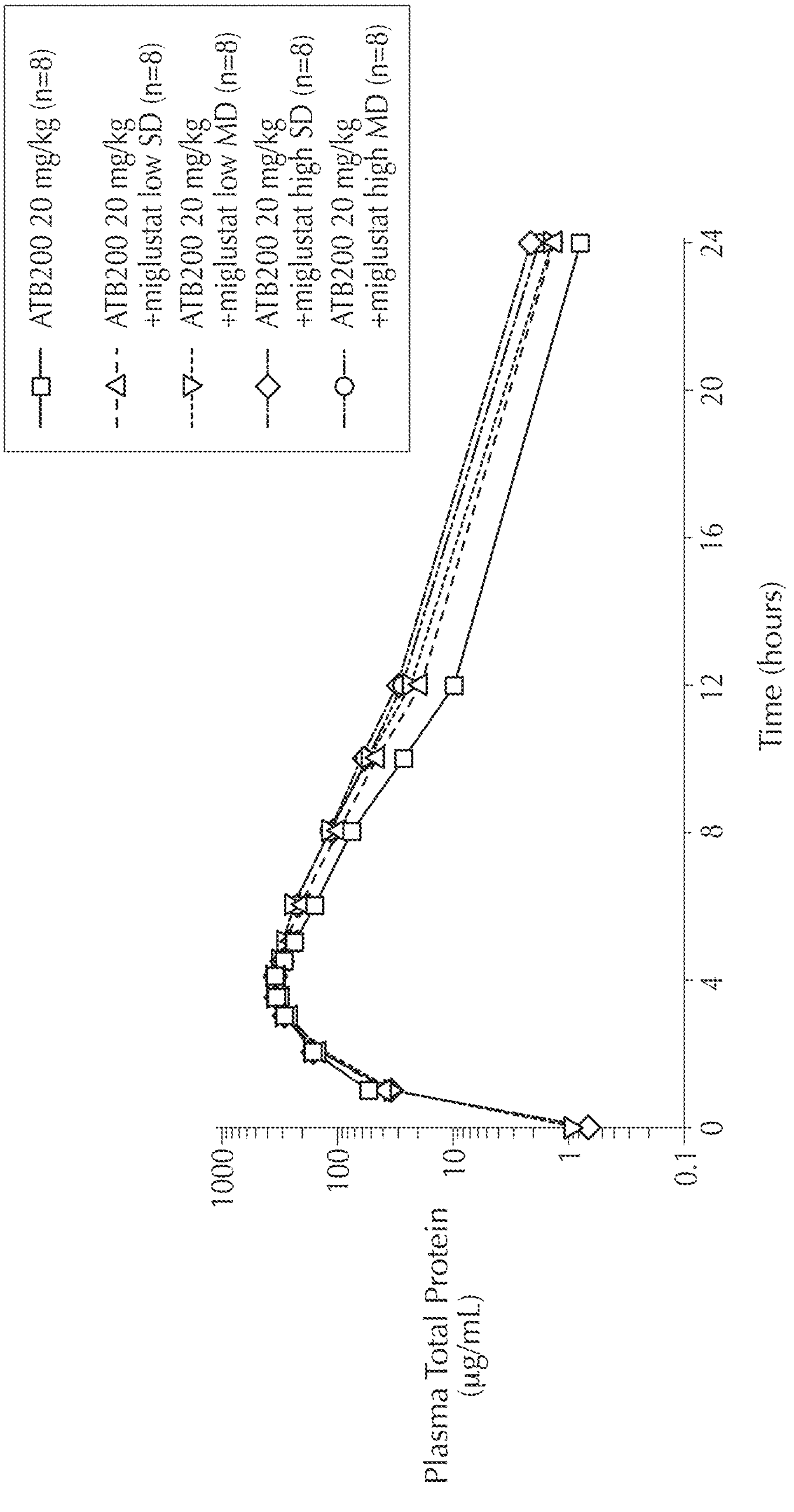
Figure 25C:
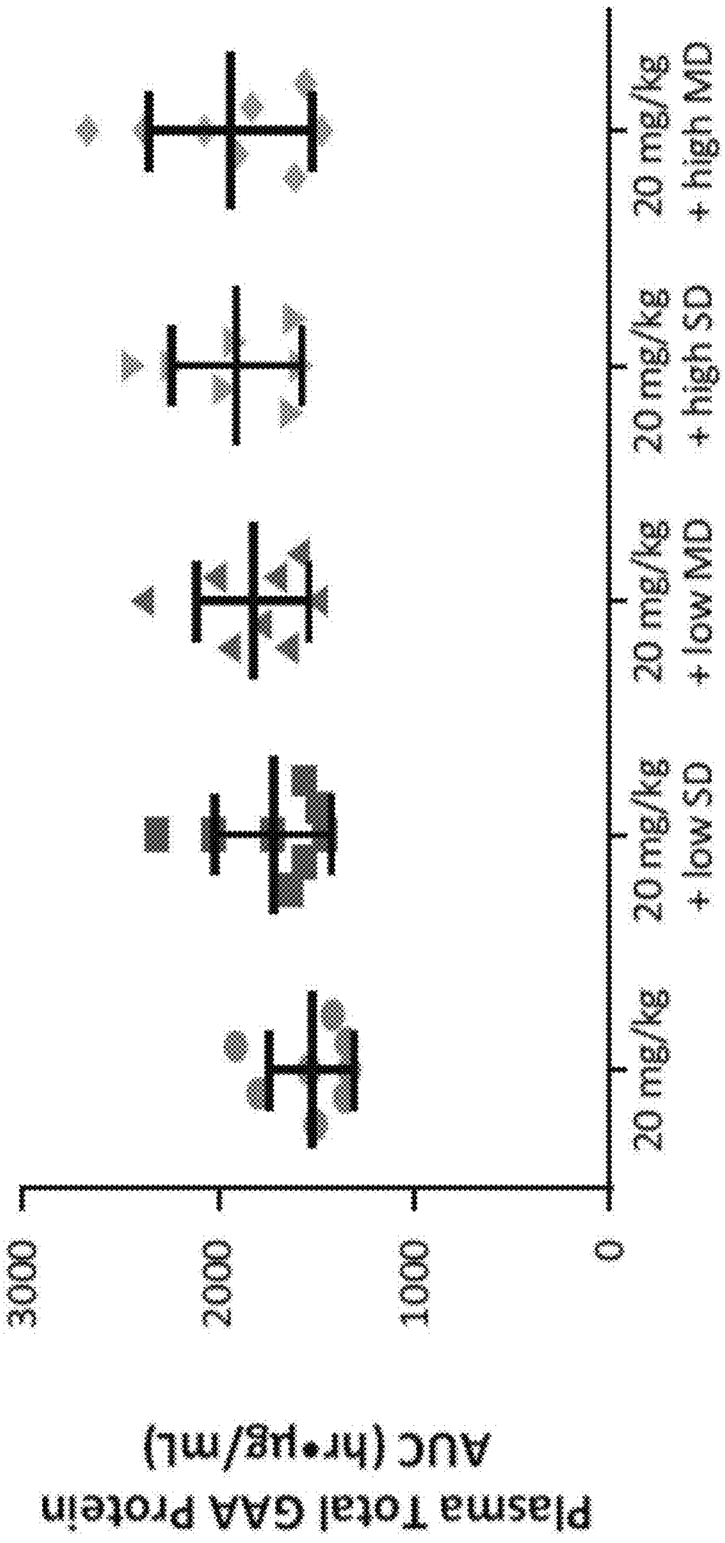
FIG. 25C is a graph showing the AUC of GAA total protein in plasma in human subjects after dosing of 20 mg/kg ATB200, 20 mg/kg ATB200 and 130 mg miglustat, or 20 mg/kg ATB200 and 260 mg miglustat.
Figure 25D:
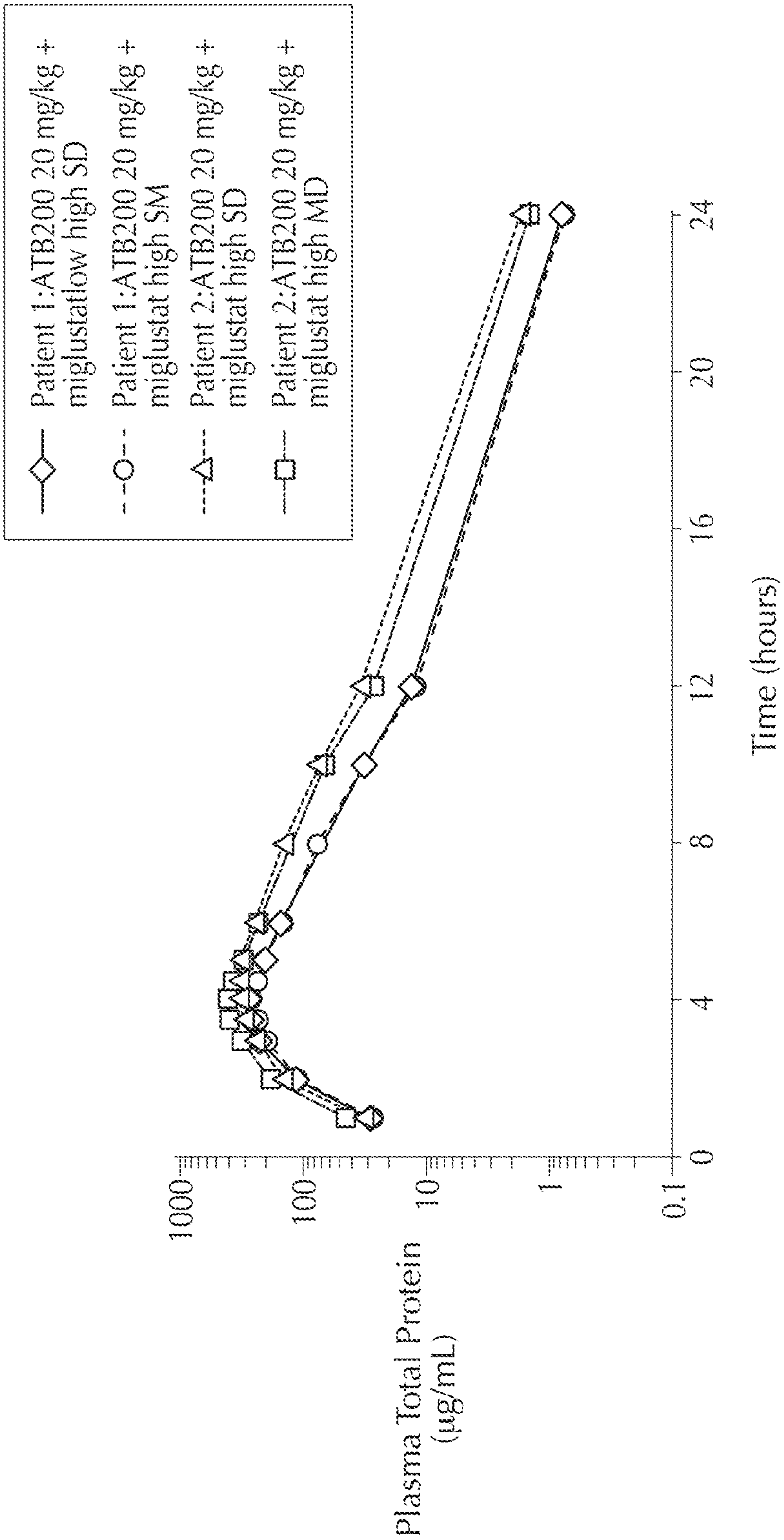
FIG. 25D is a graph showing the concentration-time profiles of GAA total protein in plasma in two individual human subjects after dosing of 20 mg/kg ATB200 and 260 mg miglustat.

When given alone, ATB200 increases in a slightly greater-than-dose-proportional manner (Table 7 and FIGS. 25A-25D). Variability appears to increase with miglustat dose (FIG. 25C). Co-administration of ATB200 20 mg/kg with the high dose of miglustat (260 mg) increased total GAA protein exposure (AUC) by approximately 25% relative to ATB200 alone at 20 mg/kg. The distribution half-life (a-phase) increased by 45%, suggesting that the high dose of miglustat stabilizes ATB200 in plasma. An increase in the distribution half-life is accompanied by an increase in AUC from time to maximum plasma concentration to approximately 12 hours post-dose. The increases in AUC and half-life can be observed on the log scale, during the terminal elimination phase (FIG. 25B). ATB200 demonstrated a relatively high volume of distribution. The disposition of plasma total GAA protein appears similar between ERT-naive (Cohort 3) and ERT-experienced patients (Cohort 1) (FIGS. 25A and 25D).

TABLE 7

Total GAA Protein

| Cohort | Treatment | $C_{max}$ (ng/ml)[a] | $t_{max}$ (hr)[b] | $AUC_{0-t}$ (ng * hr/mL)[a] | $AUC_{0-\infty}$ (ng * hr/mL)[a] | $\beta t_{1/2}$ (hr)[c] | $\alpha t_{1/2}$ (hr)[c] | $CL_T$ (L/hr)[c] | $V_{ss}$ (L)[c] |
|---|---|---|---|---|---|---|---|---|---|
| 1 | 5 mg/kg alone[d] | 61 (18.1) | 3.8 (3.0-4.0) | 215 (16.7) | 218 (16.4) | 1.9 (16.7) | 1.1 (10.2) | 2.1 (16.9) | 4.62 (12.7) |
| 1 | 10 mg/kg alone[d] | 144 (16.6) | 4.0 (3.5-4.0) | 578 (20.3) | 584 (20.4) | 1.6 (46.1) | 1.3 (10.5) | 1.59 (25.4) | 3.87 (16.5) |
| 1 | 20 mg/kg alone[d] | 345 (10.1) | 4.0 (3.5-4.0) | 1508 (14.5) | 1512 (14.4) | 2.1 (29.7) | 1.5 (6.5) | 1.22 (21.7) | 3.52 (12.4) |
| 1 | ATB200 20 mg/kg + miglustat low SD[d] | 334 (16.2) | 4.0 (3.5-4.0) | 1694 (17.7) | 1701 (17.5) | 2.4 (16.6) | 1.8 (10.2) | 1.09 (22.9) | 3.76 (13.3) |
| 1 | ATB200 20 mg/kg + miglustat low MD[d] | 353 (13.7) | 4.0 (3.5-5.0) | 1804 (15.7) | 1808 (15.8) | 2.5 (8.1) | 1.9 (21.8) | 1.02 (21.4) | 3.73 (12.3) |
| 1 | ATB200 20 mg/kg + miglustat high SD[e] | 349 (13.9) | 4.0 (3.5-4.0) | 1878 (17.5) | 1886 (17.5) | 2.7 (13.1) | 2.3 (18.9) | 0.98 (26.5) | 3.74 (12.3) |
| 1 | ATB200 20 mg/kg + miglustat high MD[d] | 356 (20.2) | 4.0 (3.5-4.0) | 1886 (21.3) | 1901 (21.7) | 2.5 (20.5) | 2.1 (16.1) | 0.98 (27.3) | 3.6 (18.7) |

TABLE 7-continued

Total GAA Protein

| Cohort | Treatment | $C_{max}$ (ng/ml)[a] | $t_{max}$ (hr)[b] | $AUC_{0-t}$ (ng * hr/mL)[a] | $AUC_{0-\infty}$ (ng * hr/mL)[a] | $\beta t_{1/2}$ (hr)[c] | $\alpha t_{1/2}$ (hr)[c] | $CL_T$ (L/hr)[c] | $V_{ss}$ (L)[c] |
|---|---|---|---|---|---|---|---|---|---|
| 3 | ATB200 20 mg/kg + miglustat high MD[f] | 291 (21.6) | 4.3 (4.0-4.5) | 1597 (34.8) | 1600 (34.9) | 2.4 (5.4) | 2 (14.5) | 0.69 (28.9) | 2.61 (17.3) |
| 3 | ATB200 20 mg/kg + miglustat high MD[f] | 330 (27.5) | 4.0 (4.0-4.0) | 1672 (32.7) | 1676 (32.6) | 2.6 (8.7) | 1.9 (9.0) | 0.66 (26.6) | 2.33 (23.2) |

AUC = area under the curve;
$CL_T$ = total body clearance;
$C_{max}$ = maximum drug concentration;
CV = coefficient of variability;
MD = multiple doses;
SD = single dose;
$t_{1/2}$ = half-life;
$t_{max}$ = time to maximum drug concentration;
$V_{ss}$ = apparent volume of distribution in steady state.
[a]Geometric mean (CV %).
[b]Median (min-max).
[c]Arithmetic mean (CV %.)
[d]n = 8.
[e]n = 7.
[f]n = 2.

Miglustat PK

Figure 26:
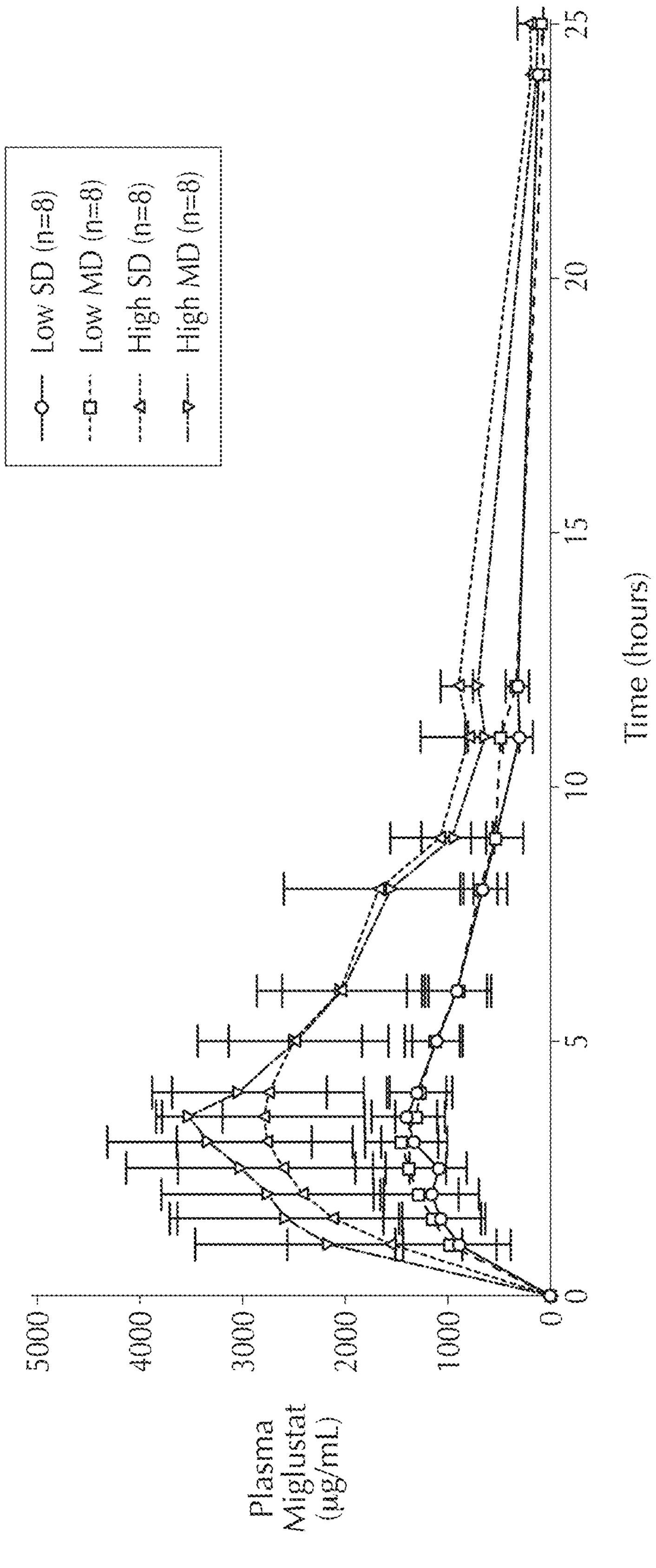
FIG. 26 is a graph showing the concentration-time profiles of miglustat in plasma in human subjects after dosing of 130 mg or 260 mg of miglustat.

Miglustat demonstrated dose-proportional kinetics (Table 8 and FIG. 26). Plasma miglustat appears similar between single and multiple doses.

TABLE 8

Miglustat PK Summary

| Treatment | $C_{max}$ (ng/mL)[a] | $t_{max}$ (h)[b] | $AUC_{0-t}$ (ng * h/mL)[a] | $AUC_{0-\infty}$ (ng * h/mL)[a] | $t1_{/2}$ (h)[c] | CL/F (L/h)[c] | $V_z$/F (L)[c] |
|---|---|---|---|---|---|---|---|
| Low SD | 1486 (29.9) | 3.5 (1.5-3.5) | 11,807 (25.6) | 12,565 (26.8) | 5.6 (11.7) | 10.6 (23) | 85.8 (23.4) |
| Low MD | 1518 (27.6) | 3.0 (1.5-3.5) | 12,254 (26.4) | 13,094 (28.3) | 5.9 (32.1) | 10.2 (23.9) | 86.7 (43.9) |
| High SD | 3059 (36.1) | 3.5 (1.5-5) | 23,999 (35) | 25,859 (34.4) | 5.7 (29.9) | 10.6 (33) | 86.3 (45.7) |
| High MD | 3569 (25.5) | 3.0 (1.0-4.0) | 24,970 (24.1) | 25,972 (23) | 5.3 (15.6) | 10.3 (26.4) | 81 (41.8) |

$V_z$ = apparent volume of distribution in terminal state.
[a]Geometric mean (CV %).
[b]Median (min-max).
[c]Arithmetic mean (CV %).

Pharmacodynamics

Figure 27A:
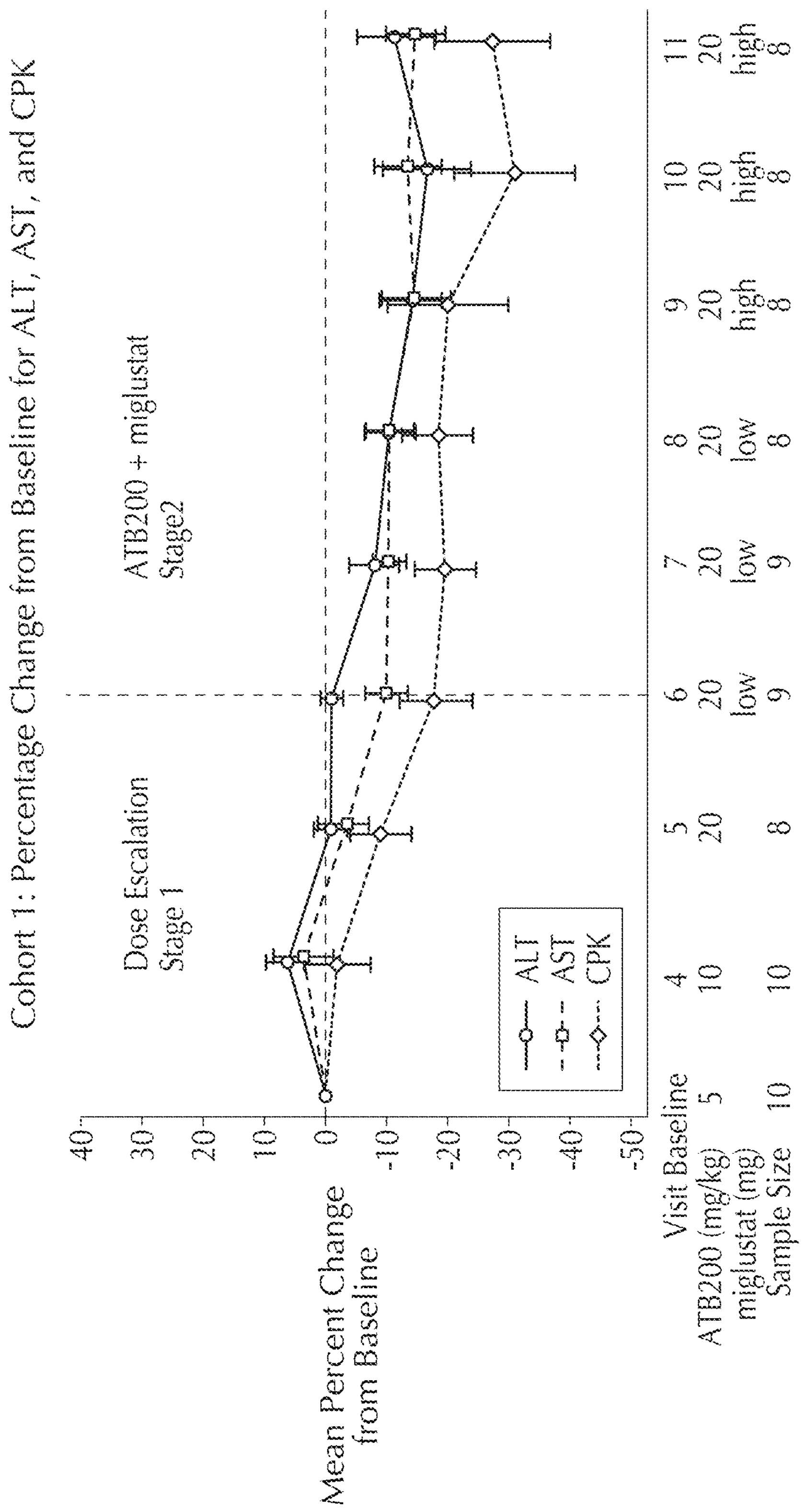
FIGS. 27A-27D are graphs showing changes in alanine aminotransferase (ALT), aspartate aminotransferase (AST), creatine phosphokinase (CPK) and hexose tetrasaccharide (Hex4) levels in human patients after administration of ascending doses of ATB200 (5, 10 and 20 mg/kg) followed by co-administration of ATB200 (20 mg/kg) and miglustat (130 and 260 mg).
Figure 27B:
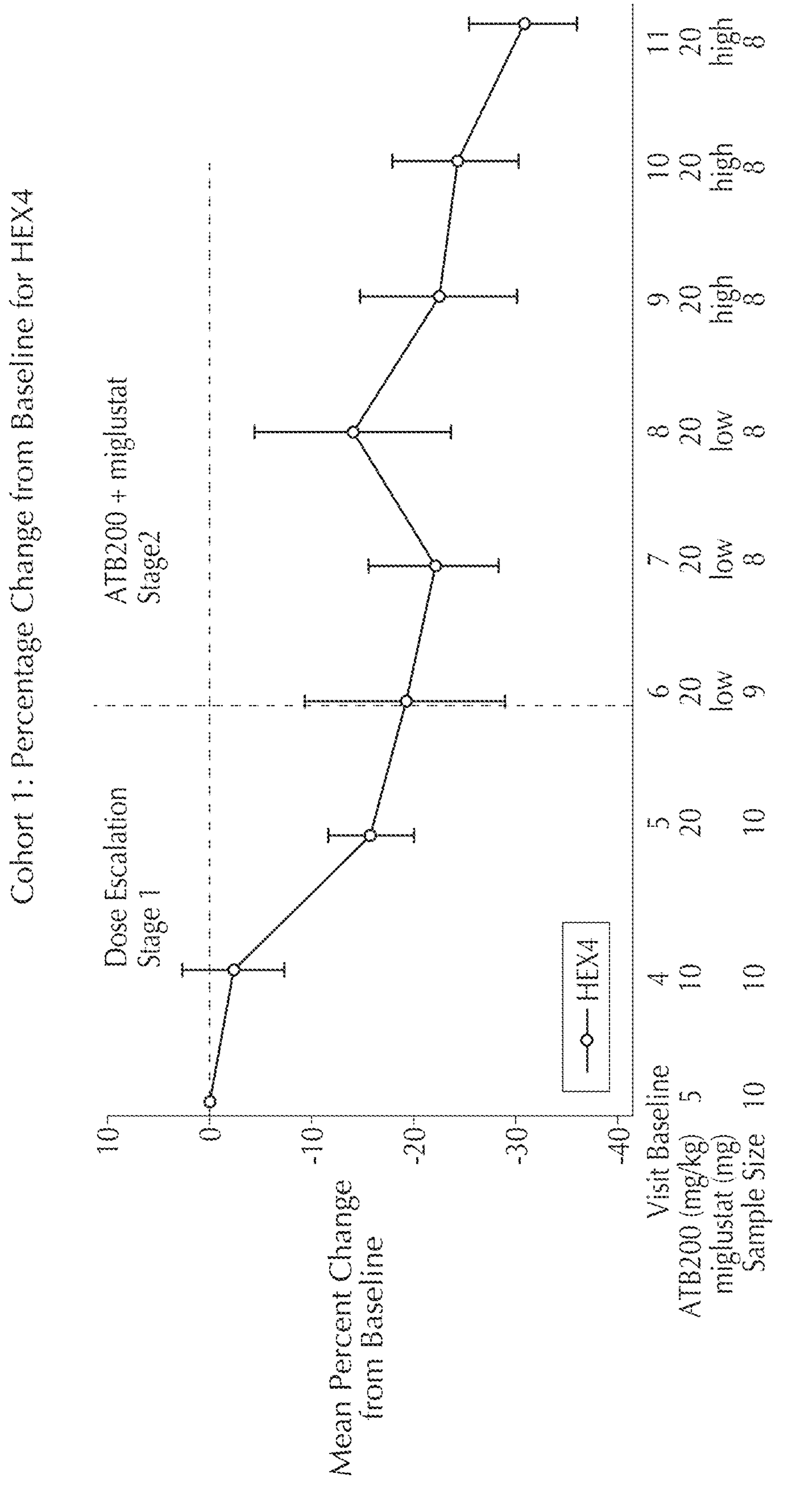
Figure 27C:
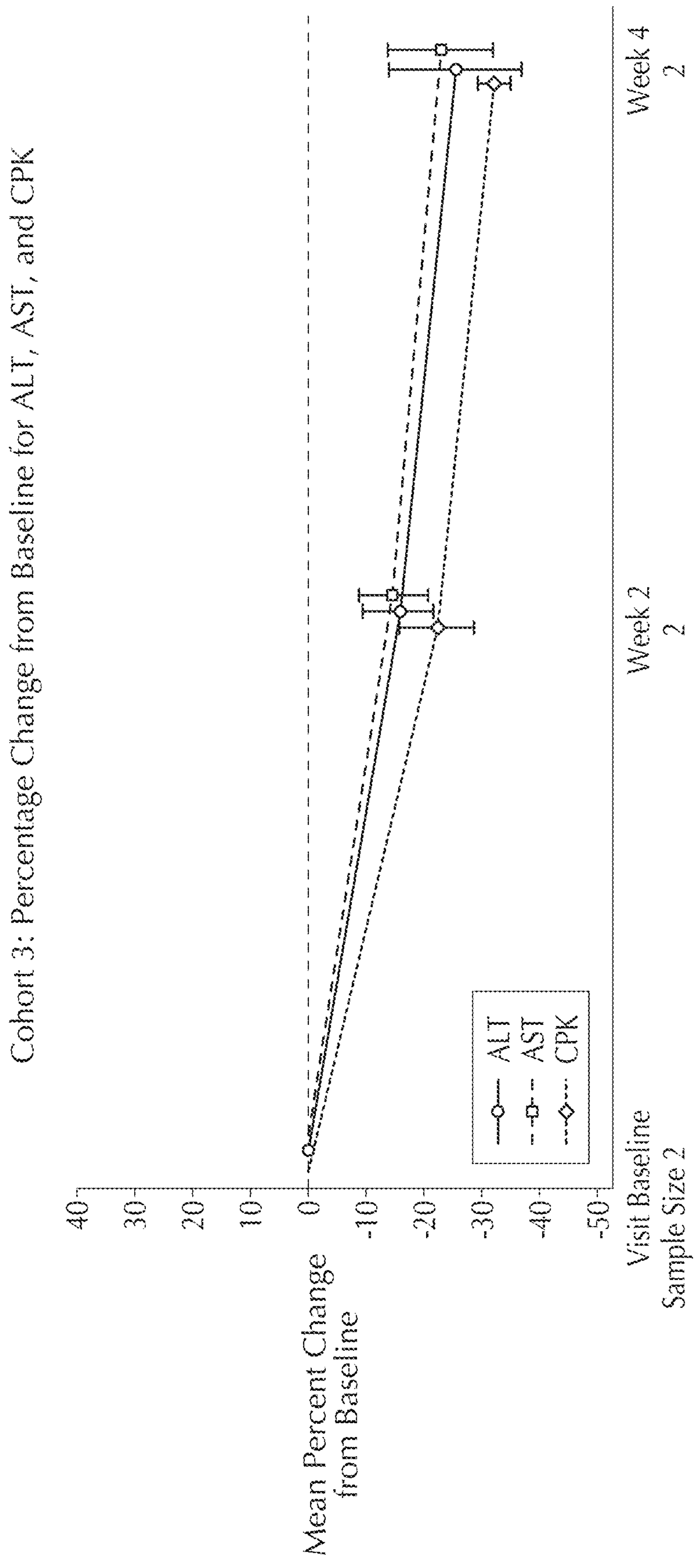
Figure 27D:
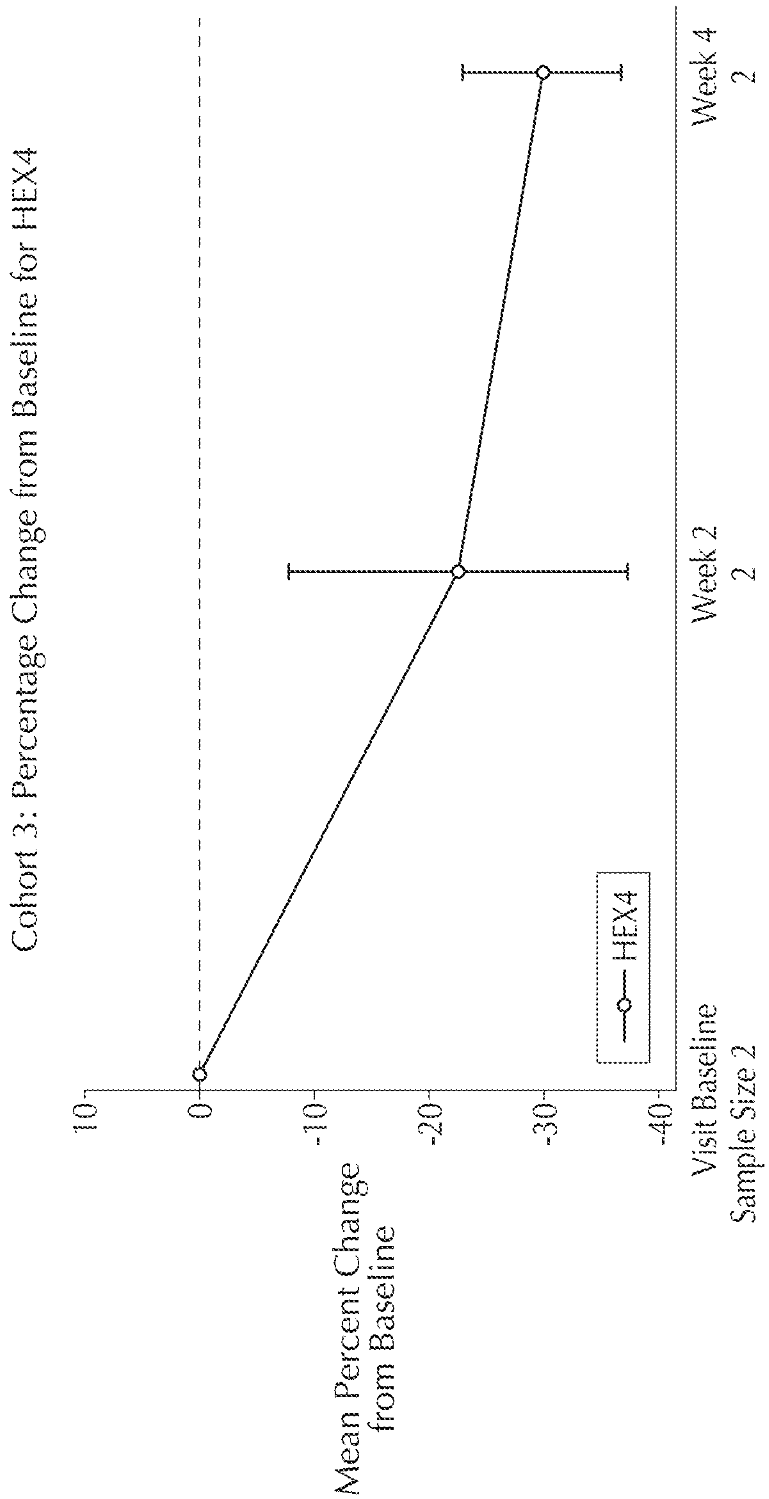

By the 11th visit in ERT-experienced patients from Cohort 1 (FIGS. 27A and 27B):

- Alanine aminotransferase (ALT) decreased in 5 of 8 patients; 4/4 patients with elevated baseline levels normalized
- Aspartate aminotransferase (AST) decreased in 6 of 8 patients; 3/4 patients with elevated baseline levels normalized
- Creatine phosphokinase (CPK) decreased in 6 of 8 patients; 2/6 patients with elevated baseline levels normalized
- Urine glucose tetrasaccharide (HEX4) levels decreased in 8 of 8 patients By week 4, all 4 biomarker levels decreased in the 2 patients in the treatment-naive cohort (Cohort 3) (FIGS. 27C and 27D).

In FIGS. 27A-27D, data are represented as mean±standard error.

Safety

- No serious adverse events (AEs) or infusion-associated reactions were reported after 155+ total infusions in all patients
- Treatment-emergent AEs, reported in 11/13 (84%) patients, were generally mild and transient.
- Treatment-related AEs reported in 7/13 (53%) patients: nausea (n=1), fatigue (n=1), headache (n=1), tremor (n=2), acne (n=1), tachycardia (n=1), and hypotension (n=1).

CONCLUSIONS

- ATB200 alone and in combination with miglustat has been safe and well tolerated, with no infusion-associated reactions to date.

- ATB200 alone showed greater-than-dose-proportional increases in exposure, which was further enhanced with miglustat, suggesting a stabilizing effect of chaperone on ATB200.
- After switching from standard of care to ATB200/miglustat, patients generally showed an improvement in biomarkers of muscle damage, with many patients demonstrating normalization by week 18.
- The initial 2 treatment-naive patients treated with ATB200/miglustat demonstrated robust reduction in all biomarkers of muscle damage The embodiments described herein are intended to be illustrative of the present compositions and methods and are not intended to limit the scope of the present invention. Various modifications and changes consistent with the description as a whole and which are readily apparent to the person of skill in the art are intended to be included. The appended claims should not be limited by the specific embodiments set forth in the examples, but should be given the broadest interpretation consistent with the description as a whole.

Patents, patent applications, publications, product descriptions, GenBank Accession Numbers, and protocols are cited throughout this application, the disclosures of which are incorporated herein by reference in their entireties for all purposes.

What is claimed is:

1. A method for producing purified recombinant human acid alpha-glucosidase (rhGAA), wherein the purified rhGAA comprises an amino acid sequence that is at least 98% identical to SEQ ID NO: 2, the method comprising:

i) in a bioreactor, culturing host cells that secrete the rhGAA;

ii) removing medium from the bioreactor;

iii) filtering the medium to provide a filtrate;

iv) loading the filtrate onto a first chromatography column to capture the rhGAA, wherein the first chromatography column is an anion exchange chromatography (AEX) column, wherein the filtrate is not loaded onto a chromatography column prior to the AEX column; and v) eluting the rhGAA from the AEX column, wherein the purified rhGAA comprises at least 3.0% of the total N-glycans of the rhGAA are in the form of a bis-mannose-6-phosphate (bis-M6P) N-glycan and wherein at least 90% of the purified rhGAA binds to cation-independent mannose-6-phosphate receptor (CI-MPR).

2. The method of claim 1, wherein at least 90% of the purified rhGAA comprises an N-glycan carrying mono-M6P or bis-M6P.

3. The method of claim 1, wherein the purified rhGAA comprises seven potential N-glycosylation sites.

4. The method of claim 2, wherein the rhGAA has seven potential N-glycosylation sites that are located at amino acids corresponding to N84, N177, N334, N414, N596, N826, and N869 of SEQ ID NO:2, respectively.

5. The method of claim 3, wherein at least 50% of the purified rhGAA comprise an N-glycan unit bearing bis-M6P at the first potential N-glycosylation site, at least 30% of the purified rhGAA comprise an N-glycan unit bearing mono-M6P at the second potential N-glycosylation site, at least 30% of the purified rhGAA comprise an N-glycan unit bearing bis-M6P at the fourth potential N-glycosylation site, or at least 20% of the purified rhGAA comprise an N-glycan unit bearing mono-M6P at the fourth potential N-glycosylation site.

6. The method of claim 1, further comprising:

applying the rhGAA eluted from the AEX column onto a second chromatography column; and eluting the rhGAA from the second chromatography column.

7. The method of claim 6, wherein the second chromatography column is an immobilized metal affinity chromatography (IMAC) column, a cation exchange chromatography (CEX) column, or a size exclusion chromatography (SEC) column.

8. The method of claim 1, further comprising inactivating viruses in the rhGAA eluted from the AEX column.

9. The method of claim 6, further comprising inactivating viruses in the rhGAA eluted from the second chromatography column.

10. The method of claim 1, further comprising filtering the purified rhGAA to provide a filtered product.

11. The method of claim 10, further comprising filling a vial with the filtered product.

12. The method of claim 1, further comprising lyophilizing the purified rhGAA.

13. The method of claim 1, wherein the host cells comprise Chinese hamster ovary (CHO) cells.

14. The method of claim 1, wherein the purified rhGAA comprises 3.0-6.0 moles of M6P per mole of rhGAA.

15. The method of claim 1, wherein the purified rhGAA comprises 3.0-8.0 moles of sialic acid residues per mole of rhGAA.

16. The method of claim 1, wherein the purified rhGAA comprises 3.0-6.0 moles of M6P and 3.0-8.0 moles of sialic acid residues per mole of rhGAA.

17. The method of claim 1, wherein the purified rhGAA comprises on average at least 1 mol bis-M6P per mol of protein.

18. The method of claim 1, wherein the purified rhGAA comprises on average 1.3 mol bis-M6P per mol of protein.

19. The method of claim 1, wherein the purified rhGAA comprises at least 17% of the total N-glycans of the rhGAA are in the form of a bis-M6P N-glycan.

20. The method of claim 1, wherein the purified rhGAA comprises 4.0 moles of sialic acid residues per mole of rhGAA.

* * * * *